US007504403B2

(12) United States Patent
Frohn et al.

(10) Patent No.: US 7,504,403 B2
(45) Date of Patent: Mar. 17, 2009

(54) SUBSTITUTED HETEROCYCLIC COMPOUNDS AND METHODS OF USE

(75) Inventors: Michael J. Frohn, Thousand Oaks, CA (US); Fang-Tsao Hong, Thousand Oaks, CA (US); Longbin Liu, Thousand Oaks, CA (US); Patricia Lopez, West Hills, CA (US); Aaron Siegmund, Ventura, CA (US); Seifu Tadesse, Simi Valley, CA (US); Nuria Tamayo, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 441 days.

(21) Appl. No.: 11/041,151

(22) Filed: Jan. 21, 2005

(65) Prior Publication Data

US 2005/0187223 A1 Aug. 25, 2005

Related U.S. Application Data

(60) Provisional application No. 60/538,948, filed on Jan. 22, 2004.

(51) Int. Cl.
*C07D 487/04* (2006.01)
*A61K 31/506* (2006.01)
(52) U.S. Cl. ............ 514/259.1; 514/259.4; 514/259.41; 514/259.5; 544/279; 544/281; 544/282
(58) Field of Classification Search ................. 544/279, 544/281, 282; 514/259.1, 259.4, 259.41, 514/259.5
See application file for complete search history.

(56) References Cited

U.S. PATENT DOCUMENTS 6,342,503 B1 1/2002 Aldrich et al.

FOREIGN PATENT DOCUMENTS

| JP | 55 2656 | 1/1980 |
|---|---|---|
| WO | WO 02/18385 | 3/2002 |
| WO | WO 03/000682 | 1/2003 |
| WO | WO 03/008413 | 1/2003 |
| WO | WO 03/011836 | 2/2003 |
| WO | WO 03/011837 | 2/2003 |
| WO | WO 03/011838 | 2/2003 |
| WO | WO 03/027115 | 4/2003 |
| WO | WO 03/027116 | 4/2003 |
| WO | WO 03/030909 | 4/2003 |
| WO | WO 03/047577 | 6/2003 |

OTHER PUBLICATIONS

Douglas, Jr., Introduction to Viral Diseases, Cecil Textbook of Medicine, oth Edition, vol. 2, pp. 1739-1747, 1996.*
Damasio, Alzheimer's Disease and Related Dementias, Cecil Textbook of Medicine, 20th Edition, vol. 2, pp. 1992-1996, 1996.*
Gomaraschi et al., High-density lipoproteins attenuate interleukin-6 production in endothelial cells exposed to pro-inflammatory stimuli, Biochimica et Biophysica Acta, 1736 (2005) pp. 136-143.*
Casanova et al., PubMed Abstract (Rev Neurol. 28(9):909-15) May 1999.*
Ben-Hur et al., Cytokine-mediated modulation of MMPs and TIMPs in multipotential neural precursor cells, Journal of Neuroimmunology 175 (2006) pp. 12-18.*
Vuolteenaho et al., Effects of TNFalpha-antagonists on nitric oxide production in human cartilage, Osteoarthritis and Cartilage (2002) 10, pp. 327-332.*
Vippagunta et al., Crystalline Solids, Advanced Drug Delivery Reviews, 48, pp. 3-26, 2001.*
West, Solid Solutions, Chapter 10, pp. 358 and 365, 1988.*
Abdel-Aziz, et al.; Phosphorus, Sulfur, and Silicon, Fused Cyanopyrimidines: Part II Synthesis and Reactions of Fused Cyanopyrimidine Derivatives as Affecting Enzymatic Agents; 113; 67-77 (1996).

* cited by examiner

*Primary Examiner*—Deepak Rao
(74) *Attorney, Agent, or Firm*—G. Prabhakar Reddy

(57) ABSTRACT

The present invention relates to pyrimidinones and pyridones and derivatives thereof, and pharmaceutically acceptable salts thereof. Also included is a method of treatment of inflammation, rheumatoid arthritis, Pagets disease, osteoporosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount a compound as described above.

17 Claims, No Drawings

SUBSTITUTED HETEROCYCLIC COMPOUNDS AND METHODS OF USE

This application claims the benefit of U.S. Provisional Application No. 60/538,948, filed Jan. 22, 2004, which is hereby incorporated by reference.

BACKGROUND OF THE INVENTION

The present invention comprises a new class of compounds useful in treating diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. This invention also relates to intermediates and processes useful in the preparation of such compounds.

Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide-LPS) or external cellular stress (e.g., osmotic shock and peroxide).

Elevated levels of TNF-α and/or IL-1 over basal levels have been implicated in mediating or exacerbating a number of disease states including rheumatoid arthritis; Pagets disease; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, *Stroke* 25, 1481 (1994)). TNF-α has also been implicated to play a role in type II diabetes (Endocrinol. 130, 43-52, 1994; and Endocrinol. 136, 1474-1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8.

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517-531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 40 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α:. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195-223 (1995)). These approaches block the effects of TNF-α and IL-1 by either protein sequestration or receptor antagonism.

U.S. Pat. No. 5,100,897, incorporated herein by reference in its entirety, describes pyrimidinone compounds useful as angiotensin II antagonists wherein one of the pyrimidinone ring nitrogen atoms is substituted with a substituted phenylmethyl or phenethyl radical.

U.S. Pat. No. 5,162,325, incorporated herein by reference in its entirety, describes pyrimidinone compounds useful as angiotensin II antagonists wherein one of the pyrimidinone ring nitrogen atoms is substituted with a substituted phenylmethyl radical.

EP 481448, incorporated herein by reference in its entirety, describes pyrimidinone compounds useful as angiotensin II antagonists wherein one of the pyrimidinone ring nitrogen atoms is substituted with a substituted phenyl, phenylmethyl or phenethyl radical.

CA 2,020,370, incorporated herein by reference in its entirety, describes pyrimidinone compounds useful as angiotensin II antagonists wherein one of the pyrimidinone ring nitrogen atoms is substituted with a substituted biphenylaliphatic hydrocarbon radical.

BRIEF DESCRIPTION OF THE INVENTION

The present invention comprises a new class of compounds useful in the prophylaxis and treatment of diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. Accordingly, the invention also comprises pharmaceutical compositions comprising the compounds; methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure:

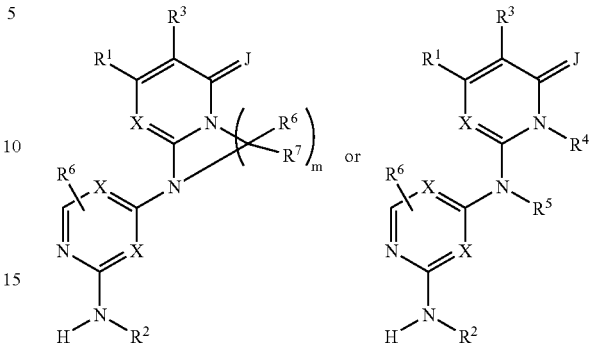

wherein $R^1$, $R^2$, $R^3$, $R^4$, $R^5$, $R^6$, J and X are defined herein.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, there is provided compounds of the formula:

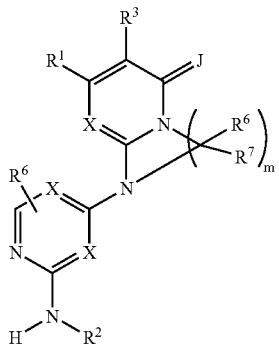

or a pharmaceutically acceptable salt or hydrate thereof, wherein

J is =O, =S, =CHNO$_2$, =N—CN, =CHSO$_2$R$^b$, =NSO$_2$R$^b$ or =NHR$^b$;

X is, independently at each instance, N or CR$^3$;

$R^1$ is a saturated or unsaturated 5- or 6-membered, ring containing 0, 1, 2 or 3 atoms selected from N, O and S, wherein the ring is substituted by 0, 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)

S(=O)$_2$R$^b$, —N(R$^a$)S(=O)$_2$NR$^a$R$^a$, —NR$^a$C$_{2-6}$ alkylNR$^a$R$^a$ and —NR$^a$C$_{2-6}$alkylOR$^a$;

R$^2$ is C$_{1-8}$alkyl substituted by 0, 1, 2 or 3 substituents selected from C$_{1-2}$haloalkyl, halo, oxo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkylNR$^a$R$^a$ and —NR$^a$C$_{2-6}$alkylOR$^a$, and additionally substituted by 0, 1 or 2 substituents selected from R$^g$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —C(=O)R$^e$, C(=O)OR$^e$, —C(=O)NR$^a$R$^e$, —C(=NR$^a$)NR$^a$R$^e$, —OR$^e$, —OC(=O)R$^e$, —OC(=O)NR$^a$R$^e$, —OC(=O)N(R$^a$)S(=O)$_2$R$^e$, —OC$_{2-6}$alkyNR$^a$R$^e$, —OC$_{2-6}$alkylOR$^e$, —SR$^e$, —S(=O)R$^e$, —S(=O)$_2$R$^e$, —S(=O)$_2$NR$^a$R$^e$, —NR$^a$R$^e$, —N(R$^a$)C(=O)R$^e$, —N(R$^a$)C(=O)OR$^e$ and —N(R$^a$)C(=O)NR$^a$R$^e$;

R$^3$ is selected from H, R$^e$, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^6$ is independently at each instance H, R$^d$, R$^e$ or R$^g$;

R$^7$ is independently at each instance H, R$^d$, R$^e$ or R$^g$;

m is 2 or 3;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;

R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^e$ is independently at each instance C$_{1-6}$alkyl substituted by 0, 1, 2 or 3 substituents independently selected from R$^d$ and additionally substituted by 0 or 1 substituents selected from R$^g$; and R$^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1 or 2 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with the above and below embodiments,

R$^1$ is a saturated or unsaturated 5- or 6-membered, ring containing 0, 1, 2 or 3 atoms selected from N, O and S, wherein the ring is substituted by 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with the above and below embodiments,

R$^1$ is a saturated or unsaturated 5- or 6-membered, ring containing 0, 1, 2 or 3 atoms selected from N, O and S, wherein the ring is substituted by 1, 2 or 3 substituents selected from C$_{1-4}$alkyl, C$_{1-4}$haloalkyl, halo, cyano, nitro, —OR$^a$, —OC(=O)R$^b$, —SR$^a$, —S(=O)R$^b$, —S(=O)$_2$R$^b$, —NR$^a$R$^a$ and —N(R$^a$)C(=O)R$^b$.

In another embodiment, in conjunction with the above and below embodiments,

R$^1$ is a saturated or unsaturated 5- or 6-membered, ring containing 0, 1, 2 or 3 atoms selected from N, O and S, wherein the ring is substituted by 0, 1, 2 or 3 substituents selected from C$_{1-4}$alkyl, C$_{1-4}$haloalkyl and halo.

In another embodiment, in conjunction with the above and below embodiments,

R$^1$ is a saturated or unsaturated 6-membered, ring containing 0, 1, 2 or 3 atoms selected from N, O and S, wherein the ring is substituted by 0, 1, 2 or 3 substituents selected from C$_{1-4}$alkyl, C$_{1-4}$haloalkyl and halo.

In another embodiment, in conjunction with the above and below embodiments,

R$^1$ is phenyl substituted by 0, 1, 2 or 3 substituents selected from C$_{1-4}$alkyl, C$_{1-4}$haloalkyl and halo.

In another embodiment, in conjunction with the above and below embodiments,

R$^1$ is pyridinyl substituted by 0, 1, 2 or 3 substituents selected from C$_{1-4}$alkyl, C$_{1-4}$haloalkyl and halo.

In another embodiment, in conjunction with the above and below embodiments, $R^1$ is pyrimidinyl substituted by 0, 1, 2 or 3 substituents selected from $C_{1-4}$alkyl, $C_{1-4}$haloalkyl and halo.

In another embodiment, in conjunction with the above and below embodiments, $R^1$ is a saturated or unsaturated 5-membered, ring containing 1 or 2 atoms selected from N, O and S, wherein the ring is substituted by 0, 1, 2 or 3 substituents selected from $C_{1-4}$alkyl, $C_{1-4}$haloalkyl and halo.

In another embodiment, in conjunction with the above and below embodiments, $R^2$ is $C_{1-8}$alkyl substituted by 0, 1, 2 or 3 substituents selected from $C_{1-2}$haloalkyl, halo, oxo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by 0, 1 or 2 substituents selected from $R^g$, —C(=O)$R^g$, —C(=O)O$R^g$, —C(=O)N$R^aR^g$, —C(=N$R^a$)N$R^aR^g$, —O$R^g$, —OC(=O)$R^g$, —OC(=O)N$R^aR^g$, —OC(=O)N($R^a$)S(=O)$_2R^g$, —O$C_{2-6}$alkylN$R^aR^g$, —O$C_{2-6}$alkylO$R^g$, —S$R^g$, —S(=O)$R^g$, —S(=O)$_2R^g$, —S(=O)$_2$N$R^aR^g$, —N$R^aR^g$, —N($R^a$)C(=O)$R^g$, —N($R^a$)C(=O)O$R^g$, —N($R^a$)C(=O)N$R^aR^g$, —C(=O)$R^e$, —C(=O)O$R^e$, —C(=O)N$R^aR^e$, —C(=N$R^a$)N$R^aR^e$, —O$R^e$, —OC(=O)$R^e$, —OC(=O)N$R^aR^e$, —OC(=O)N($R^a$)S(=O)$_2R^e$, —O$C_{2-6}$alkylN$R^aR^e$, —O$C_{2-6}$alkylO$R^e$, —S$R^e$, —S(=O)$R^e$, —S(=)$_2R^e$, —S(=O)$_2$N$R^aR^e$, —N$R^aR^e$, —N($R^a$)C(=O)$R^e$, —N($R^a$)C(=O)O$R^e$ and —N($R^a$)C(=O)N$R^aR^e$.

In another embodiment, in conjunction with the above and below embodiments, $R^2$ is $C_{1-8}$alkyl substituted by 0, 1, 2 or 3 substituents selected from $C_{1-2}$haloalkyl, halo, oxo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by $R^g$.

In another embodiment, in conjunction with the above and below embodiments, $R^2$ is $C_{1-8}$alkyl substituted by 1, 2 or 3 substituents selected from $C_{1-2}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by $R^g$.

In another embodiment, in conjunction with the above and below embodiments, $R^2$ is $C_{1-8}$alkyl substituted by $R^g$.

In another embodiment, in conjunction with the above and below embodiments, $R^2$ is —$C_{1-6}$alkylphenyl, wherein the phenyl is 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with the above and below embodiments, $R^3$ is selected from $R^e$, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$.

In another embodiment, in conjunction with the above and below embodiments, $R^3$ is H.

In another embodiment, in conjunction with any of the above and below embodiments, J is =O or =S.

In another embodiment, in conjunction with any of the above and below embodiments, J is =CHNO$_2$ or =CHSO$_2R^b$.

In another embodiment, in conjunction with any of the above and below embodiments, J is =N—CN, =NSO$_2R^b$ or =N$R^b$.

Another aspect of the invention relates to compounds having the structure

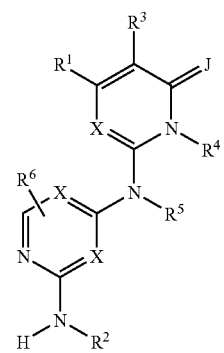

or a pharmaceutically acceptable salt or hydrate thereof, wherein

J is =O, =S, =CHNO$_2$, =N—CN, =CHSO$_2R^b$, =NSO$_2R^b$ or =NH$R^b$;

X is, independently at each instance, N or C$R^3$;

$R^1$ is a saturated or unsaturated 5-, 6- or 7-membered, ring containing 0, 1, 2 or 3 atoms selected from N, O and S, wherein the ring is substituted by 0, 1, 2 or 3 substituents selected from $C_{1-4}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —NR$C_{2-6}$alkylO$R^a$; wherein $R^1$ is not thiazole, imidazole or pyrazole;

$R^2$ is $C_{2-8}$alkyl substituted by 0, 1, 2 or 3 substituents selected from $C_{1-2}$haloalkyl, halo, oxo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by 0, 1 or 2 substituents selected from $R^g$, —C(=O)$R^g$, —C(=O)O$R^g$, —C(=O)N$R^aR^g$, —C(=N$R^a$)N$R^aR^g$, —O$R^g$, —OC(=O)$R^g$, —OC(=O)N$R^aR^g$, —OC(=O)N($R^a$)S(=O)$_2R^g$, —O$C_{2-6}$alkylN$R^aR^g$, —O$C_{2-6}$alkylO$R^g$, —S$R^g$, —S(=O)$R^g$, —S(=O)$_2R^g$, =S(=O)$_2$N$R^aR^g$, —N$R^aR^g$, —N($R^a$)C(=O)$R^g$, —N($R^a$)C(=O)O$R^g$, —N($R^a$)C(=O)N$R^aR^g$, —C(=O)$R^e$, C(=O)O$R^e$, —C(=O)N$R^aR^e$, —C(=N$R^a$)N$R^aR^e$, —O$R^e$, —OC(=O)$R^e$, —OC(=O)N$R^aR^e$, —OC(=O)N($R^a$)S(=O)$_2R^e$, —O$C_{2-6}$alkylN$R^aR^e$, —O$C_{2-6}$alkylO$R^e$, —S$R^e$, —S(=O)$R^e$, —S(=O)$_2R^e$, —S(=O)$_2$N$R^aR^e$, —N$R^aR^e$, —N($R^a$)C(=O)$R^e$, —N($R^a$)C(=O)O$R^e$ and —N($R^a$)C(=O)N$R^aR^e$;

$R^3$ is independently, in each instance, selected from H, $R^e$, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$R^4$ is H, $R^e$ or $R^g$;

$R^5$ is H, $R^e$ or $R^g$;

$R^6$ is independently at each instance H, $R^d$, $R^e$ or $R^g$;

$R^7$ is independently at each instance H, $R^d$, $R^e$ or $R^g$;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —O$C_{1-4}$alkyl, —NH$_2$, —NH$C_{1-4}$alkyl, —N($C_{1-4}$alkyl)$C_{1-4}$alkyl;

$R^d$ is independently at each instance $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$R^e$ is independently at each instance $C_{1-6}$alkyl substituted by 0, 1, 2 or 3 substituents independently selected from $R^d$ and additionally substituted by 0 or 1 substituents selected from $R^g$; and $R^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —NR$C_{2-6}$alkylN$R^aR^a$ and —N$R^aC_{2-6}$alkylO$R^a$.

In another embodiment, in conjunction with the above and below embodiments, $R^1$ is thiophenyl, furanyl, pyrrolyl, oxazole or triazole, any of which is substituted by 0, 1, 2 or 3 substituents selected from $C_{1-4}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^a$ and —N$R^aC_{2-6}$alkylO$R^a$; wherein $R^1$ is not thiazole, imidazole or pyrazole.

In another embodiment, in conjunction with the above and below embodiments, $R^1$ is a saturated or unsaturated 6-membered, ring containing 1, 2 or 3 atoms selected from N, O and S, wherein the ring is substituted by 0, 1, 2 or 3 substituents selected from $C_{1-4}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)

$S(=O)_2R^b$, —$N(R^a)S(=O)_2NR^aR^a$, —$NR^aC_{2-6}alkylNR^aR^a$ and —$NR^aC_{1-6}alkylOR^a$.

In another embodiment, in conjunction with the above and below embodiments, $R^1$ is an unsaturated 6-membered, ring containing 1, 2 or 3 N atoms, wherein the ring is substituted by 0, 1, 2 or 3 substituents selected from $C_{1-4}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ and —$NR^aC_{2-6}alkylOR^a$.

In another embodiment, in conjunction with the above and below embodiments, $R^1$ is phenyl substituted by 0, 1, 2 or 3 substituents selected from $C_{1-4}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, $OR^a$, —$OC(=O)R^b$, —$OC(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ and —$NR^aC_{2-6}alkylOR^a$.

In another embodiment, in conjunction with the above and below embodiments, $R^1$ is phenyl substituted by 1, 2 or 3 substituents selected from $C_{1-4}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ and —$NR^aC_{2-6}alkylOR^a$.

In another embodiment, in conjunction with the above and below embodiments, $R^1$ is phenyl, pyridinyl or pyrimidinyl, all of which are substituted by 0, 1 or 2 substituents selected from halo, $C_{1-3}$alkyl and $CF_3$.

In another embodiment, in conjunction with the above and below embodiments, $R^1$ is phenyl, pyridinyl or pyrimidinyl.

In another embodiment, in conjunction with the above and below embodiments, $R^1$ is phenyl.

In another embodiment, in conjunction with the above and below embodiments, $R^2$ is $C_{2-8}$alkyl.

In another embodiment, in conjunction with the above and below embodiments, $R^2$ is $C_{2-8}$alkyl substituted by $R^g$.

In another embodiment, in conjunction with the above and below embodiments, $R^2$ is $C_{2-8}$alkyl substituted by 1, 2 or 3 substituents selected from $C_{1-2}$haloalkyl, halo, oxo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ and —$NR^aC_{2-6}alkylOR^a$, and additionally substituted by $R^g$.

In another embodiment, in conjunction with the above and below embodiments, $R^2$ is $C_{2-8}$alkyl substituted by phenyl, the phenyl being substituted by 0, 1, 2 or 3 substituents selected from $C_{1-8}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ and —$NR^aC_{2-6}alkylOR^a$.

In another embodiment, in conjunction with the above and below embodiments, $R^2$ is $C_{2-8}$alkyl substituted by 1, 2 or 3 substituents selected from $C_{1-2}$haloalkyl, halo, oxo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$C(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ and —$NR^aC_{2-6}alkylOR^a$, and additionally substituted by , the phenyl being substituted by 0, 1, 2 or 3 substituents selected from $C_{1-8}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ and —$NR^aC_{2-6}alkylOR^a$.

In another embodiment, in conjunction with the above and below embodiments, $R^3$ is selected from $R^e$, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}alkylNR^aR^a$, —$OC_{2-6}alkylOR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}alkylNR^aR^a$ or —$NR^aC_{2-6}alkylOR^a$.

In another embodiment, in conjunction with the above and below embodiments, $R^3$ is H.

In another embodiment, in conjunction with any of the above and below embodiments, J is =O or =S.

In another embodiment, in conjunction with any of the above and below embodiments, J is =CHNO$_2$ or =CHSO$_2$R$^b$.

In another embodiment, in conjunction with any of the above and below embodiments, J is =N—CN, =NSO$_2$R$^b$ or =NR$^b$.

Another aspect of the invention relates to a pharmaceutical composition comprising a compound according to any one of the above embodiments and a pharmaceutically acceptable carrier.

Another aspect of the invention relates to a method of prophylaxis or treatment of inflammation comprising administering an effective amount of a compound according to any one of the above embodiments.

Another aspect of the invention relates to a method of prophylaxis or treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a compound according to any one of the above embodiments.

Another aspect of the invention relates to a method of lowering plasma concentrations of either or both TNF-α and IL-1 comprising administering an effective amount of a compound according to any one of the above embodiments.

Another aspect of the invention relates to a method of lowering plasma concentrations of either or both IL-6 and IL-8 comprising administering an effective amount of a compound according to any one of the above embodiments.

Another aspect of the invention relates to a method of prophylaxis or treatment of diabetes disease in a mammal comprising administering an effective amount of a compound according to any one of the above embodiments to produce a glucagon antagonist effect.

Another aspect of the invention relates to a method of prophylaxis or treatment of a pain disorder in a mammal comprising administering an effective amount of a compound according to any one of the above embodiments.

Another aspect of the invention relates to a method of decreasing prostaglandins production in a mammal comprising administering an effective amount of a compound according to any one of the above embodiments.

Another aspect of the invention relates to a method of decreasing cyclooxygenase enzyme activity in a mammal comprising administering an effective amount of a compound according to any one of the above embodiments. In another embodiment, the cyclooxygenase enzyme is COX-2.

Another aspect of the invention relates to a method of decreasing cyclooxygenase enzyme activity in a mammal comprising administering an effective amount of the above pharmaceutical composition. In another embodiment the cyclooxygenase enzyme is COX-2.

Another aspect of the invention relates to the manufacture of a medicament comprising a compound according to any one of the above embodiments.

Another aspect of the invention relates to the manufacture of a medicament for the treatment of inflammation comprising administering an effective amount of a compound according to any one of the above embodiments.

Another aspect of the invention relates to the manufacture of a medicament for the treatment of rheumatoid arthritis, Pagets disease, osteoporosis, multiple myeloma, uveitis, acute or chronic myelogenous leukemia, pancreatic D cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a compound according to any one of the above embodiments.

The compounds of this invention may have in general several asymmetric centers and are typically depicted in the form of racemic mixtures. This invention is intended to encompass racemic mixtures, partially racemic mixtures and separate enantiomers and diastereomers.

The specification and claims contain listing of species using the language "selected from . . . and . . ." and "is . . . or . . ." (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Unless otherwise specified, the following definitions apply to terms found in the specification and claims:

"Aryl" means a phenyl or naphthyl radical, wherein the phenyl may be fused with a $C_{3-4}$cycloalkyl bridge.

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like. "$C_{\alpha-\mu}$alkyl" means an alkyl group comprising from α to βcarbon atoms in a branched, cyclical or linear relationship or any combination of the three. The alkyl groups described in this section may also contain double or triple bonds. Examples of $C_{1-8}$alkyl include, but are not limited to the following:

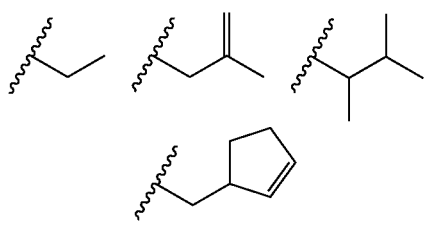

"Halogen" and "halo" mean a halogen atoms selected from F, Cl, Br and I. "$C_{\alpha-\beta}$haloalkyl" means an alkyl group, as described above, wherein any number—at least one—of the hydrogen atoms attached to the alkyl chain are replaced by F, Cl, Br or I. "Heterocycle" means a ring comprising at least one carbon atom and at least one other atom selected from N, O and S. Examples of heterocycles that may be found in the claims include, but are not limited to, the following:

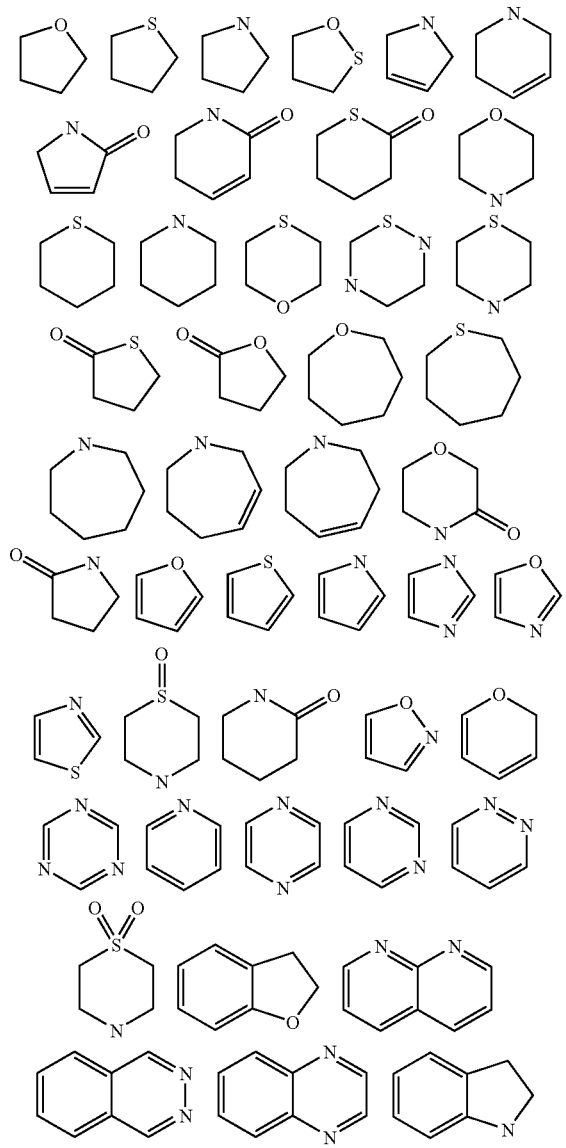

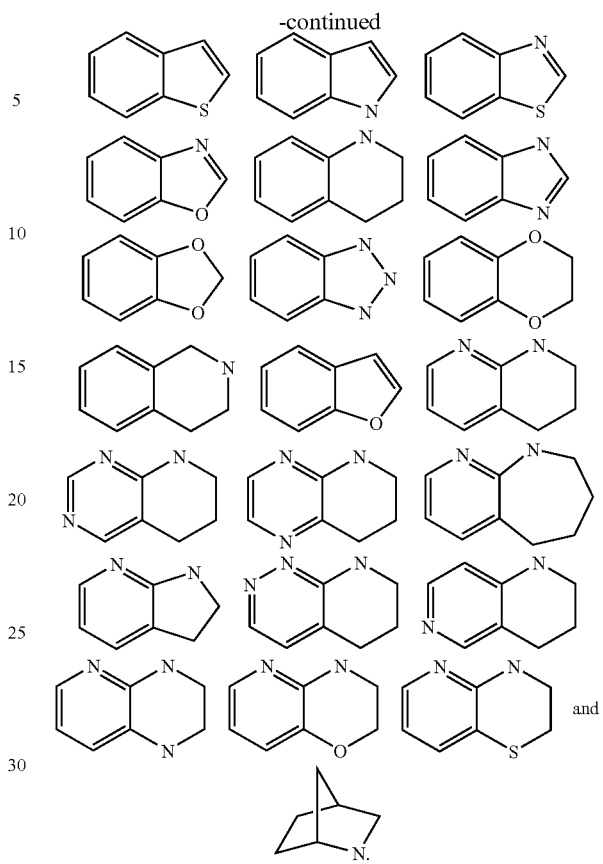

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977). "Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate. "Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

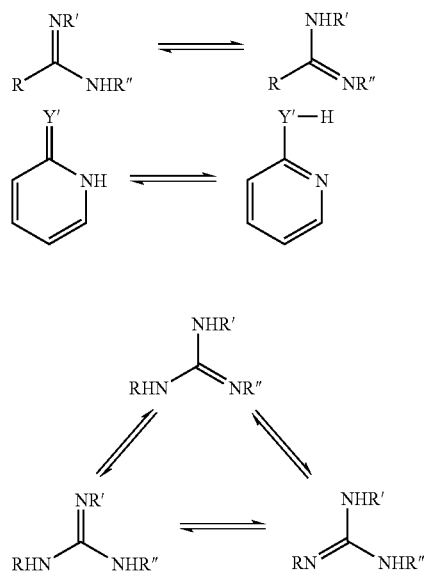

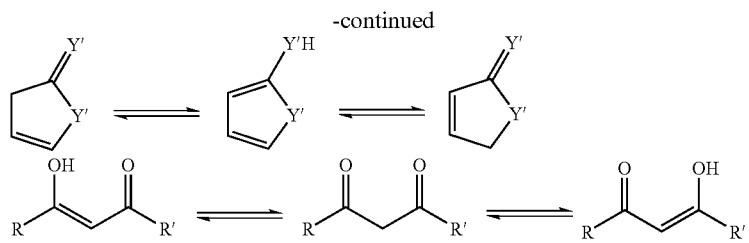

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. "Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

Synthetic Scheme A:

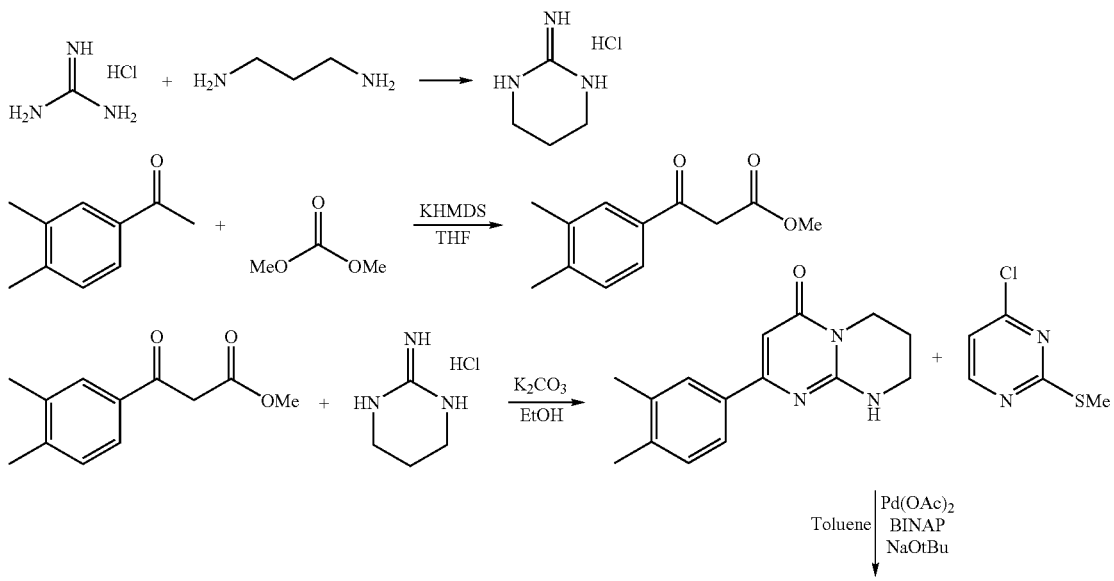

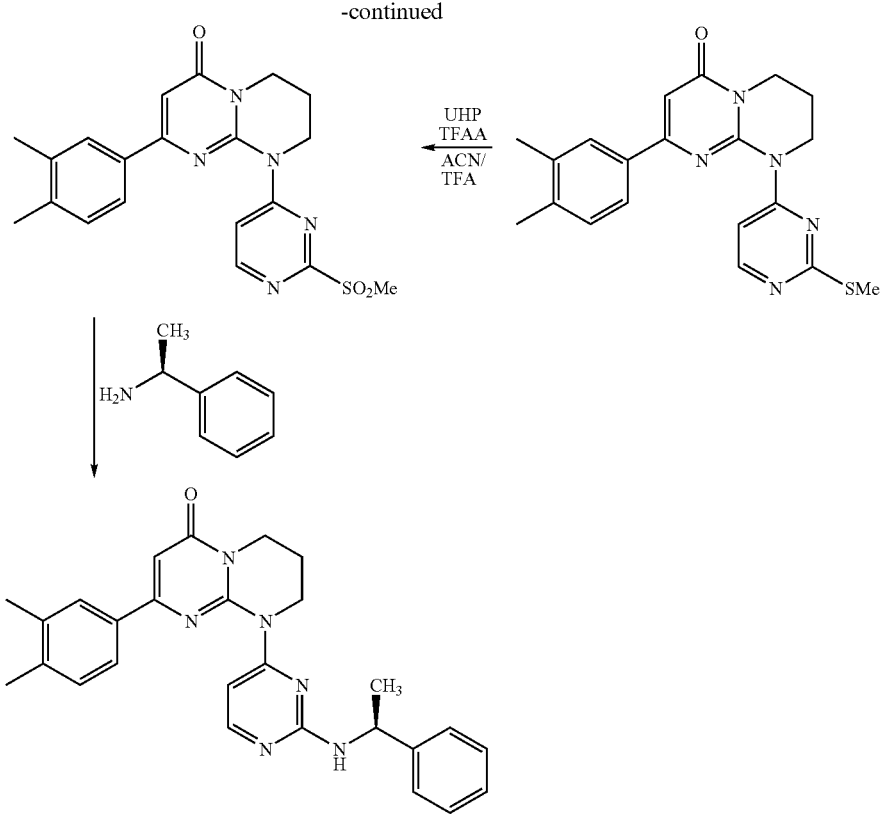

EXAMPLE 1

Tetrahydro-pyrimidin-2-ylideneamine hydrochloride: A suspension of 1,3-diaminopropane (74 g, 1 mol) and guanidine hydrochloride (76 g, 0.8 mol) was heated to 140° C. while stirring for 20 h. Reaction temperature lowered to 100° C. and isopropyl alcohol (100 mL) added. At room temperature resulting solid collected by filtration and solid washed with diethyl ether. Air dried overnight. White powder. M+1=100.

3-(3,4-Dimethyl-phenyl)-3-oxo-propionic acid methyl ester: To a stirring solution of 3,4-dimethylacetophenone (1.0 g, 6.8 mmol) in tetrahydrofuran (10 ML) at 0° C. under an atmosphere of nitrogen was added potassium hexamethyldisilylzide (1.46 g, 6.8 mmol). Resulting suspension was stirred for 10 min and dimethylcarbonate (0.58 mL, 6.8 mmol) added. Reaction stirred for 16 h warming to room temperature then poured onto wet ice (50 mL)/ hydrochloric acid (5 mL). Product extracted with ethyl acetate (50 mL) and organic washed with saturated sodium chloride then dried over magnesium sulfate. Product isolated as an amber oil after removal of solvent under vacuum. M+1=207.

2-(3,4-Dimethyl-phenyl)-6,7,8,9-tetrahydro-pyrimido[1,2-a]pyrimidin4-one: A suspension of 3-(3,4-dimethyl-phenyl)-3-oxo-propionic acid methyl ester (1.2 g, 5.8 mmol), tetrahydro-pyrimidin-2-ylideneamine hydrochloride (0.78 g, 5.8 mmol), and potassium carbonate (0.80 g, 5.8 mmol) in ethanol (20 mL) was heated to reflux for 4 h. Water (5 mL) was added to the reaction at room temperature and tan solid was collected by filtration. M+1=256.

2-(3,4-Dimethyl-phenyl)-9-(2-methylsulfanyl-pyrimidin-4-yl)-6,7,8,9-tetrahydro-pyrimido[1,2-a]pyrimidin-4-one: A suspension of 2-(3,4-dimethyl-phenyl)-6,7,8,9-tetrahydropyrimido[1,2-a]pyrimidin-4-one (400 mg, 1.6 mmol), 4-chloro-2-methylthiopyrimidinone (0.24 mL, 2.0 mmol), palladium acetate (11 mg, 0.05 mmol), bis(diphenylphosphino)-1,1'-binaphthyl (37 mg, 0.05 mmol), and sodium tert-butoxide (192 mg, 2.0 mmol) was heated to reflux in toluene (6 mL) under an atmosphere of nitrogen overnight. Reaction diluted with ethyl acetate (50 mL) and organics washed with saturated ammonium chloride. Solvents removed under vacuum, and resulting pale yellow solids washed with methanol/ diethyl ether (1:10, 2 mL). M+1=380.

2-(3,4-Dimethyl-phenyl)-9-(2-methanesulfonyl-pyrimidin-4-yl)-6,7,8,9-tetrahydro-pyrimido[1,2-a]pyrimidin-4-one: To a stirring solution of 2-(3,4-Dimethyl-phenyl) -9-(2-methylsulfanyl-pyrimidin-4-yl)-6,7,8,9-tetrahydro-pyrimido[1,2-a]pyrimidin-4-one (260 mg, 0.69 mmol) in acetonitrile (2 mL) and trifluoroacetic acid (2 mL) at 0° C. under an atmosphere of nitrogen was added urea hydrogen peroxide (129 mg, 1.37 mmol) and trifluoroacetic anhydride (0.20 mL, 1.4 mmol). After 30 min, solvents removed under vacuum, and residue was partitioned between dichloromethane (50 mL) and 5 % sodium bicarbonate (10 mL). Organic dried over magnesium sulfate, then concentrated to a solid under vacuum. M+1=412.

2-(3,4-Dimethyl-phenyl)-9-[2-(1(S)-phenyl-ethylamino) -pyrimidin-4-yl]-6,7,8,9-tetrahydro-pyrimido[1,2-a]pyrimidin-4-one: A suspension of 2-(3,4-dimethylphenyl)-9-(2-methanesulfonyl-pyrimidin-4-yl)-6,7,8,9-tetrahydro-pyrimido[1,2-a]pyrimidin-4-one (150 mg, 0.36 mmol) and S-(−)-α-methylbenzylamine (1.3 mL, 10 mmol) was heated to 90° C. in dioxane (1 mL) for 5 h. Reaction concentrated under vacuum and purified on silica. Resulting pale yellow solid washed with methanol/ diethyl ether (1: 10, 2 mL). M+1=453.

$^1$H NMR (CDCl$_3$) d (3H, 1.58 ppm), t (2H, 2.11 ppm), s (6H, 2.29 ppm), m (1H, 3.99 ppm), m (1H, 4.04 ppm), m (1H, 4.11 ppm), m (1H, 5.08 ppm), m (1H, 5.40 ppm), s (1H, 6.56 ppm), d (1H, 7.18 ppm), m (2H, 7.23 ppm), t (2H, 7.33 ppm), d (2H, 7.38 ppm), dd (1H, 7.62 ppm), s (1H, 7.67 ppm), d (1H, 8.13 ppm).

The examples in the following table were prepared using the above method, but substituting 3,4-dimethylacetophenone with the appropriate methyl ketone.

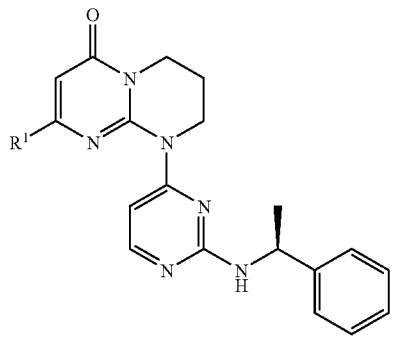

| Example | R$^1$ | HPLC RT (method) | MS M + 1 |
|---|---|---|---|
| 1 | 3,4-dimethylphenyl | 7.41 (A) | 453 |
| 2 | 2-fluorophenyl | 7.06 (A) | 443 |
| 3 | 2-trifluoromethylphenyl | 7.32 (A) | 493 |
| 4 | 4-fluorophenyl | 7.06 (A) | 443 |
| 5 | 4-methoxyphenyl | 6.98 (A) | 455 |
| 6 | 3-nitrophenyl | 7.01 (A) | 470 |
| 7 | 3-aminophenyl | 5.64 (A) | 440 |
| 8 | 3-dimethylaminephenyl | 5.93 (A) | 468 |
| 9 | 4-pyridyl | N/A | 425 |
| 10 | phenyl | N/A | 424 |
| 11 | tert-butyl | 7.03 (A) | 405 |
| 12 | 3-ethylphenyl | 7.53 (A) | 453 |
| 13 | 3,4-dichlorophenyl | 7.73 (A) | 493 |

HPLC Method A: Luna C18 5 mm 100×4.6 mm; flow rate 1.0 mL/min with gradient of 0 min 5%→9 min 95%→9.5 min 95%-→10 min 5%. Solvent A: water (0.1% TFA); Solvent B: acetonitrile (0.1% TFA).

Synthetic Scheme B:

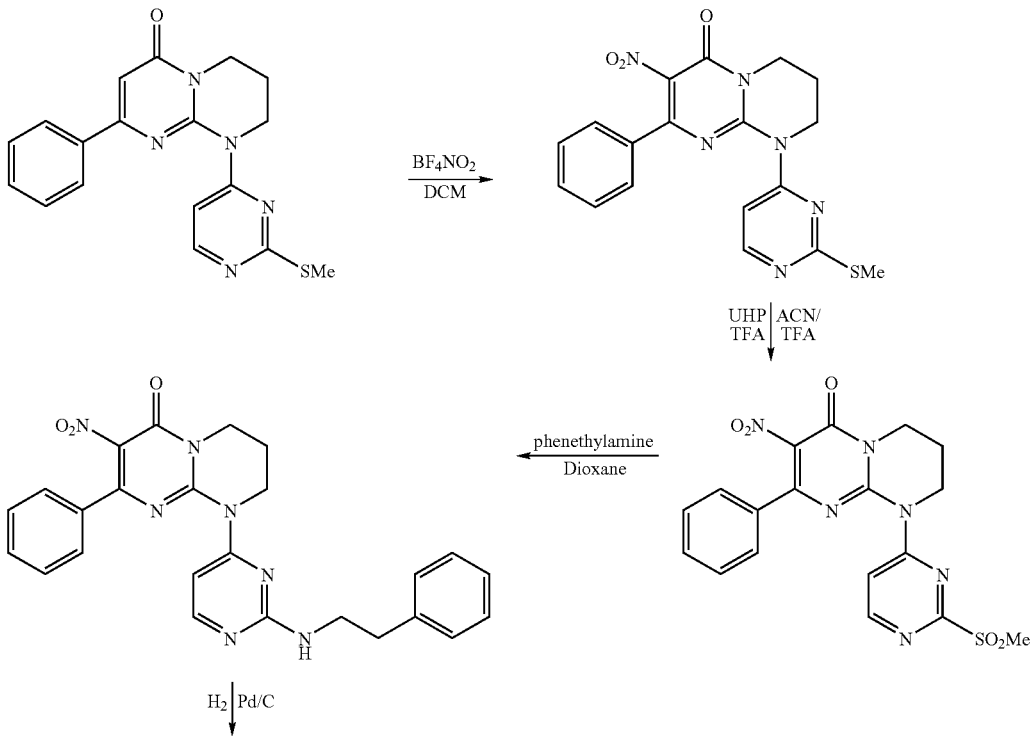

-continued

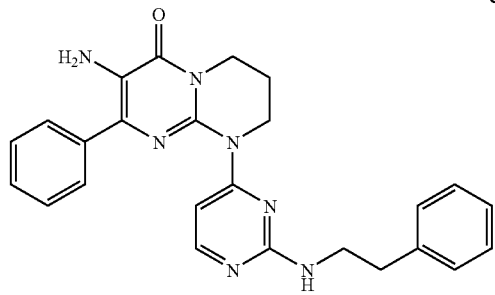

EXAMPLE 14

9-(2-Methylsulfanyl-pyrimidin-4-yl)-3-nitro-2-phenyl -6,7,8,9-tetrahydro-pyrimido[1,2-a]pyrimidin-4-one: To a stirring solution of 9-(2-methylsulfanyl-pyrimidin-4-yl)-2-phenyl-6,7,8,9-tetrahydro-pyrimido[1,2-a]pyrimidin-4-one (500 mg, 1.42 mmol) in dichloromethane (10 mL) at 0° C. under nitrogen was added nitronium tetrafluoroborate in a 0.5M solution (7 mL, 3.55 mmol). External cooling removed and reaction warmed to room temperature while stirring for 1 h. Reaction washed with 5% sodium bicarbonate and saturated ammonium chloride. Organic concentrated under vacuum and orange solid isolated after purification on silica. M+1=397.

9-(2-Methanesulfonyl-pyrimidin-4-yl)-3-nitro-2-phenyl -6,7,8,9-tetrahydro-pyrimido[1,2-a]pyrimidin-4-one: To a stirring solution of 9-(2-methylsulfanyl-pyrimidin-4-yl)-3-nitro-2-phenyl -6,7,8,9-tetrahydro-pyrimido[1,2-a]pyrimidin-4-one (235 mg, 0.59 mmol) in acetonitrile (2 mL) and trifluoroacetic acid (2 mL) at 0° C. under an atmosphere of nitrogen was added urea hydrogen peroxide (113 mg, 1.2 mmol) and trifluoroacetic anhydride (0.17 mL, 1.2 mmol). After 30 min solvents removed under vacuum, and residue was partitioned between dichloromethane (50 mL) and 5 % sodium bicarbonate (10 mL). Organic dried over magnesium sulfate, then concentrated to a solid under vacuum. M+1=429.

3-Nitro-9-(2-phenethylamino-pyrimidin-4-yl)-2-phenyl -6,7,8,9-tetrahydro-pyrimido[1,2-a]pyrimidin-4-one: A solution of 9-(2-methanesulfonyl-pyrimidin-4-yl) -3-nitro-2-phenyl -6,7,8,9-tetrahydro-pyrimido[1,2-a]pyrimidin-4-one (220 mg, 0.51 mmol) and phenethylamine (0.13 mL, 1.0 mmol) in dichloromethane (2 mL) was heated to 80° C. for 1 h. Residue purified on silica, and final product isolated as a white solid. M+1=470.

3-Amino-9-(2-phenethylamino-pyrimidin-4-yl) -2-phenyl - 6,7,8,9-tetrahydro-pyrimido[1,2-a]pyrimidin-4-one: A suspension of 3-nitro-9-(2-phenethylamino-pyrimidin-4-yl)-2-phenyl -6,7,8,9tetrahydro-pyrimido[1,2-a]pyrimidin-4-one (40 mg, 0.09 mmol) in methanol (10 mL) was stirred with 10 % palladium on carbon (5 mg) under an atmosphere of hydrogen for 4 h. Reaction mixture filtered through a bed of Celite, and final product isolated as a white solid after removal of solvent under vacuum. M+1=440 $^1$NMR (CDCl$_3$) t (2H, 2.20 ppm), t (2H, 2.91 ppm), dd (2H, 3.67 ppm), s (2H, 4.07 ppm), m (4H, 4.15 ppm), s (1H, 5.10 ppm), d (1H, 7.17 ppm), m (3H, 7.24 ppm), m (2H, 7.31 ppm), m (1H, 7.36 ppm), t (2H, 7.46 ppm), d (2H, 7.79 ppm), d (1H, 8.03 ppm).

3-Amino-9-{2-[2-(3-aminomethyl-phenyl)-1-methyl-ethylamino]-pyrimidin-4-yl}-2-phenyl -6,7,8,9-tetrahydro-pyrimido[1,2-a]pyrimidin-4-one: To a solution of 9-{2-[2-(3-azidomethyl-phenyl) -1-methyl-ethylamino]-pyrimidin-4-yl}-3-nitro-2-phenyl-6,7,8,9-tetrahydro-pyrimido[1,2-a] pyrimidin-4-one (61 mg, 0.11 mmol) in 1 mL methanol was safely added 10 mg palladium on carbon (10%) and stirred over an atmosphere of hydrogen delivered by a balloon. After 2 h, the reaction was filtered through a bed of Celite and solvent removed under reduced pressure. Product was purified on silica. M+1=483 1H NMR (CDCl$_3$) d (3H, 1.19 ppm), m (2H, 2.20 ppm), dd (1H, 2.76 ppm), dd (1H, 2.96 ppm), s (2H, 3.84 ppm), m (6H, 4.08 ppm), q (1H, 4.30 ppm), d (1H, 4.95 ppm), m (4H, 7.13 ppm), t (1H, 7.28 ppm), t (1H, 7.36 ppm), t (2H, 7.45 ppm), d (2H, 7.80 ppm), d (1H), 8.03 ppm).

The examples in the following table were prepared using the above methods, as indicated, using the appropirately substituted oxopropionic acid derivative from scheme A and the appropriate amine to replace the phenethylamine, if desired:

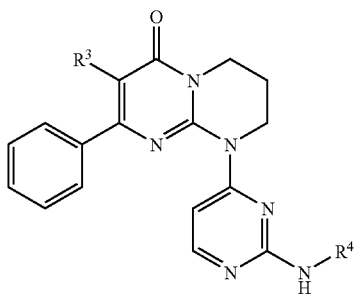

| Example | R$^3$ | R$^4$ | Synthetic Method | HPLC RT (method) | MS M + 1 |
|---|---|---|---|---|---|
| 14 | —NH$_2$ | -ethyl-1-methyl-2(3-methylaminophenyl) | A, B, D, E | 4.92 (A) | 483 |
| 15 | —NO$_2$ | -ethyl-2-phenyl | A, B | 7.09 (A) | 470 |
| 16 | —CH$_3$ | -1-(S)-phenylethyl | A | 7.20 (A) | 439 |
| 17 | —NH$_2$ | -ethyl-2-(2-chlorophenyl) | A, B | 6.87 (A) | 474 |
| 18 | —NH$_2$ | -ethyl-2-phenyl | A, B | 6.62 (A) | 440 |

Synthetic Scheme C:
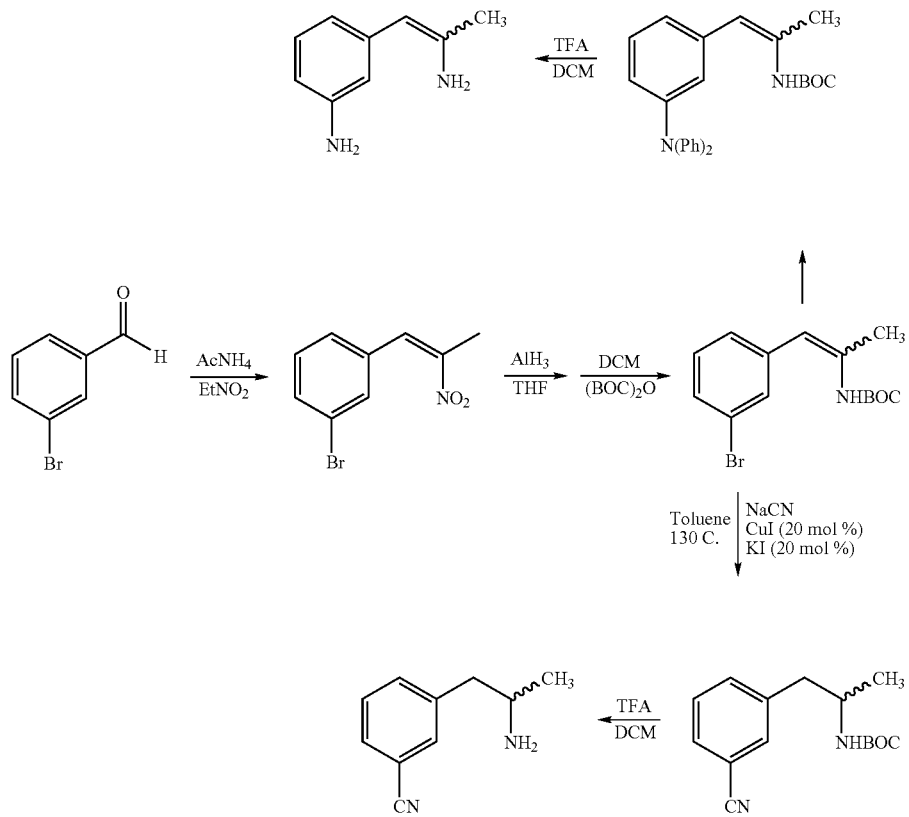
Synthetic Scheme D:
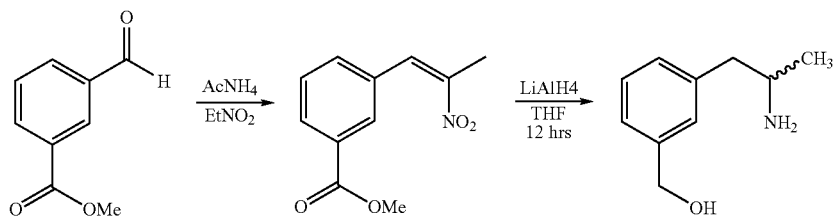
Synthetic Scheme E:
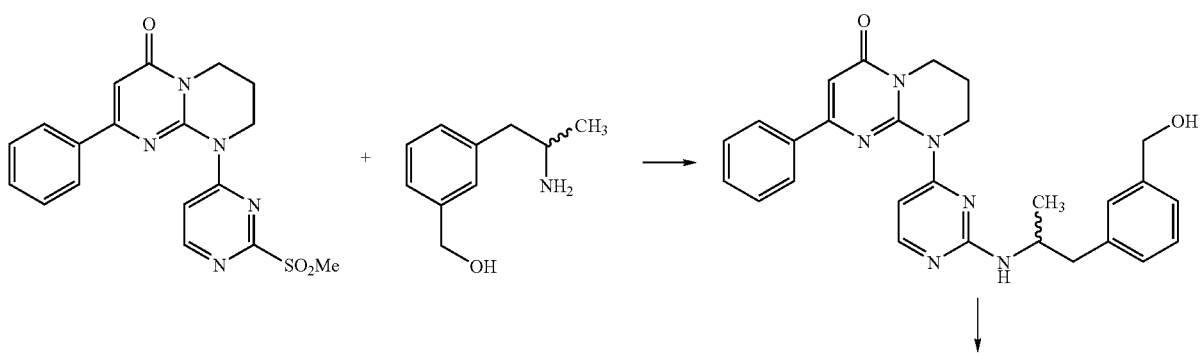

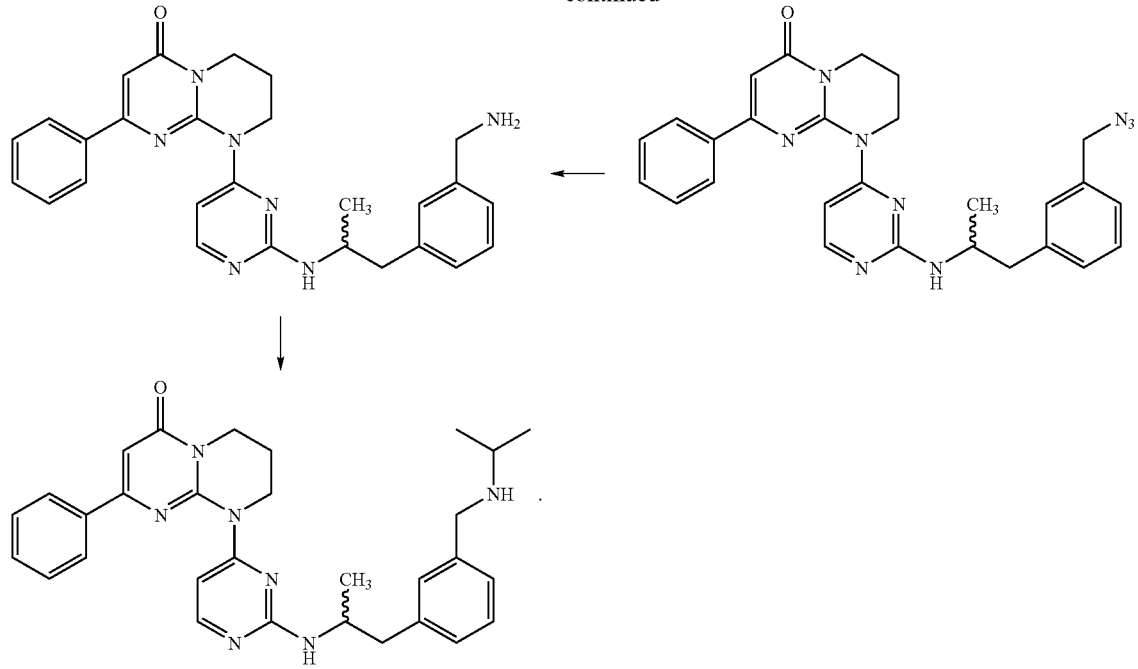

EXAMPLE 19

1-Bromo-3-(2-nitro-propenyl)-benzene: A suspension of 3-bromo-benzaldehyde (2.5 g, 13.5 mmol), ammonium acetate (1.09 g, 14.2 mmol), and nitroethane (250 mL) was heated to reflux overnight. Solvent removed under vacuum then residue partitioned between ethyl acetate and saturated sodium chloride. Concentrated organic purified on silica and isolated as a yellow oil. $^1$H NMR (CDCl$_3$) s (3H, 2.44 ppm), m (2H, 7.35 ppm), m (2H, 7.55 ppm) s (1H, 8.00 ppm).

[2-(3-Bromo-phenyl)-1-methyl-ethyl]-carbamic acid tert-butyl ester: To a stirring solution of lithium aluminum hydride (24 mL of 1 M in tetrahydrofuran (THF), 24 mmol) at 0° C. under an atmosphere of nitrogen was added sulfuric acid (0.61 mL, 12.0 mmol) in tetrahydrofuran (10 mL) dropwise. Then a solution of 1-bromo-3-(2-nitro-propenyl)-benzene (1.17 g, 4.8 mmol) in THF was added dropwise via an addition funnel. Reaction warmed to room temperature overnight. Reaction chilled to 0° C., and a saturated solution of potassium sodium tartrate tetrahydrate added to the reaction dropwise. Once a cake formed, the organic phase was reduced to an oil under vacuum. This residue was then dissolved in dichloromethane and dried over magnesium sulfate. Di-tert-butyldicarbonate (1.05 g, 4.8 mmol) added and solution stirred overnight at room temperature. Reaction reduced to an oil under vacuum and isolated as a white solid after purification on silica. M+1=314/316.

[2-(3-Cyano-phenyl)-1-methyl-ethyl]-carbamic acid tert-butyl ester: To a sealed pressure tube was added [2-(3-bromo-phenyl)-1-methyl-ethyl]-carbamic acid tert-butyl ester (1.23 g, 3.9 mmol), sodium cyanide (250 mg, 5.1 mmol), potassium iodide (130 mg, 0.8 mmol), N-N'-dimethylethylenediamine (0.41 mL, 3.9 mmol), and toluene (6 mL). This suspension was then sparged with nitrogen prior to adding copper iodide (150 mg, 0.8 mmol). Reaction mixture heated to 130° C. for 16 h while stirring. Reaction partitioned between ethyl acetate and 30% aqueous ammonia. Organic washed with saturated ammonium chloride, then dried over magnesium sulfate. Reaction reduced to an oil under vacuum and isolated as a white solid after purification on silica. M+1=261.

3-(2-Amino-propyl)-benzonitrile: A solution of [2-(3-Cyano-phenyl)-1-methyl-ethyl]-carbamic acid tert-butyl ester (180 mg, 0.69 mmol) in dichloromethane (5 mL) and trifluoroacetic acid (5 mL) was stirred for 15 min at room temperature. Solvents removed under vacuum, and residue was partitioned between dichloromethane and 1 N sodium hydroxide. Organic dried over magnesium sulfate and reduced to an oil under vacuum. M+1=161.

{2-[3-(Benzhydrylidene-amino)-phenyl]-1-methyl-ethyl}-carbamic acid tert-butyl ester: A suspension of [2-(3-bromo-phenyl)-1-methyl-ethyl]-carbamic acid tert-butyl ester (750 mg, 2.39 mmol), benzophenone imine (0.44 mL, 2.63 mmol), sodium tert-butoxide (298 mg, 3.1 mmol), bis(diphenylphosphino)-1,1'-binaphthyl (45 mg, 0.07 mmol), palladium acetate (16 mg, 0.07 mmol), and toluene (7.5 mL) was heated to reflux for 3 h while stirring under an atmosphere of nitrogen. Reaction diluted with ether and organics washed with water and saturated sodium chloride. Product isolated as a viscous yellow oil after purification on silica. M+1=415.

3-(2-Amino-propyl)-phenylamine: A solution {2-[3(Benzhydrylidene-amino)-phenyl]-1-methyl-ethyl}-carbamic acid tert-butyl ester (200 mg, 0.48 mmol) in dichloromethane (5 mL) and trifluoroacetic acid (5 mL) was stirred for 45 min at room temperature. Solvents removed under vacuum and residue suspended in 5 N hydrochloric acid at 60° C. for 20 min. Biphasic system washed with ether and organics discarded. The pH of the aqueous layer was then adjusted to 14 with 10 N sodium hydroxide. Aqueous was then washed three times with dichloromethane (10 mL). Combined organics dried over magnesium sulfate, and product isolated as an amber film after removal of solvent under vacuum. M+1=151.

3-(2-Nitro-propenyl)-benzoic acid methyl ester: To a 250 mL round bottom flask was added 3-formyl-benzoic acid methyl ester (2.20 g, 13.4 mmol), ammonium acetate (1.03 g, 13.4 mmol), and nitroethane (60 mL). Mixture heated to reflux under an atmosphere of nitrogen while stirring for 1.5 h. Solvent removed under vacuum then residue partitioned between ethyl acetate (100 mL) and 5% sodium bicarbonate. Organic washed with saturated sodium chloride, dried with magnesium sulfate, then concentrated to a oil under vacuum. Product purified on silica and isolated as a yellow solid. $^1$H NMR (CDCl$_3$) s (3H, 2.47 ppm), s (3H, 3.96 ppmm), t (1H, 7.55 ppm), d (2H, 7.61 ppm) m (3H, 8.09 ppm).

[3-(2-Amino-propyl)-phenyl]-methanol: To a stirring suspension of lithium aluminum hydride (90 mL of 1 M in tetrahydrofuran (THF), 90 mmol) at 0° C. under an atmosphere of nitrogen was added a solution of 3-(2-nitro-propenyl)-benzoic acid methyl ester (2.03 g, 9.2 mmol) in THF was added dropwise via an addition funnel over the course of 75 min.

Reaction warmed to room temperature overnight, chilled to 0° C., then a saturated solution of potassium sodium tartrate tetrahydrate added to the reaction dropwise. Once a cake formed, the organic phase was removed and reduced to an oil under vacuum. This residue was then dissolved in dichloromethane and dried over magnesium sulfate. Product purified on silica and isolated as a colorless oil. M+1=166.

9-{2-[2-(3-Hydroxymethyl-phenyl)-1-methyl-ethylamino]-pyrimidin-4-yl}-2-phenyl-6,7,8,9-tetrahydro-pyrimido[1,2-a]pyrimidin-4-one: A mixture of 9-(2-methanesulfonyl-pyrimidin -4-yl)-2-phenyl-6,7,8,9-tetrahydro-pyrimido[1,2-a]pyrimidin-4-one (344 mg, 0.90 mmol), [3-(2-amino-propyl)-phenyl]-methanol (371 mg, 2.25 mmol), and N-methylmorpholine (8 mL) was heated to 100° C. for 20 h. Reaction was diluted with dichloromethane (15 mL) and ethyl acetate (40 mL), washed three times with water (50 mL) then saturated sodium chloride (10 mL). Organic dried over magnesium sulfate then concentrated to a oil under vacuum. Product purified on silica and isolated as a white solid. M+1=469.

9-{2-[2-(3-Azidomethyl-phenyl)-1-methyl-ethylamino]-pyrimidin-4-yl }-2phenyl -6,7,8,9-tetrahydro-pyrimido[1,2-a]pyrimidin-4-one: To a stirring mixture of 9-{2-[2-(3-hydroxymethyl-phenyl) -1-methyl-ethylamino]-pyrimidin-4-yl}-2-phenyl-6,7,8,9-tetrahydro -pyrimido[1,2-a]pyrimidin-4-one (230 mg, 0.49 mmol), 1,8-diazabicyclo[5.4.0]undec-7-ene (0.13 mL, 0.88 mmol), and tetrahydrofuran (12 mL) at 0° C. under an atmosphere of nitrogen was added diphenylphosphoryl azide (0.19 mL, 0.88 mmol). Mixture stirred overnight warming to room temperature. Solvent removed under vacuum and product isolated as a white solid after purification on silica. M+1=494.

9-{2-[2-(3-Aminomethyl-phenyl)-1-methyl-ethylamino]-pyrimidin-4-yl}-2-phenyl -6,7,8,9-tetrahydro-pyrimido[1,2-a]pyrimidin-4-one: To a nitrogen filled vessel containing a stirring solution of 9-{2-[2-(3-azidomethyl-phenyl)-1-methyl -ethylamino]-pyrimidin-4-yl}-2-phenyl-6,7,8,9-tetrahydro-pyrimido[1,2-a]pyrimidin-4-one (190 mg, 0.39 mmol) in methanol (25 mL) was added 10% palladium on carbon (20 mg). Mixture stirred over an atmosphere of hydrogen. After 2 h, reaction filtered through a bed of Celite and solvent removed under vacuum. Residue purified on silica and isolated as a white solid.

M+1=468. $^1$NMR (CDCl$_3$) d (3H, 1.21 ppm), q (2H, 2.22 ppm), dd (1H, 2.77 ppm), dd (1H, 2.98 ppm), s (2H, 3.85 ppm), m (4H, 4.12 ppm), q (1H, 4.30 ppm), d (4.96 ppm), s (1H, 6.60 ppm), d (1H, 7.0 ppm), d (2H, 7.18 ppm), d (1H, 7.21 ppm), m(1H, 7.27 ppm), m (3H, 7.44 ppm), m (2H, 7.90 ppm), d (1H, 8.17 ppm).

9-(2-{2-[3-(Isopropylamino-methyl)-phenyl]-1-methyl -ethylamino}-pyrimidin-4-yl) -2-phenyl -6,7,8,9-tetrahydro-pyrimido[1,2-a]pyrimidin-4-one: A solution of 9-{2-[2-(3-Aminomethyl-phenyl) -1-methyl-ethylamino]-pyrimidin-4-yl}-2-phenyl-6,7,8,9-tetrahydro -pyrimido[1,2-a]pyrimidin-4-one (79 mg, 0.17 mmol) and acetone (0.015 mL, 0.21 mmol) was stirred for 10 min prior to adding sodium borohydride (108 mg, 3.4 mmol). After 10 min, solvent removed under vacuum and residue partitioned between dichloromethane (10 mL) and saturated sodium chloride. Product isolated as a white solid after purification on silica. M+1=509.

Resolution of R/S Enantiomers:

9-{2-[2-(3-Aminomethyl-phenyl)-1(S)-methyl-ethylamino]-pyrimidin-4-yl}-2-phenyl-6,7,8,9-tetrahydro-pyrimido[1,2-a]pyrimidin-4-one and 9-{2-[2-(3-aminomethyl-phenyl) -1(R)-methyl-ethylamino]-pyrimidin-4-yl}-2-phenyl-6,7,8,9-tetrahydro -pyrimido[1,2-a]pyrimidin-4-one: a sample of 9-{2-[2-(3-aminomethyl-phenyl) -1-methyl-ethylamino]-pyrimidin -4-yl}-2-phenyl-6,7,8,9-tetrahydro-pyrimido[1,2-a]pyrimidin-4-one was separated via chiral HPLC employing a CHIRALPAK AS (10 μm 20×250 mm) and eluting with 0.2% diethylamine in methanol/ carbon dioxide (35:65) at 50 mL/min (120 bar). The S-enantiomer was then confirmed by comparing the retention times on the above column to that of synthetic 9-{2-[2-(3-aminomethyl-phenyl)-1(S)-methyl-ethylamino]-pyrimidin-4-yl}-2-phenyl-6,7,8,9-tetrahydro-pyrimido[1,2-a]pyrimidin-4-one utilizing synthetic schemes E and F.

Synthetic Scheme F:

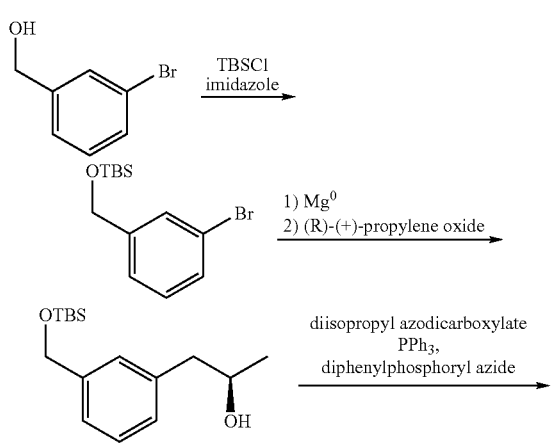

-continued

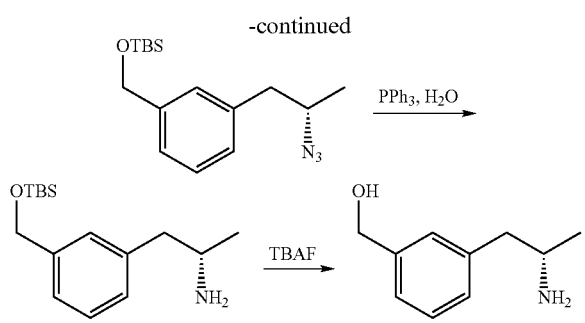

(3-Bromobenzyloxy)-tert-butyldimethylsilane: A solution 3-bromobenzyl alcohol (7.1 g, 38 mmol) and tert-butyldimethylsilyl chloride (5.7 g, 38 mmol) in N,N-dimethylformamide (40 mL) was stirred at room temperature for 5 h. Water (40 mL) was added and the mixture was extracted with hexanes. The combined extracts were washed with 10% aqueous hydrochloric acid, saturated sodium bicarbonate, saturated sodium chloride, and dried over magnesium sulfate. The desired product was isolated after concentration and purification by silica gel chromatography (hexanes). $^1$H NMR (CDCl$_3$) 7.48 (s, 1H), 7.34 (m, 1H), 7.24 (m, 2H), 4.72 (s, 2H), 0.95 (s, 9H), 0.11 (s, 6H).

1-[3-(Tert-butyldimethylsilyloxymethyl)-phenyl]-propan-2-ol: To a stirring solution of (3-bromobenzyloxy)-tert-butyldimethylsilane (7.0 g, 24 mmol) in tetrahydrofuran (100 mL) under an atmosphere of nitrogen was added magnesium turnings (0.73 g, 30 mmol) and a crystal of iodine. The mixture was heated to reflux for 1 h, cooled to 0° C. and copper (I) iodide (4.57 g, 24 mmol) was added. After stirring at 0° C. for 5 min, (R)-(+)-propylene oxide was added and the mixture was stirred for 2 h. A mixture of ammonium chloride and ammonium hydroxide (5:1, 100 mL) was added, the biphasic mixture was stirred vigorously until the copper salts dissolved, and the layers were separated. The aqueous layer was extracted with ethyl acetate, and the organic extracts were dried over magnesium sulfate and purified by flash column chromatography (ethyl acetate/hexanes). $^1$H NMR (CDCl$_3$) 7.28 (m, 1H), 7.22 (m, 1H), 7.17 (s, 1H), 7.10 (d, 1H) 4.73 (s, 2H), 4.00 (m, 1H), 2.77 (d, 1H), 2.70 (d, 1H), 1.60 (s, 1H), 1.24 (d, 3H), 0.94 (s, 9H), 0.10 (s, 6H).

[3-(2-Azidopropyl)-benzyloxy]-tert-butyldimethylsilane: To a stirring solution of 1-[3-(tert-butyldimethylsilyloxymethyl)-phenyl]-propan-2-ol (130 mg, 0.46 mmol) in THF (1.5 mL) under nitrogen at 0° C. was added diisopropyl azodicarboxylate (140 mg, 0.7 mmol), triphenylphosphine (180 mg, 0.7 mmol), and diphenylphosphoryl azide (190 mg, 0.7 mmol) and the mixture was stirred at 0° C. for 15 min. The mixture was diluted with dichloromethane, washed with water, brine, dried over magnesium sulfate, and purified by flash column chromatography (ethyl acetate/hexanes). $^1$H NMR (CDCl$_3$) 7.27 (m, 1H), 7.2 (m, 1H), 7.16 (s, 1H), 7.08 (m, 1H), 4.74 (s, 2H), 3.65 (m, 1H), 2.82 (dd, 1H), 2.73 (dd, 1H), 1.25 (d, 3H), 0.94 (s, 9H), 0.10 (s, 6H).

2-[3(Tert-butyldimethylsilyloxymethyl)-phenyl]-1-methyl-ethylamine: To a stirring solution of [3-(2-azidopropyl)-benzyloxy]-tert-butyldimethylsilane (100 mg, 0.33 mmol) in THF (1 mL) and water (0.3 mL) at 0° C. was added triphenylphosphine (128 mg, 0.5 mmol) and the solution was stirred with warming to room temperature overnight. The mixture was concentrated under vacuum and purified by flash column chromatography (NH$_3$—MeOH/CH$_2$Cl$_2$). M+1=280.

[3-2-Aminopropyl)-phenyl]-methanol: To a stirring solution of 2-[3(tert-butyldimethylsilyloxymethyl)-phenyl]-1-methyl-ethylamine (730 mg, 2.6 mmol) in tetrahydrofuran (2 mL) was added tetrabutylammonium fluoride (3.1 mmol) and the mixture was stirred at room temperature for 2 h. The solvent was removed under vacuum and the product was obtained after flash column chromatography (NH$_3$—MeOH/CH$_2$Cl$_2$). $^1$H NMR (CDCl$_3$) 7.30 (m, 1H), 7.26 (m, 1H), 7.19 (s, 1H), 7.10 (d, 1H), 4.67 (s, 2H), 3.61 (m, 1H), 2.71 (d, 1H), 2.51 (d, 1H), 1.67 (br s, 3H), 1.12 (d, 3H).

The examples in the following table were prepared using the above methods, as indicated, using the appropriately substituted oxopropionic acid derivative from scheme A and the appropriate amine to replace the phenethylamine, if desired:

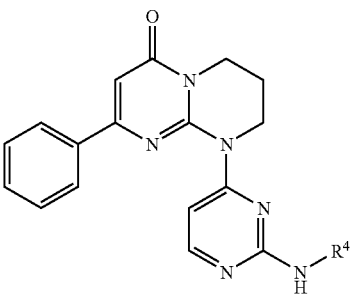

| Example | R$^4$ | Synthetic Method | HPLC RT (method) | MS M + 1 |
|---|---|---|---|---|
| 19 | 1-(3-(N-methyl-N-isopropyl-aminophenyl))-prop-2-yl | A, D, E | N/A | 510 |
| 20 | -ethyl-2-ol | A | N/A | 365 |
| 21 | -ethyl-2-morpholino | A | 5.04 (A) | 434 |
| 22 | -propyl-2-methyl | A | 6.62 (A) | 377 |
| 23 | -ethyl-2-methoxy | A | 5.81 (A) | 379 |
| 24 | -ethyl-1(S)-methyl-2-ol | A | 5.56 (A) | 379 |
| 25 | -ethyl-1(S)-isopropyl-2-ol | A | 6.45 (A) | 421 |
| 26 | -ethyl-2-phenoxy | A | 6.86 (A) | 441 |
| 27 | -propyl-2,2-dimethyl-3-dimethylamino | A | 5.24 (A) | 434 |
| 28 | -ethyl-2-aminophenyl | A | 6.16 (A) | 440 |
| 29 | -benzyl | A | 6.70 (A) | 411 |
| 30 | -propyl-3-phenyl | A | 7.04 (A) | 439 |
| 31 | -propyl-2(S)-amino-3-phenyl | A | 5.56 (A) | 454 |
| 32 | -ethyl-2-(2-chlorophenyl) | A | 6.97 (A) | 459 |
| 33 | -ethyl-2-(2-methoxyphenyl) | A | 6.84 (A) | 455 |
| 34 | -ethyl-2-(4-methoxyphenyl) | A | 6.68 (A) | 455 |
| 35 | -ethyl-2-(4-methylphenyl) | A | 6.99 (A) | 439 |
| 36 | -ethyl-2-(4-hydroxyphenyl) | A | 6.05 (A) | 441 |
| 37 | -ethyl-2-(3,4-dimethylphenyl) | A | 7.19 (A) | 453 |
| 38 | -hydrogen | A | 5.26 (A) | 321 |
| 39 | -ethyl-2-phenyl-2-ol | A | 6.20 (A) | 441 |
| 40 | -ethyl-2-keto-2-phenyl | A | N/A | 439 |
| 41 | -propyl-1-phenyl | A | N/A | 439 |
| 42 | -ethyl-1-amido-2-phenyl | A | N/A | 468 |
| 43 | -ethyl-1(S)methyl-2-phenyl | A | 6.66 (A) | 439 |
| 44 | -ethyl-1-methyl-2-(3-methylaminophenyl) | A, D, E | 5.44 (A) | 468 |

-continued
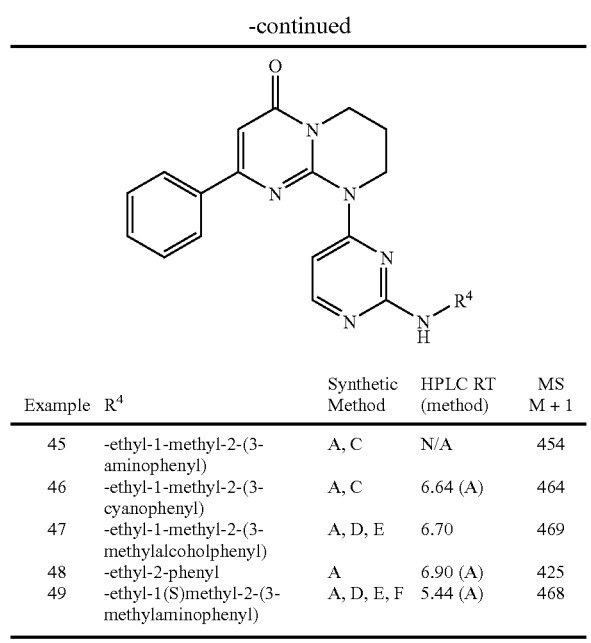
| Example | R[4] | Synthetic Method | HPLC RT (method) | MS M + 1 |
|---|---|---|---|---|
| 45 | -ethyl-1-methyl-2-(3-aminophenyl) | A, C | N/A | 454 |
| 46 | -ethyl-1-methyl-2-(3-cyanophenyl) | A, C | 6.64 (A) | 464 |
| 47 | -ethyl-1-methyl-2-(3-methylalcoholphenyl) | A, D, E | 6.70 | 469 |
| 48 | -ethyl-2-phenyl | A | 6.90 (A) | 425 |
| 49 | -ethyl-1(S)methyl-2-(3-methylaminophenyl) | A, D, E, F | 5.44 (A) | 468 |
Synthetic Scheme G:
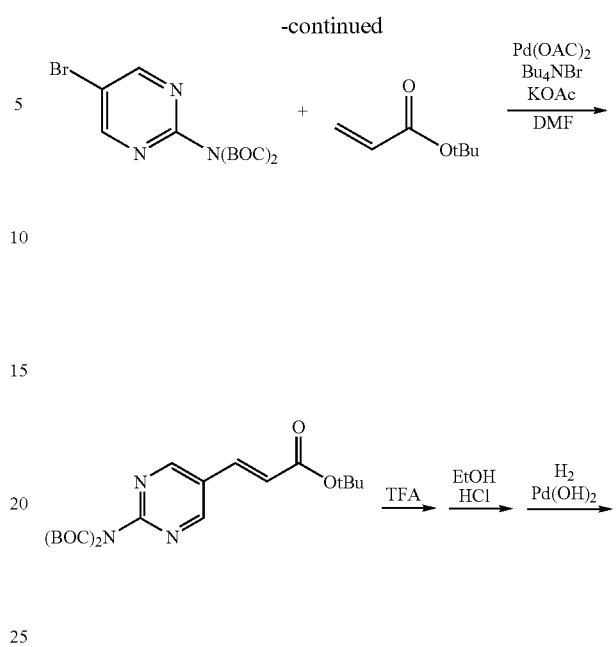
Synthetic Scheme H:
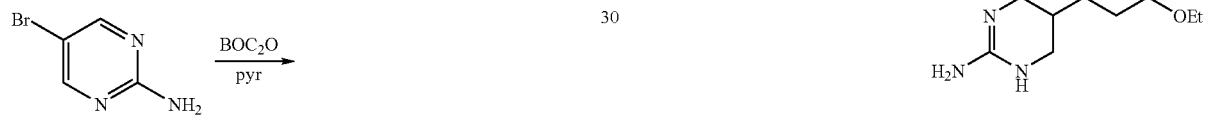
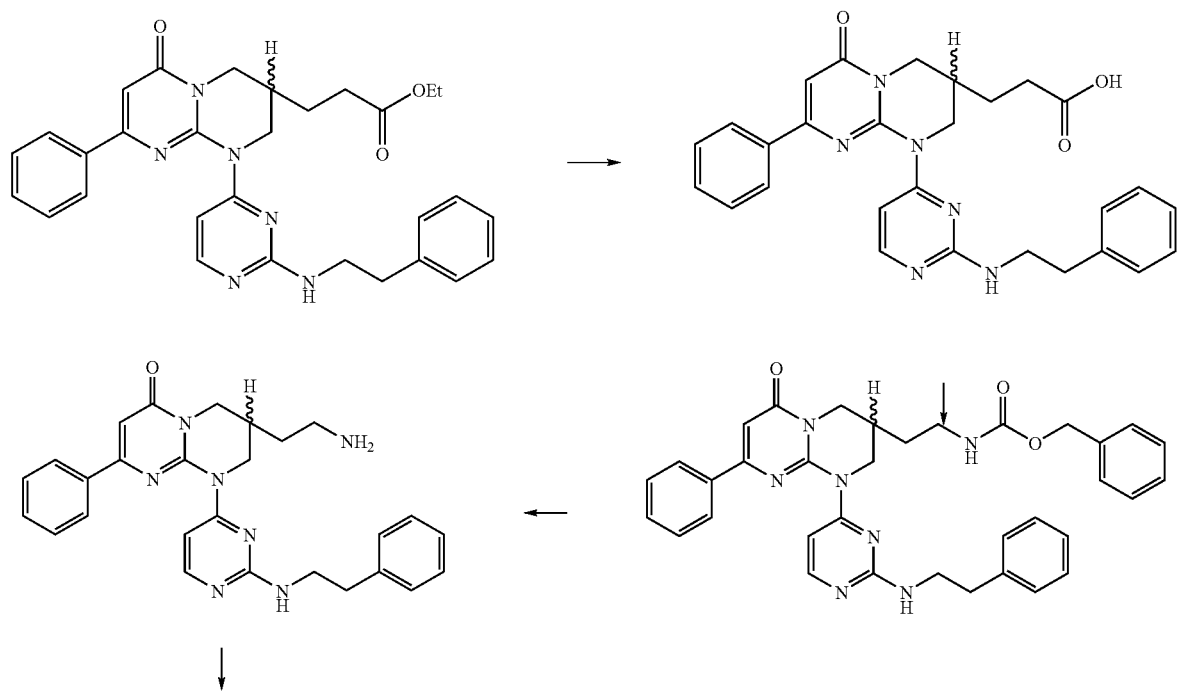

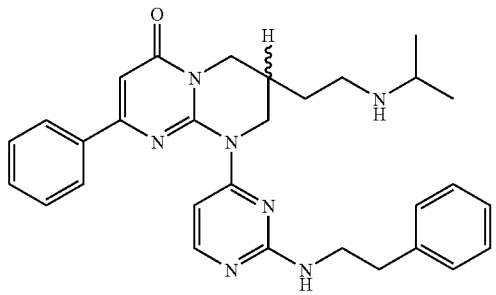

EXAMPLE 50

(5-Bromo-pyrimidin-2-yl)-bis-carbamic acid tert-butyl ester: A suspension of 5-bromo-pyrimidin-2-ylamine (10.2 g, 58.6 mmol), di-tert-butyldicarbonate (28.1 g, 129 mmol), and pyridine (100 mL) was heated to 70° C. overnight while stirring under an atmosphere of nitrogen. Solvent removed under vacuum, then residue was partitioned between diethyl ether and 5% potassium dihydrogenphosphate. Organic washed with saturated ammonium chloride then dried over magnesium sulfate. Partial evaporation of ether under vacuum produced a white solid which then was collected by filtration. M+1=374/376.

3-(2-bis-tert-Butoxycarbonylamino-pyrimidin-5-yl)-acrylic acid tert-butyl ester: A mixture of (5-bromo-pyrimidin-2-yl)-bis-carbamic acid tert-butyl ester (5.0 g, 13.4 mmol), tert-butylacrylate (3.9 mL, 26.7 mmol), potassium acetate (3.9 g, 40.2 mmol), tetrabutylammonium bromide (4.3g, 13.4 mmol), palladium acetate (150 mg, 0.7 mmol), and N-N'-dimethylformamide (50 mL) was stirred at 70° C. for 1 h. Solvent removed under vacuum, and residue partitioned between ether (200 mL) and water. Organic washed further with water and saturated ammonium chloride then dried over magnesium sulfate. Product isolated as a yellow solid after purification on silica. M+1=422.

3-(2-Amino-1,4,5,6-tetrahydro-pyrimidin-5-yl)-propionic acid ethyl ester hydrochloride salt: A solution of 3-(2-bis-tert-butoxycarbonylamino-pyrimidin-5-yl)-acrylic acid tert-butyl ester (3.0 g, 7.1 mmol) in dichloromethane (20 mL) and trifluoroacetic acid (50 mL) was stirred at room temperature for 2 h. Solvents removed under vacuum and resulting solid suspended in 2 M hydrochloric acid in diethyl ether (25 mL) and in ethanol (75 mL). Palladium hydroxide on carbon (20%) added to the nitrogen filled flask and stirred for 3 days under a hydrogen atmosphere of hydrogen delivered via balloon. Reaction mixture filtered through a bed of Celite, and filtrate concentrated to an amber oil under vacuum. M+1=200.

3-[6-Oxo-1-(2-phenethylamino-pyrimidin-4-yl)-8-phenyl-1,3,4,6-tetrahydro-2H-pyrimido[1,2-a]pyrimidin-3-yl]-propionic acid: A solution of 3-[6-oxo-1-(2-phenethylamino-pyrimidin-4-yl)-8-phenyl-1,3,4,6-tetrahydro-2H-pyrimido[1,2-a]pyrimidin-3-yl]-propionic acid ethyl ester (240 mg, 0.46 mmol), 10% aqueous lithium hydroxide (0.2 mL), and tetrahydrofuran (5 mL) was heated to 50° C. Reaction partitioned between dichloromethane (50 mL) and 5% sodium dihydrogenphosphate. Organic dried over magnesium sulfate, then concentrated to a white solid under vacuum. M+1=497.

{2-[6-Oxo-1-(2-phenethylamino-pyrimidin-4-yl)-8-phenyl-1,3,4,6-tetrahydro-2H-pyrimido[1,2-a]pyrimidin-3-yl]-ethyl}-carbamic acid benzyl ester: A suspension of 3-[6-Oxo-1-(2-phenethylamino-pyrimidin-4-yl)-8-phenyl -1,3,4,6-tetrahydro -2H-pyrimido[1,2-a]pyrimidin-3-yl]-propionic acid (218 mg, 0.44 mmol), diphenylphosphoryl azide (0.095 mL, 0.44 mmol), N—N'-diisopropylethyl amine (0.077 mL, 0.44 mmol), and toluene (5 mL) was heated to reflux for 1 h. Benzyl alcohol (0.091, 0.88 mmol) added to reaction and continued to reflux for an additional 6 h. After removal of solvent under vacuum, product isolated as a white solid after purification on silica. M+1=602.

7-(2-Amino-ethyl)-9-(2-phenethylamino-pyrimidin-4-yl)-2-phenyl-6,7,8,9-tetrahydro-pyrimido[1,2-a]pyrimidin-4-one: A solution of {2-[6-Oxo-1-(2-phenethylamino-pyrimidin-4-yl)-8-phenyl-1,3,4,6-tetrahydro-2H-pyrimido[1,2-a]pyrimidin-3-yl]-ethyl}-carbamic acid benzyl ester (100 mg, 0.17 mmol), dichloromethane (5 mL) and methanol (15 mL) was added 10% palladium on carbon (5 mg) and stirred at room temperature over an atmosphere of hydrogen overnight. Reaction filtered through a bed of Celite, and solvent removed under vacuum to afford a white solid. M+1=468.

7-(2-Isopropylamino-ethyl)-9-(2-phenethylamino-pyrimidin-4-yl) -2-phenyl-6,7,8,9-tetrahydro-pyrimido[1,2-a]pyrimidin-4-one: To a solution of 7-(2-Amino-ethyl)-9-(2-phenethylamino-pyrimidin-4-yl)-2-phenyl-6,7,8,9-tetrahydro-pyrimido[1,2-a]pyrimidin-4-one (70 mg, 0.15 mmol), acetone (0.02 mL), dichloromethane (0.5 mL) and methanol (0.5 mL) was added sodium triacetoxyborohydride (38 mg, 0.18 mmol) Reaction stirred for 2 h at room temperature. Solvents removed under vacuum. Residue partitioned between dichloromethane and 5% sodium bicarbonate. Organics purified on silica to afford a white solid. M+1=510. $^1$NMR (CDCl$_3$) d (6H, 1.17 ppm), m (2H, 1.68 ppm), m (1H, 2.32 ppm), m (3H, 2.78 ppm), t (2H, 2.94 ppm), m (1H, 3.55 ppm), dd (2H, 3.70 ppm), d (1H, 4.40 ppm), dd (1H, 4.53 ppm), m (1H, 5.10 ppm), s (1H, 6.60 ppm), m (3H, 7.24 ppm), m (2H, 7.32 ppm), m (3H, 7.44 ppm), m (2H, 7.90 ppm) d (1H, 8.18 ppm).

The examples in the following table were prepared using the above methods, as indicated, using the appropriate substituted alkene to replace the tert-butylacrylate, if desired:

| Example | R³ | Synthetic Method | HPLC RT (method) | MS M + 1 |
|---|---|---|---|---|
| 50 | -ethyl-2-amino(N-isopropyl) | A, G, H | 6.00 (B) | 510 |
| 51 | -ethyl-2-amino | A, G, H | 5.57 (A) | 468 |
| 52 | -ethyl-2-carbamic acid benzyl ester | A, G, H | 7.38 (A) | 602 |
| 53 | -ethyl-2-amino(N-benzyl) | A, G, H | 6.17 (A) | 558 |
| 54 | -propionic acid ethyl ester | A, G, H | 7.27 (A) | 525 |
| 55 | -propionic acid | A, G, H | 7.50 (B) | 497 |

| Example | R⁴ | Synthetic Method | HPLC RT (method) | MS M + 1 |
|---|---|---|---|---|
| 56 | -ethyl-1(S)-phenyl | A | 6.42 (A) | 385 |
| 57 | -ethyl-2-phenyl | A | 6.34 (A) | 385 |
| 58 | -propyl-2-methyl | A | 6.00 (A) | 337 |

Synthetic Scheme I:

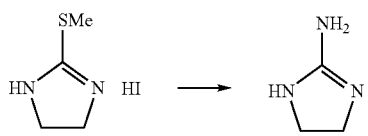

EXAMPLE 59

4,5-Dihydro-1H-imidazol-2-ylamine hydroiodic acid: Suspension of 2-methylsulfanyl-4,5-dihydro-1H-imidazole hydroiodic acid (3.0 g, 12.3 mmol) and 2M ammonia in methanol (20 mL) heated to 90° C. in a sealed tube overnight. Solvents removed under vacuum to afford a white solid. M+1=86.

| Example | R¹ | R² | R³ | Synthetic Method | MS M + 1 |
|---|---|---|---|---|---|
| 59 | -phenyl | H | 1-(3-hydroxymethyl-phenyl)prop-2-yl | A, D, H | 454 |

HPLC Method A: 5-95% acetonitrile (0.1% trifluoroacetic acid) in 10 min @1 mL/min on Agilent Zorbax Exlipse XDB C-8 (4.6×150 mm 5 µm).

HPLC Method B: 5-95% acetonitrile (0.1% trifluoroacetic acid) in 14 min @1 mL/min on LunaC-18(4.6×150 mm 5 µm).

Synthetic Scheme J:

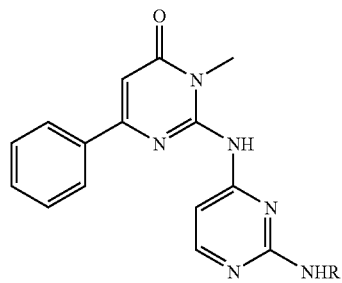

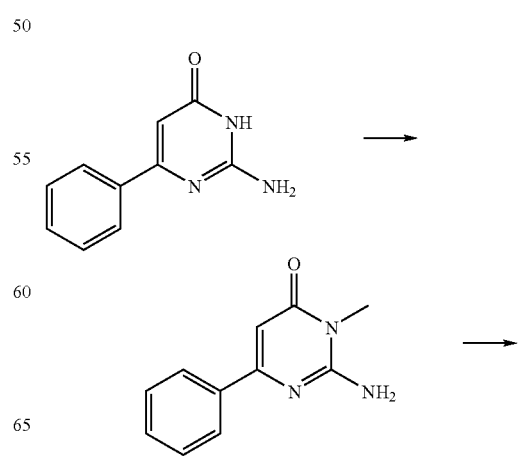

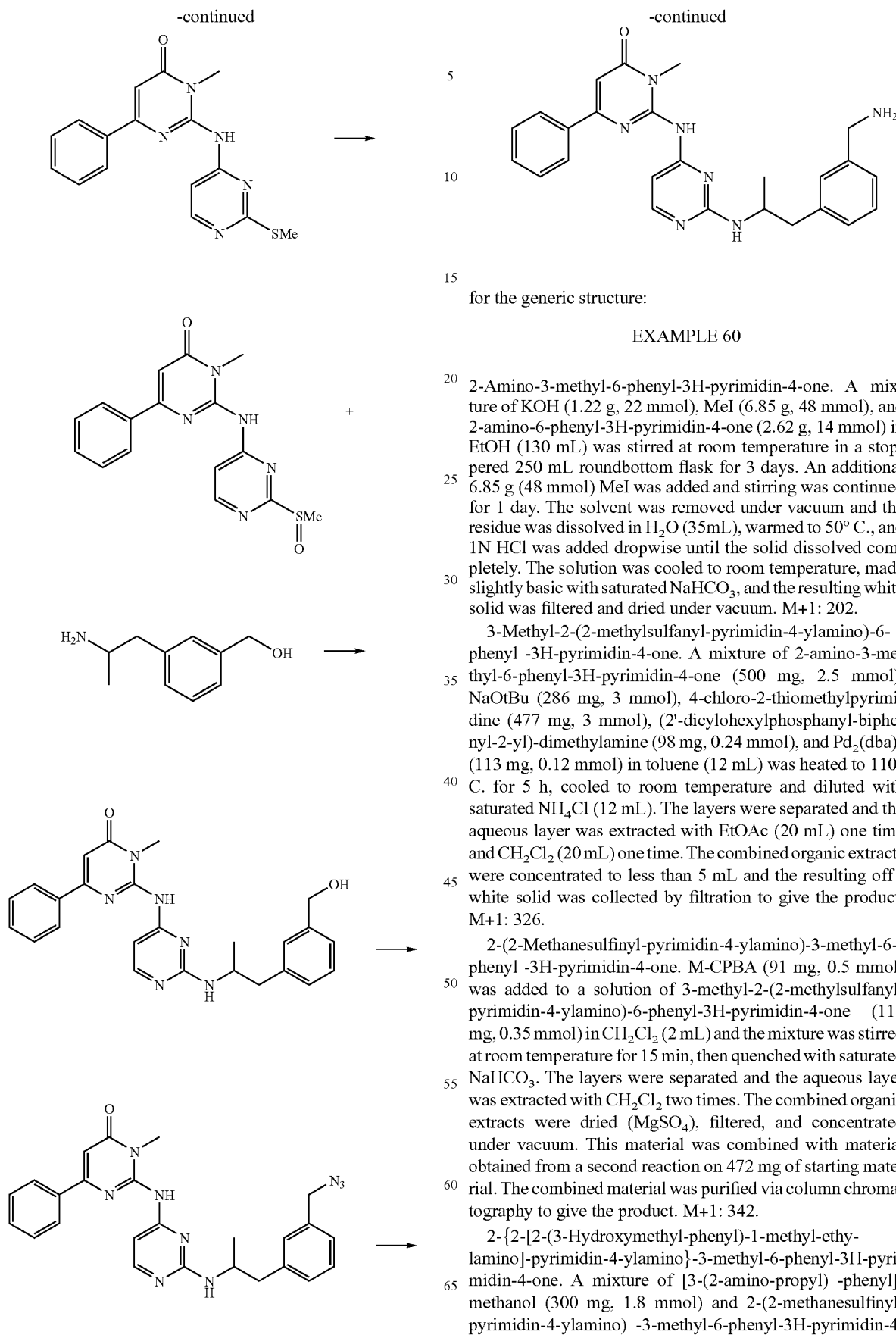

for the generic structure:

EXAMPLE 60

2-Amino-3-methyl-6-phenyl-3H-pyrimidin-4-one. A mixture of KOH (1.22 g, 22 mmol), MeI (6.85 g, 48 mmol), and 2-amino-6-phenyl-3H-pyrimidin-4-one (2.62 g, 14 mmol) in EtOH (130 mL) was stirred at room temperature in a stoppered 250 mL roundbottom flask for 3 days. An additional 6.85 g (48 mmol) MeI was added and stirring was continued for 1 day. The solvent was removed under vacuum and the residue was dissolved in $H_2O$ (35mL), warmed to 50° C., and 1N HCl was added dropwise until the solid dissolved completely. The solution was cooled to room temperature, made slightly basic with saturated $NaHCO_3$, and the resulting white solid was filtered and dried under vacuum. M+1: 202.

3-Methyl-2-(2-methylsulfanyl-pyrimidin-4-ylamino)-6-phenyl -3H-pyrimidin-4-one. A mixture of 2-amino-3-methyl-6-phenyl-3H-pyrimidin-4-one (500 mg, 2.5 mmol), NaOtBu (286 mg, 3 mmol), 4-chloro-2-thiomethylpyrimidine (477 mg, 3 mmol), (2'-dicylohexylphosphanyl-biphenyl-2-yl)-dimethylamine (98 mg, 0.24 mmol), and $Pd_2(dba)_3$ (113 mg, 0.12 mmol) in toluene (12 mL) was heated to 110° C. for 5 h, cooled to room temperature and diluted with saturated $NH_4Cl$ (12 mL). The layers were separated and the aqueous layer was extracted with EtOAc (20 mL) one time and $CH_2Cl_2$ (20 mL) one time. The combined organic extracts were concentrated to less than 5 mL and the resulting off-white solid was collected by filtration to give the product. M+1: 326.

2-(2-Methanesulfinyl-pyrimidin-4-ylamino)-3-methyl-6-phenyl -3H-pyrimidin-4-one. M-CPBA (91 mg, 0.5 mmol) was added to a solution of 3-methyl-2-(2-methylsulfanyl-pyrimidin-4-ylamino)-6-phenyl-3H-pyrimidin-4-one (115 mg, 0.35 mmol) in $CH_2Cl_2$ (2 mL) and the mixture was stirred at room temperature for 15 min, then quenched with saturated $NaHCO_3$. The layers were separated and the aqueous layer was extracted with $CH_2Cl_2$ two times. The combined organic extracts were dried ($MgSO_4$), filtered, and concentrated under vacuum. This material was combined with material obtained from a second reaction on 472 mg of starting material. The combined material was purified via column chromatography to give the product. M+1: 342.

2-{2-[2-(3-Hydroxymethyl-phenyl)-1-methyl-ethylamino]-pyrimidin-4-ylamino}-3-methyl-6-phenyl-3H-pyrimidin-4-one. A mixture of [3-(2-amino-propyl) -phenyl]-methanol (300 mg, 1.8 mmol) and 2-(2-methanesulfinyl-pyrimidin-4-ylamino) -3-methyl-6-phenyl-3H-pyrimidin-4- one (300 mg, 0.9 mmol) in NMP (8 mL) was heated to 100° C. for 16 h. The reaction was cooled to room temperature and EtOAc was added. The mixture was then washed with H₂O three times, brine once, dried (MgSO₄), filtered, concentrated under vacuum, and purified by preparative-scale TLC to give the product. M+1: 443.

2-{2-[2-(3-Azidomethyl-phenyl)-1-ethylamino]-pyrimidin 4-ylamino}-3-methyl-6-phenyl-3H-pyrimidin-4-one. A mixture of diphenylphosphoryl azide (237 mg, 0.86 mmol), 1,8-diazabicylco[5.4.0]undec-7-ene (130 mg, 0.86 mmol), and 2-{2-[2-(3-hydroxymethyl-phenyl) -1-methyl-ethylamino]-pyrimidin-4-ylamino}-3-methyl-6-phenyl-3Hpyrimidin-4-one (190 mg, 0.43mmol) in THF (3.5 mL) was stirred at 35° C. for 17.5 h. The mixture was cooled to room temperature, diluted with H₂O, and extracted with CH₂Cl₂ three times. The combined extracts were dried (MgSO₄), filtered, concentrated under vacuum, and purified by column chromatography to give the product. M+1: 468.

2-{-[2-(3-Aminomethyl-phenyl)-1-methyl-ethylamino]-pyrimidine -4-ylamino}-3-methyl-6-phenyl-3H-pyrimidin-4-one. A mixture of Zn° powder (60 mg, 0.9 mmol), NH₄Cl (49 mg, 0.9 mmol), and 2-{2-[2-(3-azidomethyl-phenyl) -1-ethylamino]-pyrimidin -4-ylamino}-3-methyl-6-phenyl-3H-pyrimidin-4-one (216 mg, 0.46 mmol) in a mixture of H₂O (2 mL) and EtOH (2 mL) was heated to reflux for 2 h and cooled to room temperature. The mixture was partitioned between H₂O and 4:1 CHCl₃/IPA, the layers were separated and the aqueous layer was extracted with 4:1 CHCl₃/IPA three times. The extracts were dried (MgSO₄), filtered, concentrated, and purified by preparative-scale TLC (30 mg, 15%). ¹H NMR (400 MHz, CDCl3): 8.14 (d, J 4, 1H), 7.68 (s, 2H), 7.53 (m, 1H), 7.45 (m, 2H), 7.19 (m, 1H), 7.13 (d, J 16, 1H), 7.04 (s, 1H), 6.95 (s, 1H), 6.40 (br s, 1H), 6.10 (br s, 1H), 4.62 (br s, 1H), 4.18 (br s, 1H), 3.78 (s, 2H), 3.61 (s, 3H), 2.74 (br s, 2H), 1.11 (d, J 6, 3H). M+1: 442.

EXAMPLE 61

1-(2-{2-[4-(1-Amino-ethyl)-phenyl]-ethylamino}-pyrimidin-4-yl)-8-phenyl -1,23,6-tetrahydro-pyrimido[1,2-a]pyrimidin-4-one:

Synthetic Scheme K:

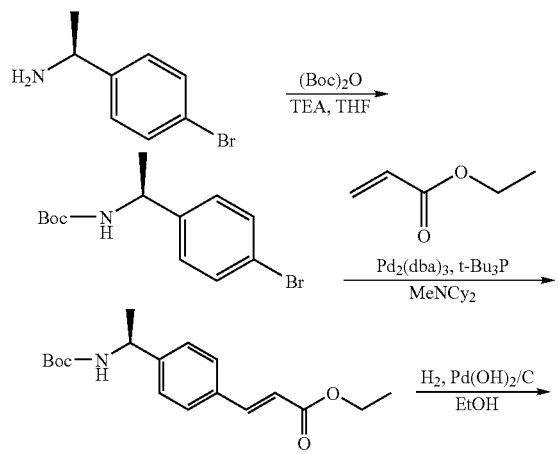

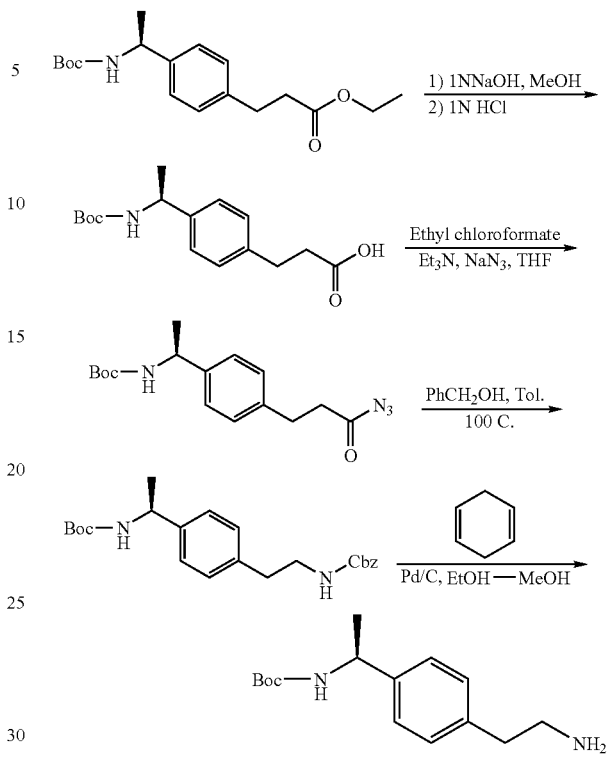

1-(4-Bromo-phenyl)-ethyl]-carbamic acid ester: A mixture of 1-(4-bromo-phenyl)-ethylamine (7.0 g, 35 mmol), di-tert-butyldicarbonate (35 mL, 1.0 M in THF), and triethylamine (4.9 mL, 35 mmol) in THF (140 mL) was stirred at room temperature for 17 h. The mixture was washed with saturated NH₄Cl, brine, dried over magnesium sulfate and concentrated to afford a white solid as the desired product. M+1=300.

3-[4-(1-tert-Butoxycarbonylamino-ethyl)-phenyl]-acrylic acid ethyl ester: To a mixture of [1-(4-bromo-phenyl)-ethyl]-carbamic acid tert-butyl ester (3.0 g, 10 mmol), tris(dibenzylideneacetone)dipalladium (0.55 g, 0.6 mmol), and N -methyldicyclohexylamine (2.1 mL, 10 mmol) was purged nitrogen followed by the addition of 1,4-dioxane (20 mL) and tri-tert-butylphospine (0.24 g, 1.2 mmol). The mixture was again purged with nitrogen and the ethyl acrylate (2.16 mL, 20 mmol) was added. The mixture was heated to 80° C. for 30 min, poured into water (100 mL) and extracted with ethyl acetate (150 mL). The organic layer was separated, washed again with water, dried over magnesium sulfate, concentrated and chromatographed on silica gel using 2:1 hexanes/ethyl acetate to afford a light-brown oil. M+1=320.

3-[4-(1-tert-Butoxycarbonylamino-ethyl)-phenyl]-propionic acid ethyl ester: Through a mixture of 3-[4-(1-tert-butoxycarbonylamino-ethyl)-phenyl]-acrylic acid ethyl ester (0.22 g, 0.69 mmol) and palladium hydroxide on carbon (100 mg) in ethanol (10 mL) was bubbled hydrogen through a balloon for 17 h. The mixture was filtered through celite and concentrated to afford an off-white solid. M+1=322.

3-[4-(tert-Butoxycarbonylamino-ethyl)-phenyl]-propionic acid: The mixture of 3-[4-(1-tert-butoxyarbonylamino-ethyl)-phenyl]-propionic acid ethyl ester (8.69 g, 27 mmol) and 1 N sodium hydroxide (135 mL, 135 mmol) in methanol (50 mL) was heated to reflux for 1 h, brought to room temperature and concentrated. The residue obtained was dissolved in ethyl acetate (50 mL) and the mixture was acidified to a pH 6-5 with 1N hydrochloric acid. The organic phase was separated and concentrated to afford an off-white solid. M+1=294.

{1-[4-(2-Azidocarbonyl-ethyl)-phenyl]-ethyl}-carbamix acid tert -butyl ester: To a mixture of 3-[4-(1-tert-butoxycarbonylamino-ethyl)-phenyl]-propionic acid (1.0 g, 3.4 mmol) in dry THF (10 mL) at 0° C. was added triethylamine (0.8 mL). After 30 min, ethyl chloroformate was added dropwise. The mixture was stirred at 0° C. for 1 h then, sodium azide (0.24 g, 3.74 mmol) in water (2 mL) was added dropwise. The ice-bath was removed and the mixture was stirred at room temperature for 1.5 h. The mixture was diluted with ethyl acetate (100 mL), washed with saturated sodium bicarbonate, brine, dried over magnesium sulfate and concentrated to afford a white solid. M+1=319.

{1-[4-(2-Benzyloxycarbonylamino-ethyl)-phenyl]-ethyl}carbamic acid tert-butyl ester: The mixture of {1-[4-(2-azidocarbonyl-ethyl)-phenyl]-ethyl}-carbamic acid tert-butyl ester (2.2 g, 6.92 mmol) and benzyl alcohol (1.0 mL, 10.4 mmol) in toluene (20 mL) was heated to 105° C. for 17 h. The mixture was brought to room temperature and a white solid crashed out which corresponded to the desired product. This solid was filtered off, washed with toluene and dried under high vacuum. M+1=399.

{1-[4-(2-Amino-ethyl)-phenyl]-ethyl}-carbamic acid tert-butyl ester: The mixture of {1-[4-(2-benzyloxycarbonylamino-ethyl)-phenyl]-ethyl}carbamic acid tert-butyl ester (0.80 g, 2.0 mmol), 1,4-cyclohexadiene (0.96 mL, 10 mmol) and palladium on carbon (100 mg) in ethanol (20 mL)-methanol (5 mL) was heated to reflux for 2 h and brought to room temperature. The mixture was filtered through celite and concentrated to afford a white solid. M+1=265.

Synthetic Scheme L:

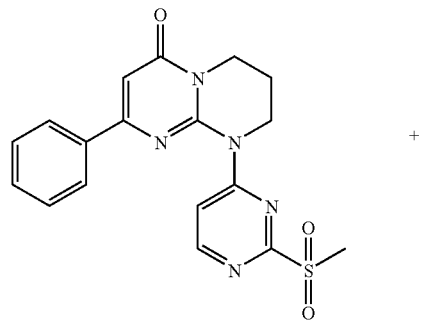

+

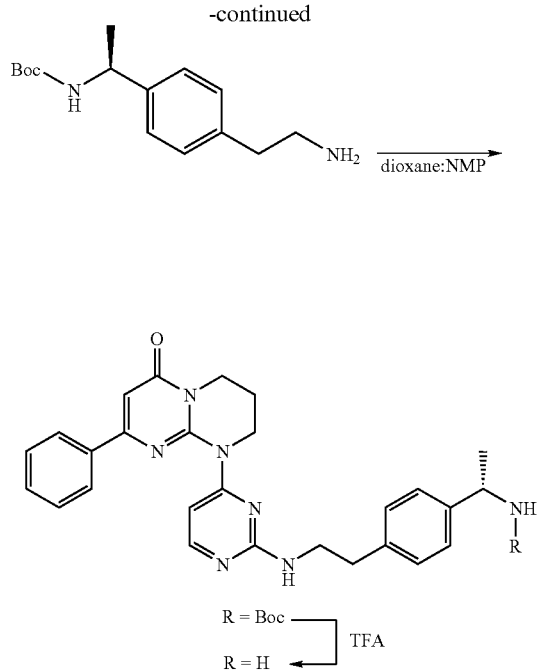

[1-(4-{2-[4-(4-Oxo-8-phenyl-3,4-dihydro -2H,6H-pyrimido[1,2-a]pyrimidin-1-yl)-pyrimidin -2-ylamino]ethyl}-phenyl)-ethyl]-carbamic acid tert-butyl ester: The mixture of 1-(2-methanesulfonyl-pyrimidin-4-yl)-8-phenyl-1,2,3,6-tetrahydro -pyrimido[1,2-a]pyrimidin-4-one (0.20 g, 053 mmol) and {1-[4-(2-amino -ethyl)-phenyl]-ethyl}-carbamic acid tert-butyl ester (0.304 g, 0.79 mmol) in 1:1 dioxane: 1-methyl -2-pyrrolidinone (6 mL) was heated to 100° C. for 17 h. The mixture was partitioned between water (10 mL) and ethyl acetate (20 mL). The organic phase was separated, washed with water, saturated sodium bicarbonate, brine, dried over magnesium sulfate and chromatographed on silica gel using 0-4% MeOH/$CH_2Cl_2$ to afford a white solid. M+1=568.

1-(2-{2-[4-(1-Amino-ethyl)-phenyl]-ethylamino}-pyrimidin-4-yl)-8-phenyl -1,23,6-tetrahydro-pyrimido[1,2-a]pyrimidin-4-one: The mixture of [1-(4-{2-[4-(4-oxo-8-phenyl) - 3,4-dihydro-2H,6H-pyrimido[1,2-a]pyrimidin-1-yl)-pyrimidin -2-ylamino]ethyl}-phenyl)-ethyl]-carbamic acid tert-butyl ester (0.24 g, 0.42 mmol) and trifluoroacetic acid (0.7 mL, 20 mmol) in dichloromethane (5 mL) was stirred at room temperature for 1.5 h. The mixture was washed with saturated sodium bicarbonate, brine, dried over magnesium sulfate, concentrated and chromatographed on silica gel using 0-8% 2M $NH_3MeOH/CH_2Cl_2$ to afford a white solid. M+1=468.
$^1$NMR (DMSO) d (3H, 1.21 ppm), m (2H, 2.15 ppm), t (2H, 2.83 ppm), d (1H, 3.18 ppm), b (2H, 3.49 ppm), m (6H, 4.13 ppm), s (1H, 6.62 ppm), d (2H, 7.09 ppm), d (2H, 7.16 ppm), d (2H, 7.27 ppm), m (3H, 7.46 ppm), dd (2H, 7.96 ppm), b (1H, 8.18 ppm).

EXAMPLE 62

1-(2-{2[4-(1-Isopropylamino-ethyl)-phenyl]-ethylamino}-pyrimidin-4-yl)-8-phenyl-1,2,3,6-tetrahydro-pyrimido[1,2-a]pyrimidin-4-one Synthetic Scheme M:

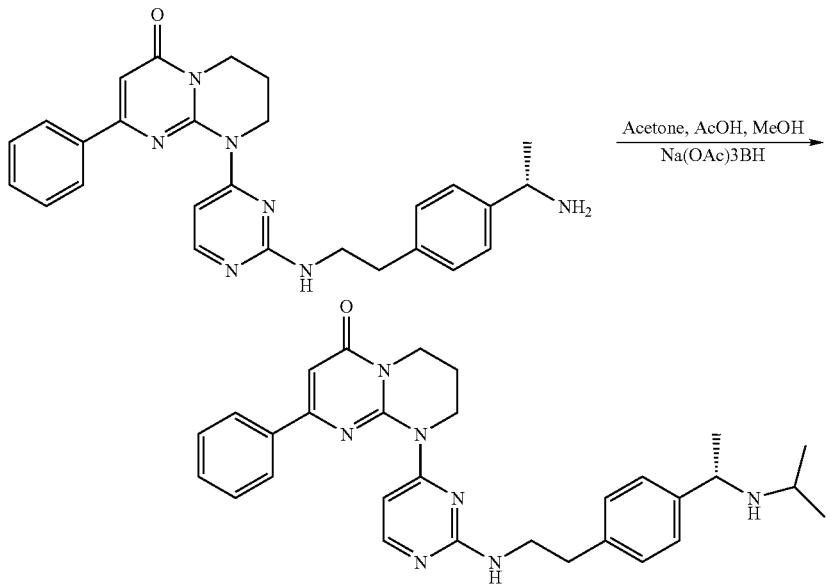

1-(2-{2[4-(1-Isopropylamino-ethyl)-phenyl]-ethylamino}-pyrimidin-4-yl)-8-phenyl-1,2,3,6-tetrahydro-pyrimido[1,2-a]pyrimidin-4-one: The mixture of 1-(2-{2-[4-(1-amino-ethyl)-phenyl]-ethylamino}-pyrimidin -4-yl)-8-phenyl-1,23,6-tetrahydro-pyrimido[1,2-a]pyrimidin-4-one (70 mg, 0.15 mmol), sodium triacetoxyborohydride (0.13 g, 0.60 mmol), acetone (5 mL) and acetic acid (0.5 mL) in methanol (10 mL) was stirred at room temperature for 17 h. The mixture was concentrated and the residue was dissolved in $CH_2Cl_2$ (50 mL), washed with saturated sodium bicarbonate, brine, dried over magnesium sulfate and concentrated to afford a white solid. M+1=510. $^1$H NMR (DMSO) dd (6H, 0.92 ppm), d (3H, 1.19 ppm), m (2H, 2.14 ppm), m (1H, 2.44 ppm), t (2H, 2.82 ppm), b (2H, 3.48 ppm), m (1H, 3.77 ppm), m (4H, 4.03 ppm), s (1H, 6.62 ppm), d (2H, 7.08 ppm), d (2H, 7.16 ppm), d (2H, 7.24 ppm), m (3H, 7.46 ppm), dd (2H, 7.96 ppm), b (1H, 8.18 ppm).

EXAMPLE 63

1-{2-[2-(4-Aminomethyl-phenyl)-1-methyl-ethylamino]-pyrimidin-4-yl}-8-phenyl -1,2,3,6-tetrahydro-pyrimido[1,2-a]pyrimidin-4-one Synthetic Scheme N:

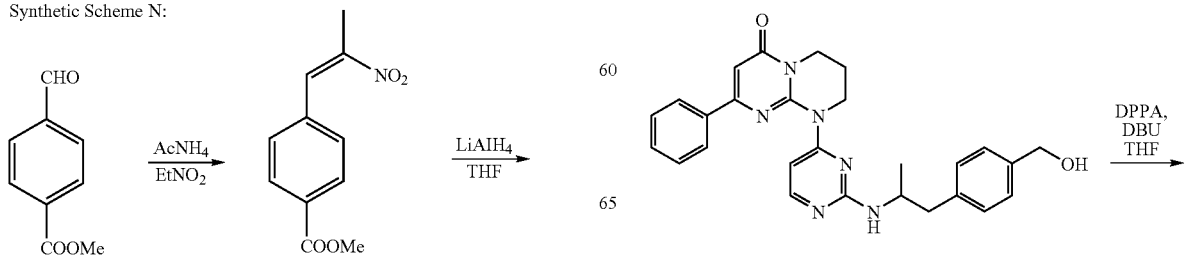

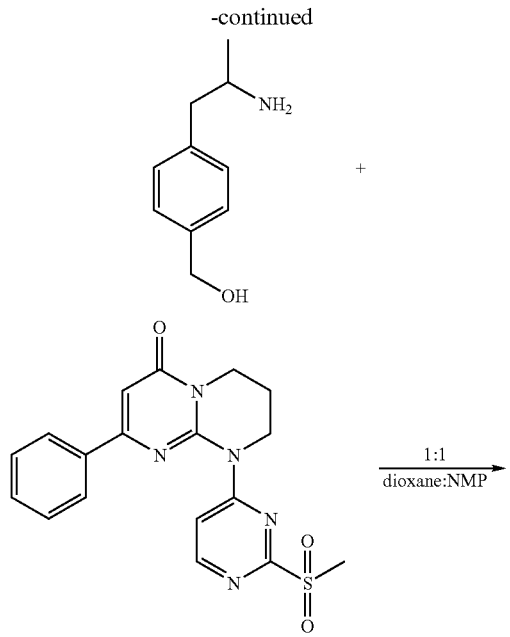

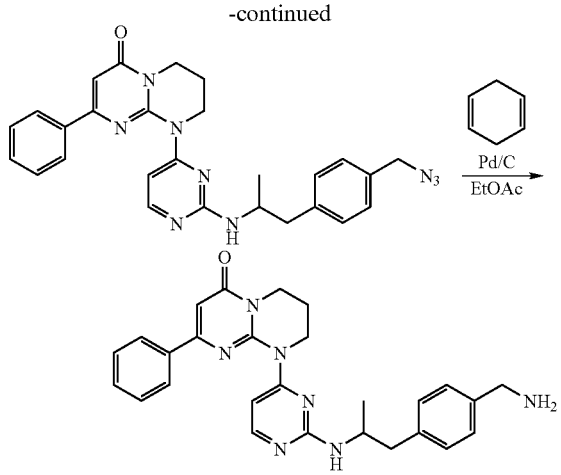

4-(2-Nitro-propenyl)-benzoic acid methyl ester: The mixture of 4-formyl-benzoic acid methylester (20.1 g, 122.4 mmol), ammonium acetate (9.4 g, 122.4 mmol) in nitroethane (200 mL) was heated to reflux for 2.5 h. The mixture was brought to room temperature and concentrated. The residue was partitioned between water (200 mL) and ethylacetate (500 mL). The organic layer was separated, washed with saturated sodium bicarbonate, brine, dried over magnesium sulfate, concentrated and chromatographed on silica gel using 6:1 hexanes/ethylacetate to afford a yellow solid. M+1=222.

[4-(2-Amino-propyl-phenyl]-methanol: The suspension of lithium aluminumhyride (11 g, 277 mmol) in THF (200 mL) was brought to 0° C. followed by the slowly addition of 4-(2-nitro-propenyl)-benzoic acid methyl ester (12.25 g, 55.4 mmol) in THF (100 mL). Once the addition was completed, the mixture was stirred at 0° C. for 15 min and brought to room temperature and stirred for 17 h. The mixture was brought to 0° C. and quenched with solid sodium sulfate decahydrate until stopped bubbling. The suspension was filtered and the filtrate was concentrated and the yellow oil obtained was chromatographed on silica gel using 0-8% 2M $NH_3$ $MeOH/CH_2Cl_2$. M+1=166.

1-{2-[2-(4-Hydroxymethyl-phenyl)-1-methyl-ethylamino]-pyrimidin-4-yl}-8-phenyl-1,2,3,6-tetrahydro-pyrimido[1,2-a]pyrimidin-4-one: 1-(2-methanesulfonyl-pyrimidin-4-yl)-8-phenyl-1,2,3,6-tetrahydro-pyrimido[1,2-a]pyrimidin-4-one (1.1 g, 2.9 mmol) and [4-(2-amino-propyl)-phenyl]-methanol (0.96 g, 5.8 mmol) in 1:1 dioxane: 1-methyl-2-pyrrolidinone (16 mL) was heated to 100° C. for 20 h. The mixture was partitioned between water (30 mL) and ethyl acetate (60 mL). The organic phase was separated, washed with water, saturated sodium bicarbonate, brine, dried over magnesium sulfate and chromatographed on silica gel using 0-8% 2M $NH_3$ $MeOH/CH_2Cl_2$ to afford a white solid. M+1=469. $^1$NMR ($CDCl_3$) d (3H, 1.21 ppm), s (1H, 1.79 ppm), m (2H, 2.22 ppm), m(1H, 2.79 ppm), m (1H, 2.98 ppm), m (4H, 4.11 ppm), m (1H, 4.13 ppm), b(3H, 4.68 ppm), s (1H, 6.60 ppm), d (2H, 7.21 ppm), d (3H, 7.29 ppm), m (3H, 7.44 ppm), dd (2H, 7.91 ppm), d (1H, 8.17 ppm).

1-{2-[2-(4-Azidomethyl-phenyl)-1-methyl-ethylamino]-pyrimidin-4-yl}-8-phenyl-1,2,3,6-tetrahydro-pyrimido[1,2-a]pyrimidin-4-one: The mixture of 1-{2-[2-(4-hydroxymethyl-phenyl)-1-methyl-ethylamino]-pyrimidin-4-yl}-8-phenyl-1,2,3,6-tetrahydro-pyrimido[1,2-a]pyrimidin-4-one (0.11 g, 0.24 mmol) and 1,8-diaza-bicyclo[5.4.0]undec-7-ene (47 µL, 0.312 mmol) in tetrahydrofuran (5 mL) was brought to 0° C. followed by the addition of diphenylphosphoryl azide (68 µL, 0.312 mmol). The mixture was removed from the ice-bath and stirred at room temperature for 17 h. The mixture was concentrated and chromatographed on silica gel using 0-8% 2M $NH_3$ $MeOH/CH_2Cl_2$ to afford a white solid. M+1=494.

1-{2-[2-(4-Aminomethyl-phenyl)-1-methyl-ethylamino]-pyrimidin-4-yl}-8-phenyl-1,2,3,6-tetrahydro-pyrimido[1,2-a]pyrimidin-4-one: The mixture of 1-{2-[2-(4-azidomethyl-phenyl)-1-methyl-ethylamino]-pyrimidin-4-yl}-8-phenyl-1,2,3,6-tetrahydro-pyrimido[1,2-a]pyrimidin-4-one, 1,4-cyclohexadiene (80 µL, 0.80 mmol) and palladium on carbon (100 mg) in ethylacetate (10 mL) was heated to reflux for 3 h and brought to room temperature. The mixture was filtered through celite and concentrated to afford a white solid. M+1=468. $^1$NMR ($CDCl_3$) d (3H, 1.22 ppm), m (2H, 2.23 ppm), m (1H, 2.76 ppm), m (1H, 2.98 ppm), s (2H, 3.84 ppm), m (4H, 4.11 ppm), m (1H, 4.31 ppm), d (1H, 4.95 ppm), s (1H, 6.60 ppm), d (2H, 7.21 ppm), d (3H, 7.23 ppm), m (3H, 7.44 ppm), dd (2H, 7.91 ppm), d (1H, 8.18 ppm).

EXAMPLE 64

1-(2-{2-[4-(2-Amino-propyl)-phenyl]-1-methyl-ethylamino}-pyrimidin-4-yl)-8-phenyl-1,2,3,6-tetrahydro-pyrimido[1,2-a]pyrimidin-4-one Synthetic Scheme O:

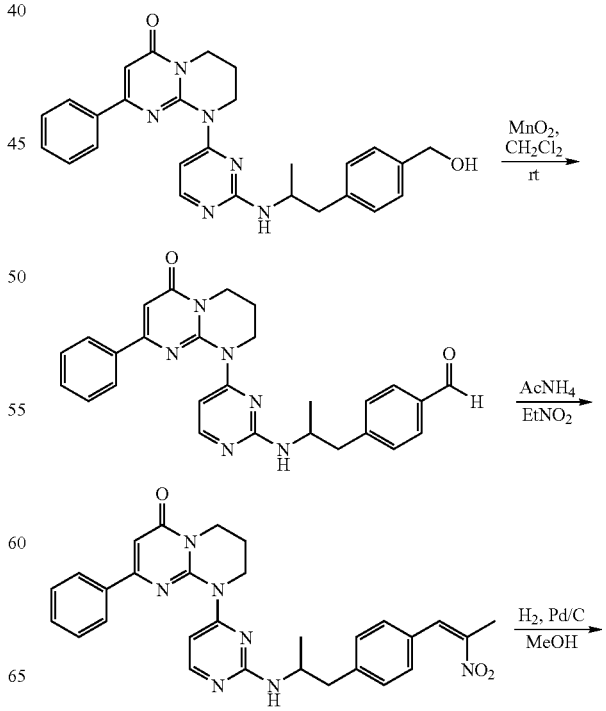

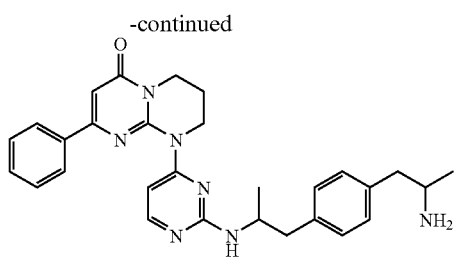

4-{2-[4-(4-Oxo-8-phenyl-3,4-dihydro-2H,6H-pyrimido[1,2-a]pyrimidin-1-yl)-pyrimidin-2-ylamino]-propyl}-benzaldehyde: The mixture of 1-{2-[2-(4-hydroxymethyl-phenyl)-1-methyl-ethylamino]-pyrimidin-4-yl}-8-phenyl-1,2,3,6-tetrahydro-pyrimido[1,2-a]pyrimidin-4-one (0.38 g, 0.81 mmol) and manganese dioxide (3.5 g, 40.5 mmol) in dichloromethane was stirred at room temperature for 3 h. The mixture was filtered off and concentrated to afford a white solid. M+1=467.

1-(2-{1-Methyl-2-[4-(2-nitro-propenyl)-phenyl]-ethylamino}-pyrimidin-4-yl)-8-phenyl-1,2,3,6-tetrahydro-pyrimido[1,2-a]pyrimidin-4-one: The mixture of 4-{2-[4-(4-oxo-8-phenyl-3,4-dihydro-2H,6H-pyrimido[1,2-a]pyrimidin-1-yl)-pyrimidin-2-ylamino]-propyl}-benzaldehyde (35 mg, 0.08 mmol), ammonium acetate (10 mg, 0.16 mmol) in nitroethane (5 mL) was heated to reflux for 4 h. The mixture was brought to room temperature and concentrated. The residue was dissolved in ethylacetate (20 mL), washed with water, saturated sodium bicarbonate, brine, dried over magnesium sulfate and concentrated. M+1=524.

1-(2-{2-[4-(2-Amino-propyl)-phenyl]-1-methyl-ethylamino}-pyrimidin-4-yl)-8-phenyl-1,2,3,6-tetrahydro-pyrimido[1,2-a]pyrimidin-4-one: Through a mixture of 1-(2-{1-methyl-2-[4-(2-nitro-propenyl)-phenyl]-ethylamino}-pyrimidin-4-yl)-8-phenyl-1,2,3,6-tetrahydro-pyrimido[1,2-a]pyrimidin-4-one (10 mg, 0.02 mmol) and palladium on carbon (cat) in methanol was bubbled hydrogen through a balloon for 17 h. The mixure was filtered through celite, concentrated and chromatographed on silica gel using 0-4% MeOH/CH$_2$Cl$_2$ to afford an off-white solid. M+1=496. $^1$NMR (CDCl$_3$) d (3H, 1.28 ppm), d (3H, 1.79 ppm), m (1H, 1.86 ppm), m (2H, 2.22 ppm), m (1H, 2.80 ppm), m (1H, 2.94 ppm), m (3H, 3.75 ppm), m (4H, 4.15 ppm), m (1H, 4.30 ppm), s (1H, 6.60 ppm), d (3H, 7.15 ppm), d (2H, 7.22 ppm), m (3H, 7.44 ppm), dd (2H, 7.91 ppm), d (1H, 8.17 ppm).

EXAMPLE 65

1-(2-{2-[3-(1-Amino-1-methyl-ethyl)-phenyl]-1-methyl-ethylamino}-pyrimidin-4-yl)-8-phenyl-1,2,3,6-tetrahydro-pyrimido[1,2-a]pyrimidin-4-one Synthetic Scheme P:

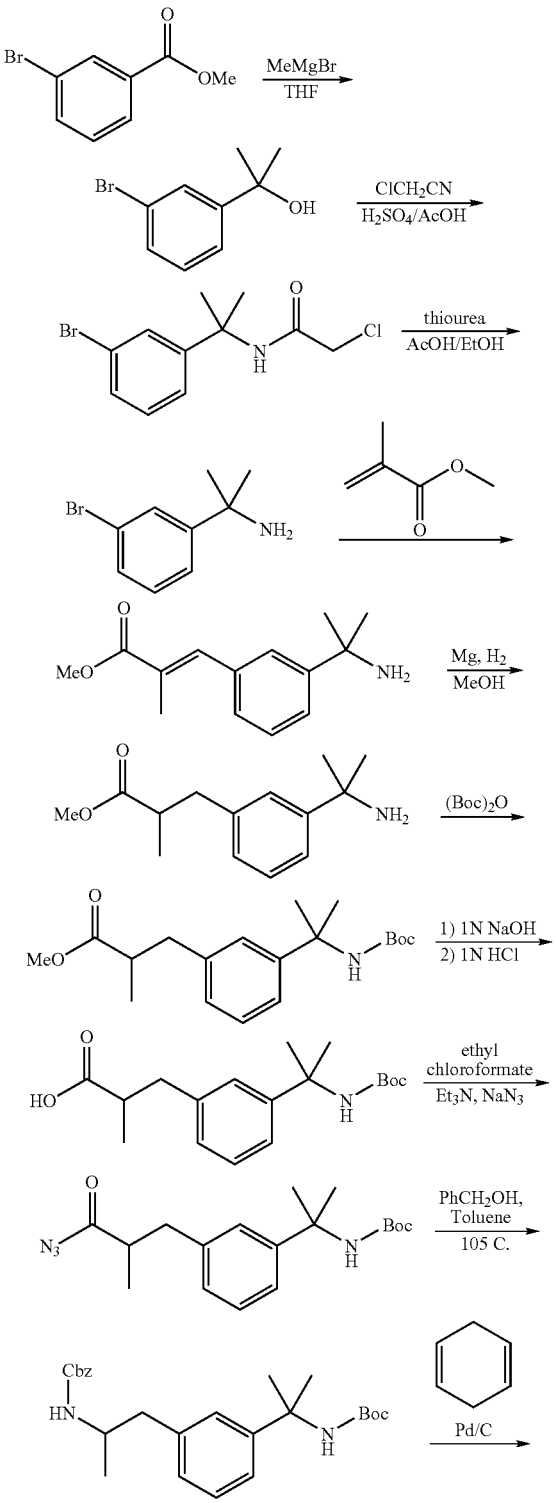

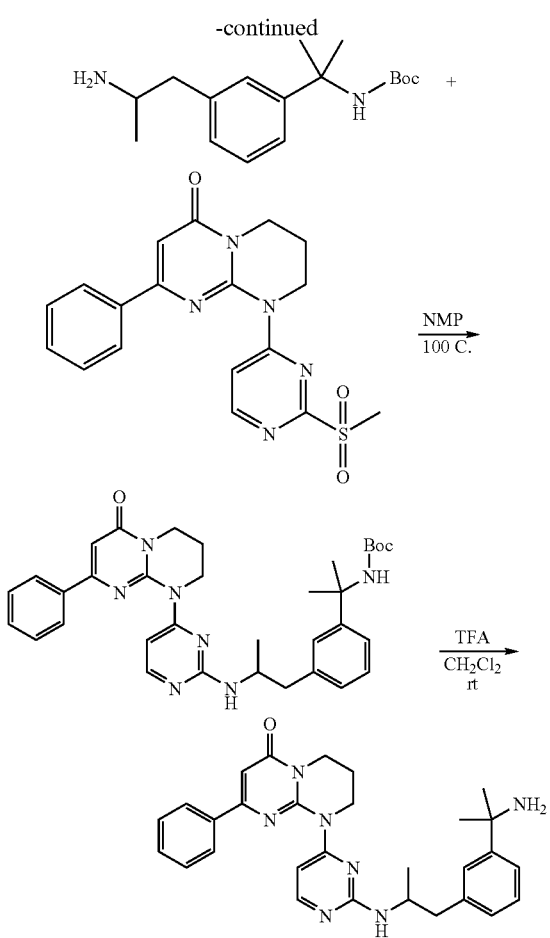

2-(3-Bromo-phenyl)-propan-2-ol: The 3-bromo-benzoic acid methyl ester (1.0 g, 4.7 mmol) in tetrahydrofuran (10 mL) was brought to −78° C. followed by the addition of methyl magnesium bromide (7.7 mL, 10.81 mmol) and warmed to room temperature and stirred for 17 h. The mixture was poured into sat $NH_4Cl$ and extracted with ethylacetate. The organic extracts were combined, washed with brine, dried over magnesium sulfate and chromatographed on silica gel using 04% methanol/dichloromethane to afford colorless oil.

N-[1-(3-Bromo-phenyl)-1-methyl-ethyl]-2-chloro-acetamide: To a mixture of the 2-(3-bromo-phenyl)-propan-2-ol and (0.76 g, 3.6 mmol) and chloro-acetonitrile (7 mL) was added acetic acid (0.6 mL) and the resulting mixture was cooled to 0° C. Concentrated sulfuric acid (0.6 mL) was added dropwise and the mixture was brought to room temperature and stirred for 17 h. Mixture was poured into ice-water (10 mL) and extracted with ethylacetate. The extracts were combined, dried over magnesium sulfate and concentrated to afford a white solid. M+1=291.

1-(3-Bromo-phenyl)-1-methyl-ethylamine: The mixture of N-[1-(3-bromo-phenyl)-1-methyl-ethyl]-2-chloro-acetamide (1.0 g, 3.5 mmol), thiourea (0.32 g, 4.2 mmol), acetic acid (1.5 mL) in ethanol (7 mL) was heated to reflux for 10 h and brought to room temperature. Water was added to the mixture until a precipitate was formed which was filtered. The filtrate was made basic pH 7-8 with 15% NaOH. The product was extracted with ethyl acetate and concentrated to afford a yellow solid. M+1=214.

3-[3-(1-Amino-1-methyl-ethyl)-phenyl]-2-methyl-acrylic acid methyl ester: The mixture of 1-(3-bromo-phenyl)-1-methyl-ethylamine (0.74 g, 3.5 mmol), tris(dibenzylideneacetone)dipalladium (0.19 g, 0.21 mmol), and N-methyldicyclohexylamine (10 mmol) was purged with nitrogen followed by the addition of 1,4-dioxane (7 mL) and tri-tert-butylphosphine (85 mg, 0.42 mmol). The mixture was again purged with nitrogen and ethyl acrylate (0.75 mL, 7.0 mmol) was added. The mixture was heated to 80° C. for 1 h, brought to room temperature, poured into water (50 mL) and extracted with ethyl acetate (100 mL). The organic layer was separated, washed again with water, dried over magnesium sulfate, concentrated and chromatographed on silica gel using 0-4% MeOHl/$CH_2Cl_2$ to afford yellow oil.

3-[3-(1-Amino-1-methyl-ethyl)-phenyl]-2-methyl-propionic acid methyl ester: The mixture of 3-[3-(1-amino-1-methyl-ethyl)-phenyl]-2-methylacrylic acid methyl ester (2.0 g, 8.6 mmol), magnesium (0.63 g, 25.8 mmol) in methanol was heated to reflux for 3 h until the starting material was consumed. The mixture was brought to room temperature, filtered and the filtrate was concentrated. The residue obtained was washed with saturated $NH_4Cl$, brine, dried over magnesium sulfate and concentrated.

3-[3-(1-tert-Butoxycarbonylamino-1-methyl-ethyl)-phenyl]-2methyl-propionic acid methyl ester: To a mixture of 3-[3-(1-amino-1-methyl-ethyl) -phenyl]-2-methyl-propionic acid methyl ester (1.17 g, 5.0 mmol) in THF was added triethylamine (1 mL) and stirred at room temperature for 15 min followed by the addition of (Boc)$_2$O and dimethylaminopropylamine (cat.). The resulting mixture was stirred at room temperature for 17 h. The mixture was poured into ethyl acetate (200 mL) and washed with saturated $NH_4Cl$, brine, dried over magnesium sulfate and chromatographed on silica gel using 0-4% methano/dichloromethane and 7% 2M $NH_3$ MeOH/$CH_2Cl_2$ to afford a yellow oil. M+1=336.

3-[3-1-tert-Butoxycarbonylamino-1-methyl-ethyl)-phenyl]-2methyl-propionic acid: A mixture of 3-[3-(1-tert-butoxycarbonylamino-1-methyl-ethyl) -phenyl]-2-methyl-propionic acid methyl ester (430 mg, 1.3 mmol) and 1 N sodium hydroxide (6.5 mL, 6.5 mmol) in methanol (10 mL) was heated to reflux for 48 h. The mixture was brought to room temperature and concentrated. The residue was dissolved in dichloromethane (20 mL) and acidified to a pH ~5 using 10% $KHSO_4$. The organic phase was separated and concentrated. M+1=322.

{1-[3-(2-Azidocarbonyl-propyl)-phenyl]-1-methyl-ethyl}-carbamic acid tert-butyl ester: To a stirred solution of 3-[3-1-tert-butoxycarbonylamino-1-methyl-ethyl)-phenyl]-2-methyl-propionic acid (0.33 g, 1.03 mmol) in dry THF (5 mL) at 0° C. was added triethylamine (0.29 mL, 2.06 mmol). After 40 min, ethyl chloroformate (0.11 mL) was added dropwise. The mixture was stirred at 0° C. for 1.5 h then, sodium azide (73 mg, 1.13 mmol) in water (0.5 mL) was added dropwise. The mixture was brought to room temperature and stirred for 1.5 h more. The resulting mixture was diluted with ethyl acetate (20 mL), washed with saturated sodium bicarbonate, brine, dried over magnesium sulfate and concentrated to afford yellow oil.

{1-[3-(2-Benzyloxycarbonylamino-propyl)-phenyl]-1-methyl -ethyl}-carbamic acid tert-butyl ester: The mixture of {1-[3-(2-azidocarbonyl-propyl)-phenyl ]-1-methyl-ethyl}-carbamic acid tert-butyl ester (0.34 g, 0.98 mmol) and benzyl alcohol (0.15 mL, 1.5 mmol) in toluene (2 mL) was heated to 105° C. for 17 h. The mixture was brought to room temperature, concentrated and chromatographed on silica gel using 0-4% MeOlUCH$_2$Cl$_2$ to afford a light yellow solid.

{1-[3-(2-Amino-propyl)-phenyl]-1-methyl-ethyl}-carbamic acid tert-butyl ester: To a mixture of {1-[3-(2-benzyloxycarbonylamino-propyl)-phenyl]-1-methyl-ethyl}-carbamic acid tert-butyl ester (0.28 g, 0.65 mmol), 1,4-cyclohexadiene (0.31 mL, 3.25 mmol) and Pd/C (cat.) in methanol was heated to reflux for 17 h. The mixture was filtered through celite and concentrated to afford light yellow oil. M+1=293.

[1-Methyl-1-(3-{2-[4-(4-oxo-8-phenyl-3,4-dihydro-2H, 6H-pyrimido[1,2-a]pyrimidin-1-yl)-pyrimidin-2-ylamino]-propyl}-phenyl)-ethyl]-carbamic acid tert-butyl ester: To a mixture of {1-[3-(2-amino-propyl)-phenyl]-1-methyl -ethyl}-carbamic acid tert-butyl ester (0.19 g, 0.65 mmol) and 1-(2-methanesulfonyl-pyrimidin-4-yl) -8-phenyl-1,2,3,6-tetrahydro-pyrimido[1,2-a]pyrimidin-4-one (0.26 g, 0.72 mmol) in NMP (2 mL) was heated to 100° C. for 17 h. The mixture was poured into water (15 mL) and extracted with ethyl acetate. The organic extracts were combined, washed with saturated sodium bicarbonate, brine, dried over magnesium sulfate and chromatographed on silica gel using 0-4% MeOH/CH$_2$Cl$_2$ to afford a light yellow oil. M+1=596.

1-(2-{2-[3-(1-Amino-1-methyl-ethyl)-phenyl]-1-methyl-ethylamino}-pyrimidin-4-yl)-8-phenyl-1,2,3,6-tetrahydro-pyrimido[1,2-a]pyrimidin-4-one: To a mixture of [1-methyl-1-(3-{2-[4-(4-oxo-8-phenyl-3,4-dihydro-2H, 6H-pyrimido[1,2-a]pyrimidin-1-yl)-pyrimidin-2-ylamino]-propyl}-phenyl)-ethyl]-carbamic acid tert-butyl ester (0.25 g, 0.42 mmol) and trifluoroacetic acid (1 mL) in dichloromethane (2 mL) was stirred at room temperature for 30 min. The mixture was washed with saturated sodium bicarbonate, brine, dried over magnesium sulfate and was purified by chromatography on silica gel using 0-8% 2 M NH$_3$ MeOH/CH$_2$Cl$_2$. M+1=496. $^1$NMR (CDCl$_3$) d (3H, 1.23 ppm), s (6H, 1.47 ppm), m (2H, 2.21 ppm), m (1H, 2.82 ppm), m (1H, 2.98 ppm), s (1H, 3.48 ppm), m (4H, 4.12 ppm), m (1H, 4.35 ppm), d (1H, 4.95 ppm), s (1H, 6.60 ppm), d (1H, 7.09 ppm), d (1H, 7.21 ppm), m (2H, 7.36 ppm), m (3H, 7.44 ppm), dd (2H, 7.91 ppm), d (1H, 8.16 ppm).

for the general structure:

Synthetic Scheme Q:

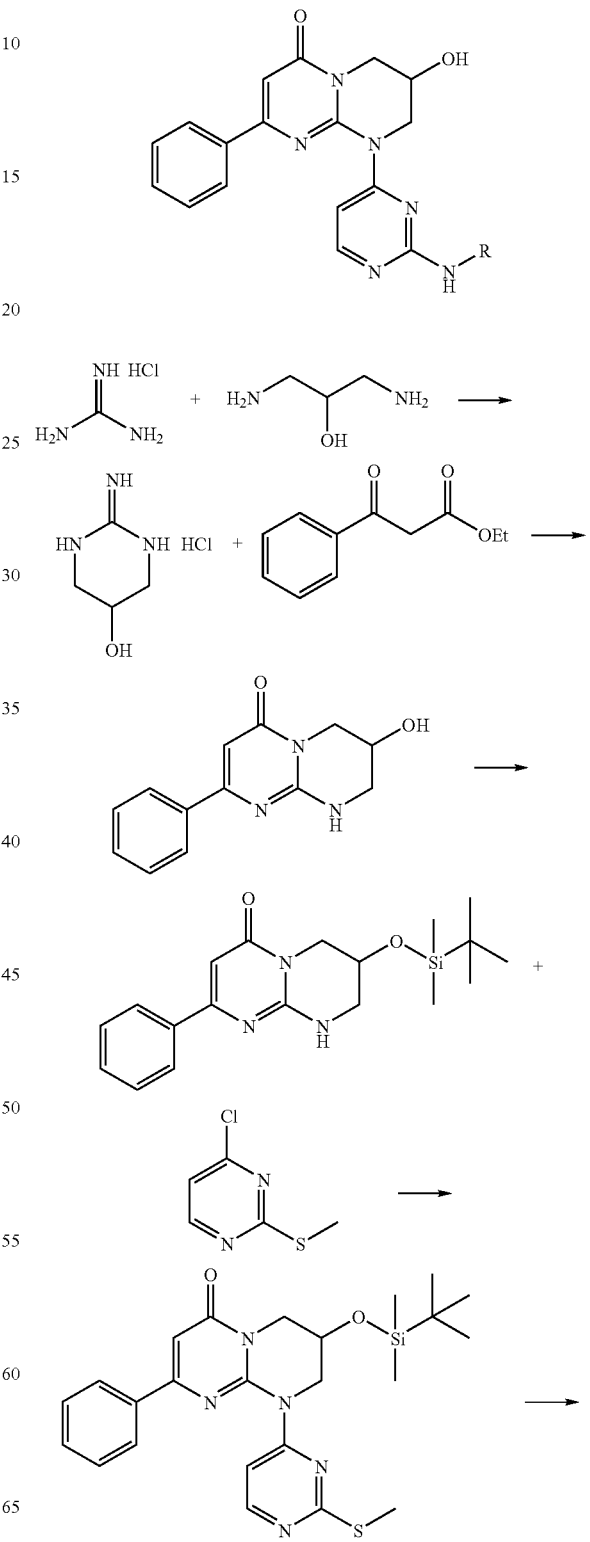

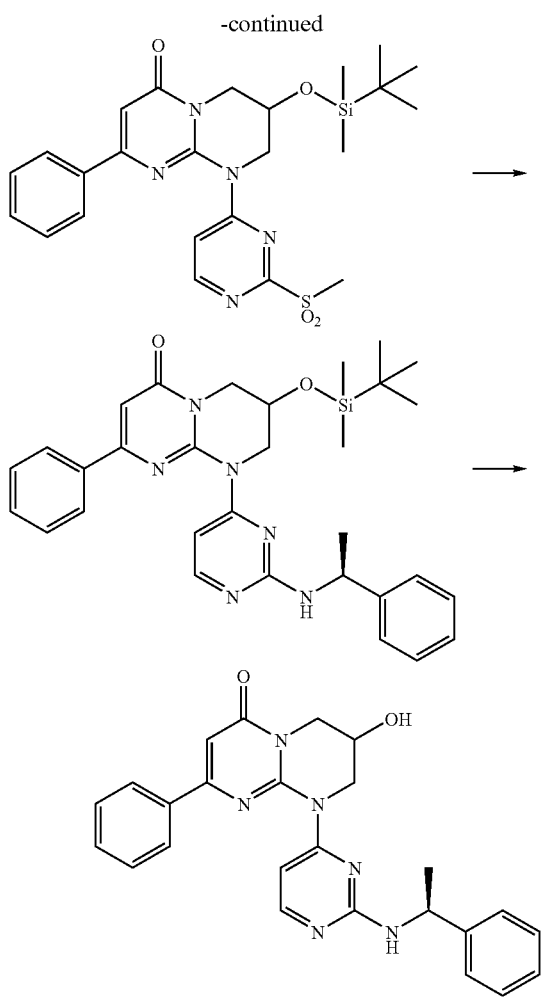

EXAMPLE 66

7-Hydroxy-2-phenyl-9-[2-(1-phenyl-ethylamino)-pyrimidin-4-yl]-6,7,8,9-tetrahydro-pyrimido[1,2-a]pyrimidin-4-one 2-Imino-hexahydro-pyrimidin-5-ol hydrochloride: A mixture of 2-hydroxy -1,3-diaminopropane (9.80 g, 108 mmol) and guanidine hydrochloride (10.4 g, 108 mmol) in a 100 mL RBF was heated at 140° C. under nitrogen for 5 h. The reaction mixture, while under vigorous stirring, was let cooled to 100° C. whereby a mixture of iPrOH (5 mL) and $CH_3CN$ (5 mL) were added, resulting in the formation of a slurry. After cooled to room temperature, the mixture was filtered and the solid was washed with additional $CH_3CN$ (total 30 mL). The solid was further dried under vacuum to yield a white solid. $^1H$ NMR (400 MHz, $D_2O$): 4.21 (m, 1 H), 3.34 (dt, J 15.2, 2.8, 2H), 3.22 (dt, J 15.2, 2.8).

7-Hydroxy-2-phenyl-6,7,8,9-tetrahydro-pyrimido[1,2-a]pyrimidin-4-one: In a 250 mL RBF with a stirrer bar, a mixture of 3-oxo-3-phenyl-propionic acid ethyl ester (15 g, 78 mmol), $K_2CO_3$ (11.0 g, 80 mmol) and 2-imino-hexahydro-pyrimidin-5-ol hydrochloride (11.8 g, 78 mmol) in EtOH (150 mL) was heated at 90° C. under nitrogen overnight. After 17 h, the mixture was cooled to room temperature, and filtered. The mother liquid was concentrated to a sludge that was then diluted with $H_2O$. The resulting slurry was filtered and the solid was washed first with MeOH, then a mixture of EtOAc-MeOH (2:1) to give the first batch of product. The solid residue from the crude reaction was washed first with $H_2O$ (3×10 mL), then MeOH, and finally a mixture of EtOAc-MeOH (2: 1) to yield a second batch of product. The combined products were the dried in air to provide a white solid. $^1H$ NMR (400 MHz, $DMSO_6$): 7.94 (m, 2 H), 7.44 (bt, J 3.2, 0.5 H), 6.10 (s, 1H), 5.35 (d, J 3.2, 0.5 H), 4.22 (m, 1 H), 4.12 (d, J 14,1H), 3.54 (dd, J 14, 2.0,1 H), 3.39 (d, 12.4, 1H), 3.18 (m, 1H). M+1: 244.

7-(tert-Butyl-dimethyl-silanyloxy)-9-(2-methylsulfanyl-pyrimidin-4-yl)-2-phenyl-6,7,8,9-tetrahydro-pyrimido[1,2-a]pyrimidin-4-one 7-(tert-Butyl-dimethyl-silanyloxy)-2-phenyl-6,7,8,9-tetrahydro-pyrimido[1,2-a]pyrimido[1,2-a]pyrimidin-4-one: A mixture of the alcohol (1.0 g, 4.1 mmol), TBDMSCl (1.3 g, 6.1 mmol), and imidazole (0.80 g, 12 mmol) in DMF (9 mL) was stirred at room temperature. After 5 h, the reaction mixture was diluted with EtOAc (50 mL). The organic was washed with $H_2O$ (3×20 mL), dried ($Na_2SO_4$) and concentrated to a solid. M+1: 358

In a 150 mL RBF with a stirrer bar, 4-chloro-2-methylsulfanyl-pyrimidine (1.0 g, 9.3 mmol) and 7-(tert-butyl-dimethyl-silanyloxy)-2-phenyl-6,7,8,9-tetrahydro-pyrimido[1, 2-a]pyrimidin-4-one (1.0 g, 2.8 mmol) were mixed in PhMe (12 mL) and dioxane (3 mL) under nitrogen. Subsequently BINAP (0.18 g, 0.28 mmol), $Pd(OAc)_2$ (0.063 g. 0.28 mmol), and NaOtBu (0.54 g, 5.6 mmol) were added. The mixture was heated to 110° C. with vigorous stirring for 4 h. After cooled to room temperature, the mixture was diluted with EtOAc (50 mL) and the resulting mixture was washed with $H_2O$, $NH_4Cl$ (sat), and dried with $Na_2SO_4$. The organic layer was concentrated and the residue was purified on silica with hexanes/EtOAc (1:1). The product was further purified via triturating with (2:1) hexanes-EtOAc to provide a white solid. $^1HNMR$ (400 MHz, $CDCl_3$): 8.37 (d, J 4, 1H), 7.91 (m, 2H), 7.71 (d, J 4, 1H), 7.46 (m, 3H), 6.67 (s, 1H), 4.52 (m, 1H), 4.35 (dt, 2H), 4.0 (dd, 1H), 3.85 (dd, 1H), 2.58 (s, 3H), 0.79 (s, 9H), 0.11 (s, 3H), 0.07 (s, 3H). M+1: 482.

7-(tert-Butyl-dimethyl-silanyloxy)-9-(2-methanesulfonyl-pyrimidin-4-yl)-2-phenyl-6,7,8,9-tetrahydro-pyrimido[1,2-a]pyrimidin-4-one: To a suspension of urea-$H_2O_2$ (120 mg, 1.27 mmol) in MeCN (2.0 mL), cooled at 0° C., was added trifluroacetic anhydride (0.18 mL, 1.27 mmol) slowly. After 5 min, the cold solution was added to a solution of 7-(tert-butyl-dimethyl-silanyloxy) -9-(2-methylsulfanyl-pyrimidin-4-yl)-2-phenyl-6,7,8,9-tetrahydro -pyrimido[1,2-a]pyrimidin-4-one (0.3 g, 0.62 mmol) in DCM (2.0 mL) at 0° C. The resulting mixture was stirred at room temperature for 3 h and was quenched with $NaHCO_3$ (aq). The mixture was then extracted with DCM (3×) and the organic layer was dried ($Na_2SO_4$) to provide a white solid after evaporation. This material was used directly for the next step. M+1: 498, 514.

7-(tert-Butyl-dimethyl-silanyloxy)-2-phenyl-9-[2(1-phenyl-ethylamino)-pyrimidin-4-yl]-6,7,8,9-tetrahydro-pyrimido[1,2-a]pyrimido[1,2-a]pyrimidin-4-one: A mixture of 7-(tert-butyl-dimethyl-silanyloxy)-9-(2-methanesulfonyl-pyrimidin-4-yl)-2-phenyl-6,7,8,9-tetrahydro-pyrimido[1,2-a]pyrimidin- 4-one, prepared from last step (0.6 mmol) and (S)-1-phenylethylamine (1.0 mL, 7.8 mmol) in dioxane (6 mL) was heated at 110° C. for 17 h. The brown solution was cooled to room temperature and was diluted with EtOAc (10 ML). The mixture was washed with $H_2O$ (2×), dried ($Na_2SO_4$), and concentrated to oil. Purification on silica (0-1% 2N NH3-MeOH in DCM) provided the product as a white solid. M+1: 555.

7-Hydroxy-2-phenyl-9-[2-(1-phenyl-ethylamino)-pyrimidin-4-yl]-6,7,8,9-tetrahydro-pyrimido[1,2-a]pyrimidin-4-one: A solution of 7-(tert-butyl-dimethyl-silanyloxy)-2-phenyl-9-[2-(1-phenyl-ethylamino)-pyrimidin-4-yl]-6,7,8,9-tetrahydro-pyrimido[1,2-a]pyrimidin-4-one (20 mg) in MeOH (3 mL)-DCM (1 mL) was treated with HCl (conc. 1.5 mL). After the mixture was stirred at room temperature for 16 h, it was neutralized with $NaHCO_3$ (aq) and then extracted with DCM (3×). The organic layer was dried ($Na_2SO_4$) and concentrated to a solid that was purified on silica (1-3% 2N $NH_3$—MeOH in DCM) to provide the product as a white solid. $^1$HNMR (400 MHz, DMSO-$d_6$): 8.12 (d, J 5.6,1 H), 7.94 (m, 2H), 7.70 (m, 1H, NH), 7.44 (m, 3H), 7.32 (t, J 7.2, 2H), 19 (m, 1H), 708 (d, J 5.6,1H), 5.50 (ds, 1H, OH), 5.01 (m, 1H, ), 4.39 (b, 1H), 4.22 (bt, 1.5 H), 3.89 (d, J 4.8,1H), 3.68 (m, 0.5H), 3.3 (b, 1H), 1.45 (d, J 7.2, 3H). M+1: 441.

EXAMPLE 67

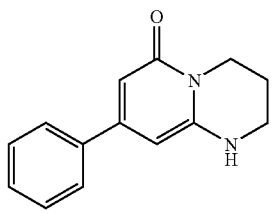

8-Phenyl-1,2,3,4-tetrahydro-pyrido[1,2-a]pyrimidin-6-one

Step A. 4-Cyano-3-phenyl-but-3-enoic acid ethyl ester. A 250 mL round-bottom flask equipped with a large stir bar was charged with 3-oxo-3-phenyl-propionic acid ethyl ester (48 g, 0.25 mol), benzene (80 mL), cyanoacetic acid (23 g, 0.27 mol), ammonium acetate (4 g, 0.05 mol), and acetic acid (7.5 mL, 0.13 mol) subsequently. The overall heterogeneous yellow mixture was equipped with a condenser and a Dean—Stark trap and heated under reflux for 96 h. The entire mixture was cooled to room temperature and poured into a separation funnel containing water (100 mL). The organic layer was taken and the aqueous layer was extracted with EtOAc (50 mL×2). Then the combined organic phases were dried over $Na_2SO_4$ followed by filtration and concentration to give the crude cyanamide as a brown syrup which was purified by vacuum distillation to give the desired product as a pale yellow oil.

Step B. 8-Phenyl-1,2,3,4-tetrahydro-pyrido[1,2-a]pyrimidin-6-one. A 50 mL round-bottom flask equipped with a stir bar was charged with the crude cyanamide product (2.15 g, 0.01 mol), 1,3-diaminopropane (0.84 mL, 0.01 mol) and 1,2-dichlorobenzene (5 mL) subsequently. The overall solution was equipped with a air-cool condenser and heated at 160° C. overnight. The resulting solution was concentrated and the crude material was passed through a short path of $SiO_2$ column by eluted with hexanes, DCM and 1% MeOH in DCM subsequently. The fraction that contained product was collected and concentrated followed by washing with EtOAc to obtain the desired pyridone product as a yellow solid. MS m/e 227 (M+H)$^+$.

EXAMPLE 68

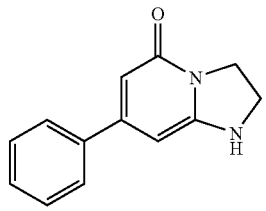

7-Phenyl-2,3-dihydro-1H-imidazo[1,2-a]pyridin-5-one. 4-Cyano-3-phenyl-but-3-enoic acid ethyl ester (crude, 9.37 g, 0.043 mol), ethylenediamine (3 mL, 0.043 mol) were mixed in dichlorobenze (20 mL) and heated at 160° C. overnight. The resulting suspension was cooled to room temperature, filtered, and the filtrated cake was washed with EtOAc and finally dried to provide the title compound as a brownish yellow solid. MS m/e 213 (M+H)$^+$.

EXAMPLE 69

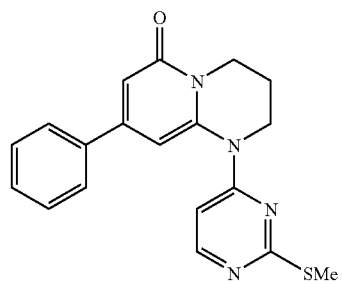

1-(2-Methylsulfanyl-pyrimidin-4-yl)-8-phenyl-1,2,3,4-tetrahydro-pyrido[1,2-a]pyrimidin-6-one. To a mixture of 8-phenyl-1,2,3,4-tetrahydro-pyrido[1,2-a]pyrimidin-6-one (1.86 g, 8.23 mmol), sodium tert-butoxide (1.6 g, 16 mmol), BINAP (0.15 g, 0.207 mmol), and Pd (OAc)$_2$ (55 mg, 0.2 mmol) was added toluene (20 mL) and 4-chloro-2-methylthiopyrimidine (1.5 mL, 12 mmol). After purged with N₂ for 10 min, the overall mixture was heated at 70° C. for 3 h prior to being cooled to room temperature. The resulting material was diluted with saturated NHCl(aq), water, and DCM. The organic layer was taken and the aqueous layer was extracted with DCM. The combined organic layers were dried over Na₂SO₄, filtrated, and concentrated. Column chromatographic purification (3% MeOH in DCM) of the crude residue afforded the title compound as a yellow solid. MS m/e 351 (M+H)⁺.

EXAMPLE 70

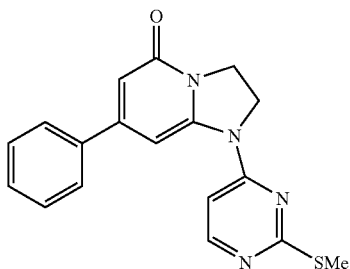

1-(2-Methylsulfanyl-pyrimidin-4-yl)-7-phenyl-2,3-dihydro-1H-imidazo[1,2-a]pyridin-5-one. Following the procedure described for the synthesis of 1-(2-methylsulfanyl-pyrimidin-4-yl)-8-phenyl-1,2,3,4-tetrahydro-pyrido[1,2-a]pyrimidin-6-one, but using 7-phenyl-2,3-dihydro-1H-imidazo[1,2-a]pyridin-5-one (1 g, 4.7 mmol), sodium tert-butoxide (1.26 g, 13.16 mmol), BINAP (0.43 g, 0.7 mmol), Pd(OAc)₂ (0.16 g, 0.7 mmol), toluene (20 mL) and 4-chloro-2-methylthiopyrimidine (0.66 mL, 0.56 mmol). The title compound was isolated as a yellow solid. MS m/e 337 (M+H)⁺.

EXAMPLE 71

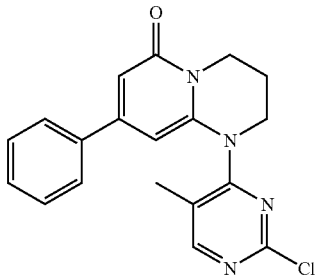

1-(2-Chloro-5-methyl-pyrimidin-4-yl)-8-phenyl -1,2,3,4dimethylaminopropyl)-tetrahydro-pyrido[1,2-a]pyrimidin-6-one. Following the procedure described above and using 8-phenyl-1,2,3,4-tetrahydro-pyrido[1,2-a]pyrimidin-6-one (0.48 g, 2.13 mmol), sodium tert-butoxide (0.41 g, 4.26 mmol), BINAP (66 mg, 0.11 mmol), Pd(OAc)₂ (24 mg, 0.11 mmol), toluene (5 mL) and 2,4-dichloro-5-methylpyrimidine (0.37 mL, 3.19 mmol). The title compound was isolated (120 mg) as a yellow solid, along with remaining starting material. MS m/e 353 (M+H)⁺.

EXAMPLE 72

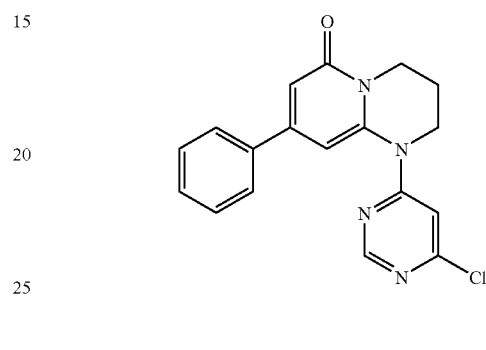

1-(6-Chloro-pyrimidin-4-yl)-8-phenyl-1,2,3,4-tetrahydro-pyrido[1,2-a]pyrimidin-6-one. To a stirred mixture of 1,8-phenyl-1,2,3,4-tetrahydro-pyrido[1,2-a]pyrimidin-6-one (0.23 g, 1.0 mmol), 4,6-dichloropyrmidine (0.23 g, 1.53 mmol) in DMF (3 mL) was added excess amount of NaH at 0° C. And the resulting slurry was stirred for 1.5 h at the same temperature prior to being poured into ice and extracted with DCM (2×). The combined organic layers were washed with water, brine, and dried over Na₂SO₄. Concentration followed by washing the residue with isopropyl alcohol yielded the title compound as a yellow solid. MS m/e 339 (M+H)⁺.

EXAMPLE 73

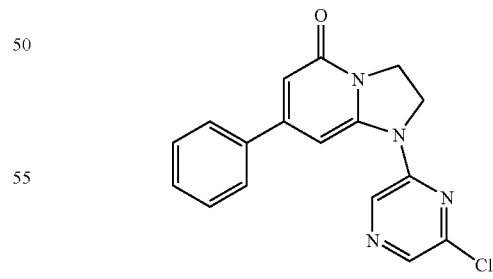

1-(6-Chloro-pyrazin-2-yl)-7-phenyl-2,3-dihydro-1H-imidazo[1,2-a]pyridin-5-one. Following the procedure described in the synthesis of 1-(2-methylsulfanyl-pyrimidin-4-yl)-7-phenyl-2,3-dihydro-1H-imidazo[1,2-a]pyridin-5-one, but using 2,6-dichloropyrimidine as the coupling component, 7-phenyl-2,3-dihydro-1H-imidazo[1,2-a]pyridin-5- one (0.5 g, 2.4 mmol) was converted into the title product as a pale yellow solid. MS m/e 325 (M+H)+.

EXAMPLE 74

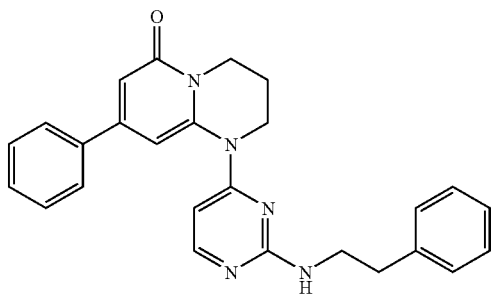

1-(2-Phenethylamino-pyrimidin-4-yl)-8-phenyl-1,2,3,4-tetrahydro-pyrido[1,2-a]pyrimidin-6-one. To a solution of 1-(2-methylsulfanyl-pyrimidin-4-yl)-8-phenyl-1,2,3,4-tetrahydro-pyrido[1,2-a]pyrimidin-6-one (1.46 g, 4.17 mmol) in DCM (10 mL) was added slowly m-CPBA (1.23 g, 70%, 5.01 mmol) at 0° C. and the resulting suspension was stirred at the same temperature for 1 h prior to being quenched with water and saturated sodium bicarbonate. The organic layer was taken and the aqueous layer was extracted with DCM. Then the combined organic phases were washed with 1N NaOH, brine and dried over Na$_2$SO$_4$. Filtration followed by concentration yielded yellow foam of desired corresponding sulfoxide, which was used directly without further purification. The crude sulfoxide (0.14 g, 0.394 mmol) and phenylethylamine (0.15 mL, 1.18 mmol) in NMP (2 mL) was heated at 100° C. for 4 h. After concentrated, the pale brown residue was diluted with isopropyl alcohol (or ethyl acetate) and the precipitate was collected as the title compound. MS m/e 424 (M+H)+.

EXAMPLE 75

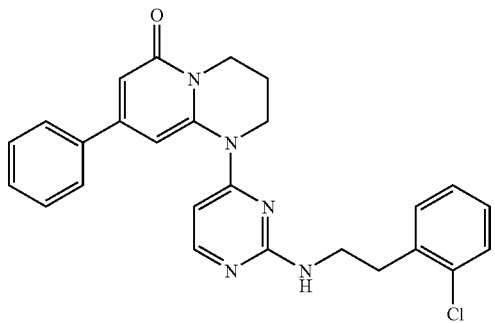

1-{2-[2-(2-Chloro-phenyl)-ethylamino]-pyrimidin-4-yl}-8-phenyl-1,2,3,4-tetrahydro-pyrido[1,2-a]pyrimidin-6-one.

Followed the same procedure described for the synthesis of 1-(2-phenethylamino-pyrimidin-4-yl)-8-phenyl-1,2,3,4-tetrahydro-pyrido[1,2-a]pyrimidin-6-one, the sulfoxide (0.22 g, 0.6 mmol) was displaced with 2-(2-chlorophenyl)ethylamine (0.25 mL, 1.8 mmol) to give the title compound as a yellow solid. MS m/e 458 (M+H)+.

EXAMPLE 76

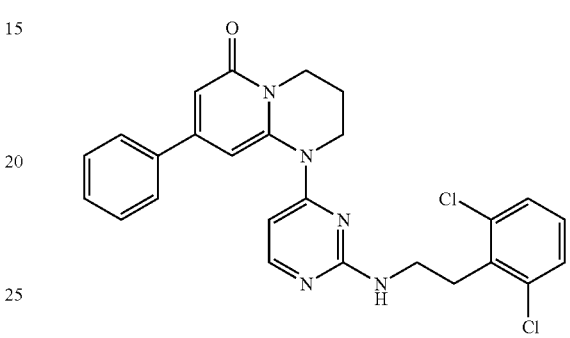

1-{2-[2-(2,6-Dichloro-phenyl)-ethylamino]-pyrimidin-4-yl}-8-phenyl-1,2,3,4-tetrahydro-pyrido[1,2-a]pyrimidin-6-one. Followed the same procedure described for the synthesis of 1-(2-phenethylamino-pyrimidin-4-yl)-8-phenyl-1,2,3,4-tetrahydro-pyrido[1,2-a]pyrimidin-6-one, the sulfoxide (0.1 g, 0.27 mmol) was displaced with 2-(2,6-dichlorophenyl)ethylamine (0.16 g, 0.82 mmol) to give the title compound as a yellow solid. MS m/e 492 (M+H)+.

EXAMPLE 77

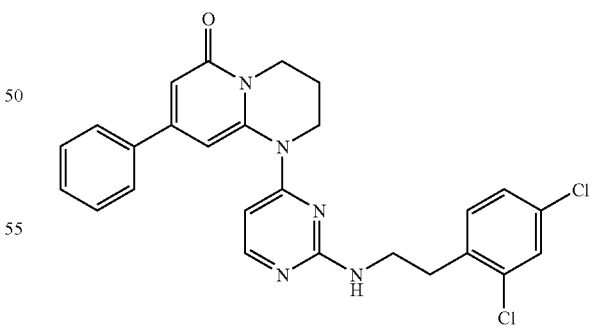

1-{2-[2-(2,4-Dichloro-phenyl)-ethylamino]-pyrimidin-4-yl}-8-phenyl-1,2,3,4-tetrahydro-pyrido[1,2-a]pyrimidin-6-one. Followed the same procedure in the synthesis of 1-(2-phenethylamino-pyrimidin-4-yl)-8-phenyl-1,2,3,4-tetrahydro-pyrido[1,2-a]pyrimidin-6-one, the sulfoxide (0.11 g, 0.3 mmol) was displaced with 2-(2,4-dichlorophenyl)ethylamine (0.14 mL, 0.9 mmol) to give the title compound as a yellow solid. MS m/e 492 (M+H)⁺.

EXAMPLE 78

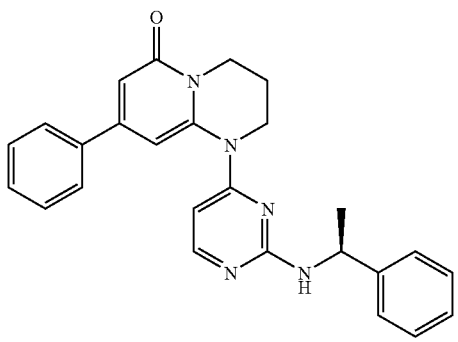

8-Phenyl-1-[2-(1S)-phenyl-ethylamino)-pyrimidin-4-yl]-1,2,3,4-tetrahydro-pyrido[1,2-a]pyrimidin-6-one. Followed the same procedure described for the synthesis of 1-(2-phenethylamino-pyrimidin-4-yl)-8-phenyl-1,2,3,4-tetrahydro-pyrido[1,2-a]pyrimidin-6-one, the sulfoxide (0.12 g, 0.34 mmol) was displaced with (S)-(−)-α-methylbenzylamine (0.21 mL, 1.03 mmol) to give the title compound as a yellow solid. MS m/e 424 (M+H)⁺.

EXAMPLE 79

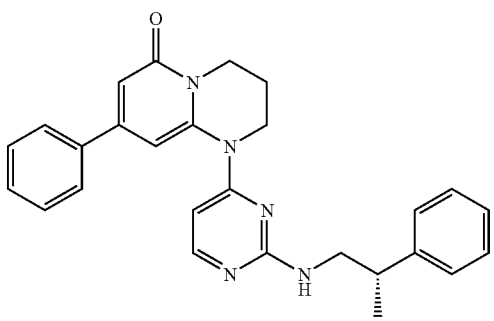

8-Phenyl-1-[2-(2S)-phenyl-propylamino)-pyrimidin-4-yl]-1,2,3,4-tetrahydro-pyrido[1,2-a]pyrimidin-6-one. Followed the same procedure in the synthesis of 1-(2-phenethylamino-pyrimidin-4-yl)-8-phenyl-1,2,3,4-tetrahydro-pyrido[1,2-a]pyrimidin-6-one, the sulfoxide (0.16 g, 0.44 mmol) was displaced with (S)-(−)-β-methylbenzylamine (0.16 mL, 1.09 mmol) to give the title compound as a yellow solid. MS m/e 438 (M+H)⁺.

EXAMPLE 80

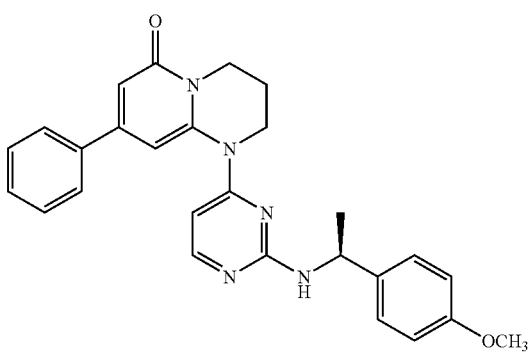

1-{2-[(1S)-(4-Methoxy-phenyl)-ethylamino]-pyrimidin-4-yl}-8-phenyl-1,2,3,4-tetrahydro-pyrido[1,2-a]pyrimidin-6-one. Followed the same procedure described for the synthesis of 1-(2-phenethylamino-pyrimidin-4-yl)-8-phenyl-1,2,3,4-tetrahydro-pyrido[1,2-a]pyrimidin-6-one, the sulfoxide (0.34 g, 0.93 mmol) was displaced with (S)-1-(4-methoxy-phenyl)-ethylamine (0.42 g, 2.79 mmol) to give the title compound as a light yellow solid. MS m/e 454 (M+H)⁺.

EXAMPLE 81

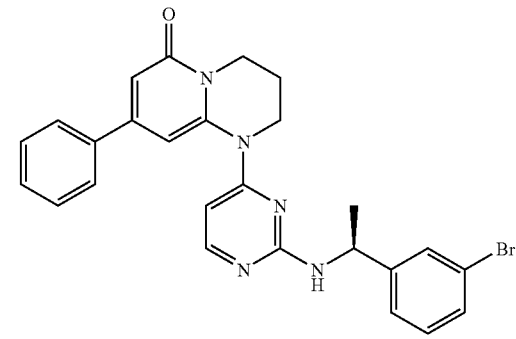

1-{2-(S)-[1-(3-Bromo-phenyl)-ethylamino]-pyrimidin-4-yl}-8-phenyl-1,2,3,4-tetrahydro-pyrido[1,2-a]pyrimidin-6-one. Followed the same procedure described for the synthesis of 1-(2-phenethylamino-pyrimidin-4-yl)-8-phenyl-1,2,3,4-tetrahydro-pyrido[1,2-a]pyrimidin-6-one, the sulfoxide (0.152 g, 0.42 mmol) was displaced with (S)-1-(3-bromophenyl)-ethylamine (0.42 g, 2.79 mmol) to give the title compound as a light yellow solid. MS m/e 502 (M+H)⁺.

EXAMPLE 82

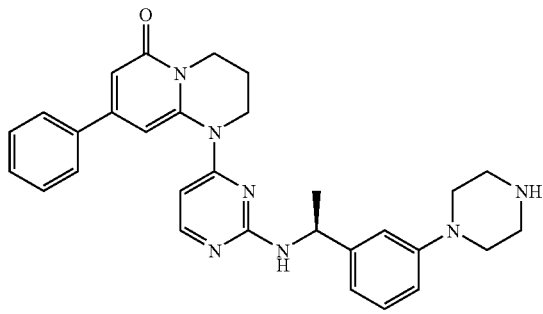

8-Phenyl-1-{2-(S)-[1-(3-piperazin-1-yl-phenyl)-ethylamino]-pyrimidin-4-yl}-1,2,3,4-tetrahydro-pyrido[1,2-a]pyrimidin-6-one. Following the similar Pd-catalyzed amination procedure described in the synthesis of 1-(2-phenethylamino-pyrimidin-4-yl)-8-phenyl-1,2,3,4-tetrahydro-pyrido[1,2-a]pyrimidin-6-one, 1-{2-(S)-[1-(3-bromo-phenyl)-ethyl amino]-pyrimidin-4-yl}-8-phenyl-1,2,3,4-tetrahydro-pyrido[1,2-a]pyrimidin-6-one (0.21 g, 0.42 mmol) was reacted with piperazine (54 mg, 0.63 mmol) to give the title compound as a light yellow solid. MS m/e 508 (M+H)⁺.

EXAMPLE 83

1-{2-[2-(3-Hydroxymethyl-phenyl)-1-methyl-ethylamino]-pyrimidin-4-yl}-8-phenyl-1,2,3,4-tetrahydro-pyrido[1,2-a]pyrimidin-6-one. Following the same procedure described for the synthesis of 1-(2-phenethylamino-pyrimidin-4-yl)-8-phenyl-1,2,3,4-tetrahydro-pyrido[1,2-a]pyrimidin-6-one, the sulfoxide (0.29 g, 0.83 mmol) was displaced with [3-(2-amino-propyl)-phenyl]-methanol (0.3 g, 1.66 mmol) to give the title compound as a light yellow solid. MS m/e 468 (M+H)⁺.

EXAMPLE 84

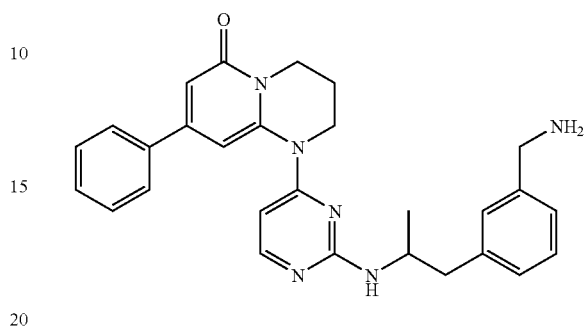

1-{2-[2-(3-Aminomethyl-phenyl)-1-methyl-ethylamino]-pyrimidin-4-yl}-8-phenyl-1,2,3,4-tetrahydro-pyrido[1,2-a] pyrimidin-6-one. To a stirred solution of 1-{2-[2. -(3-hydroxymethyl-phenyl)-1-methyl-ethylamino]-pyrimidin-4-yl}-8. -phenyl-1,2,3,4-tetrahydro-pyrido[1,2-a]pyrimidin-6-one (0.22 g, 4.7 mmol) in THF (5 mL) was added DBU (0.14 g, 9.4 mmol) and then diphenylphosphoryl azide (0.26 g, 9.4 mmol) and the resulting solution was stirred at room temperature overnight. The resulting mixture was diluted with DCM and water subsequently and the separated organic layer was washed with saturated sodium bicarbonate and brine. Removal of the solvent provided the crude azide, which was reduced under hydrogenation conditions (H₂, Pd/C, ethanol, room temperature, 4 h). Filtration followed by concentration obtained the crude amine which was purified with flash column chromatography (5% MeOH in DCM) to furnish the title compound as a yellow solid. MS m/e 467 (M+H)⁺.

EXAMPLE 85

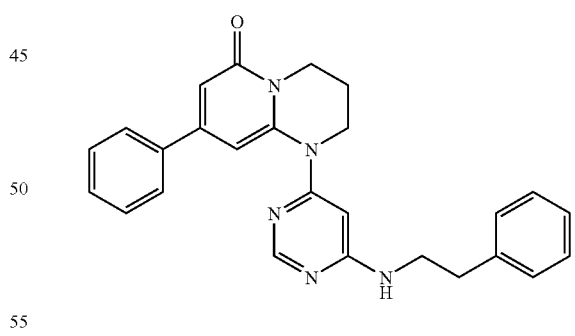

1-(6-Phenethylamino-pyrimidin-4-yl)-8-phenyl-1,2,3,4-tetrahydro-pyrido[1,2-a]pyrimidin-6-one. To a stirred mixture of 1-(6-chloro-pyrimidin-4-yl)-8-phenyl -1,2,3,4-tetrahydro-pyrido[1,2-a]pyrimidin-6-one (0.158 mg, 0.47 mmol) and excess of K₂CO₃ in DMF (3 mL) was added phenethylamine (0.15 mL, 1.2 mmol). The overall reaction vessel was irradiated under microwave conditions at 150° C. for 10 min. After diluted with water and EtOAc, the organic layer was taken and the aqueous layer was extracted with EtOAc. The overall organic layers were washed with water, brine, and dried (Na₂SO₄). Filtration followed by evaporation gave the crude residue, which was washed with EtOAc/ether to provide the title compound as a light yellow solid. MS m/e 424 (M+H)+.

EXAMPLE 86

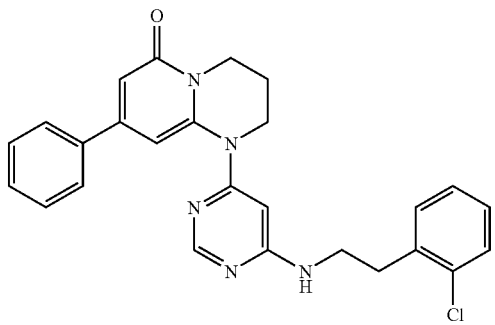

1-{6-[2-(2-Chloro-phenyl)-ethylamino]-pyrimidin-4-yl}-8-phenyl-1,2,3,4-tetrahydro-pyrido[1,2-a]pyrimidin-6-one. Followed the same procedure described for the synthesis of 1-(2-phenethylamino-pyrimidin-4-yl)-8-phenyl-1,2,3,4-tetrahydro -pyrido[1,2-a]pyrimidin-6-one, 1-(6-chloro-pyrimidin-4-yl)-8-phenyl-1,2,3,4-tetrahydro -pyrido[1,2-a]pyrimidin-6-one (0.136 g, 0.40 mmol) was reacted with 2-(2-chlorophenyl)ethylamine (0.17 mL, 1.2 mmol) to give the title compound as a yellow solid. MS m/e 458 (M+H)+.

EXAMPLE 87

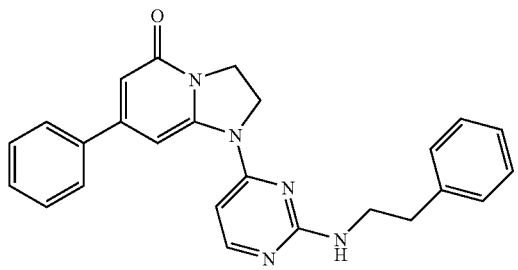

1-(2-Phenethylamino-pyrimidin-4-yl)-7-phenyl-2,3-dihydro-1H-imidazo[1,2-a]pyridin-5-one. To a solution of 1-(2-methylsulfanyl-pyrimidin-4-yl)-7-phenyl-2,3-dihydro-1H-imidazo[1,2-a]pyridin-5-one (2.0 g, 5.95 mmol) in a 4:1 mixture of acetonitrile/trifluoroacetic acid (25 mL) was added urea-hydrogen peroxide (1.5 eq) followed by slow addition of trifluroacetic anhydride (1.5 eq) at 0° C. and the resulting suspension was stirred at the same temperature for 1 h prior to being warmed up to room temperature and stirred for another 2 h. At this point 0.5 eq more of urea-hydrogen peroxide and trifluroacetic anhydride were added to consume all of remaining starting material. After concentrated, the crude material was partitioned between water and CHCl3 and the separated organic layer was washed with 5% NaHCO3, brine, and the solvent was removed to yield the mixture of sulfoxide/sulfone as an off-white solid, which was used without any purifications.

To a stirred solution of crude sulfoxide/sulfone (0.25 g, 0.69 mmol) in NMP (5 mL) was added phenethylamine (0.1376 g) and the resulting mixture was heated at 130° C. overnight. After cooled, the reaction mixture was diluted with water and DCM, the organic layer was taken and the aqueous layer was extracted with DCM. The combined organic layers were washed with brine, dried over Na2SO4 and concentrated under reduced pressure to afford the crude material, which was subjected to a preparative thin-layer chromatographic purification to provide the title compound as a pale yellow solid. MS m/e 410 (M+H)+.

EXAMPLE 88

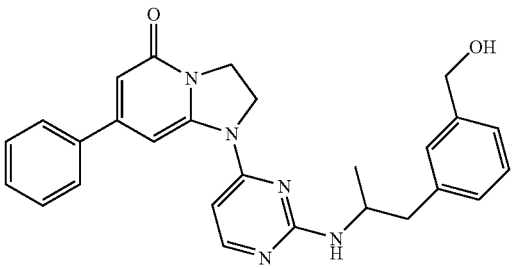

1-{2-[2-(3-Hydroxymethyl-phenyl)-1-methyl-ethylamino]-pyrimidin-4-yl}-7-phenyl-2,3-dihydro-1H-imidazo[1,2-a]pyridin-5-one. Following the same procedure described for the synthesis of 1-(2-phenethylamino-pyrimidin-4-yl)-8-phenyl-1,2,3,4-tetrahydro-pyrido[1,2-a]pyrimidin-6-one, the sulfoxide/sulfone (0.4 g) was displaced with [3-(2-aminopropyl)-phenyl]-methanol (1.2 eq) to give the title compound as a light yellow solid. MS m/e 454 (M+H)+.

EXAMPLE 89

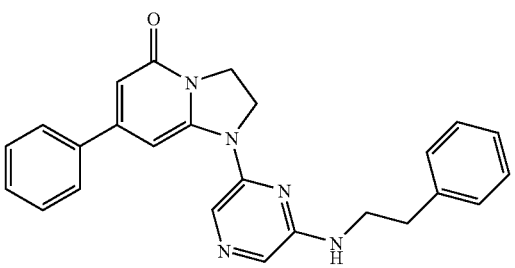

1-(6-Phenethylamino-pyrazin-2-yl)-7-phenyl-2,3-dihydro-1H-imidazo[1,2-a]pyridin-5-one. To a mixture of 1-(6-chloro-pyrazin-2-yl)-7-phenyl-2,3-dihydro-1H-imidazo[1, 2-a]pyridin-5-one (85 mg, 0.26 mmol), sodium tert-butoxide (70 mg, 2.8 eq), BINAP (24 mg, 15% eq), and Pd (OAc)2 (9 mg, 15% eq) was added toluene (5 mL) and phenethylamine (39 μL, 1.2 eq). After purged with N2 for 10 min, the overall mixture was heated at 70° C. for 3 h prior to being cooled to room temperature. The resulting material was filtered through Celite and the filtrated cake was washed with DCM/MeOH (98:2) and the filtrates were concentrated. The residual material was purified by a preparative thin-layer chromatography (2% MeOH in DCM) to provide the title compound as a pale yellow solid. MS m/e 410 (M+H)+.

Biological Assays

The following assays were used to characterize the ability of compounds of the invention to inhibit the production of TNF-α and IL-1-β. The second assay can be used to measure the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a cyclooxygenase enzyme (COX-1 and COX-2) inhibition activity in vitro assay, can be used to characterize the ability of compounds of the invention to inhibit COX-1 and/or COX-2. The fifth assay, a Raf-kinase inhibition assay, can be used to characterize the compounds of the invention to inhibit phosphorylation of MEK by activated Raf-kinase.

Lipopolysaccharide-Activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2 \times 10^6$/mL in DMEM supplemented to contain 2% FCS, 10 mM, 0.3 mg/mL glutamate, 100 U/mL penicillin G and 100 mg/mL streptomycin sulfate (complete media). Cells were plated into Falcon flat bottom, 96 well culture plates (200 μL/well) and cultured overnight at 37° C. and 6% $CO_2$. Non-adherent cells were removed by washing with 200 μl/well of fresh medium. Wells containing adherent cells (~70% monocytes) were replenished with 100 μL of fresh medium.

Preparation of Test Compound Stock Solutions

Test compounds were dissolved in DMZ. Compound stock solutions were prepared to an initial concentration of 10-50 μM. Stocks were diluted initially to 20-200 μM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 μL complete medium. Monocytes were cultured with test compounds for 60 min at which time 25 μL of complete medium containing 30 ng/mL lipopolysaccharide from E. coli K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 μL/well of 3 μg/mL murine anti-human TNF-α MAb (R&D Systems #MAB210). Wells were then blocked for 1 h at room temperature with 200 μL/well of $CaCl_2$-free ELISA buffer supplemented to contain 20 mg/mL BSA (standard ELISA buffer: 20 mM, 150 mM NaCl, 2 mM $CaCl_2$, 0.15 mM thimerosal, pH 7.4). Plates were washed and replenished with 100 μL of test supernatants (diluted 1:3) or standards. Standards consisted of eleven 1.5-fold serial dilutions from a stock of 1 ng/mL recombinant human TNF (R&D Systems). Plates were incubated at room temperature for 1 h on orbital shaker (300 rpm), washed and replenished with 100 μL/well of 0.5 μg/mL goat anti-human TNF-α (R&D systems #AB-210-NA) biotinylated at a 4:1 ratio. Plates were incubated for 40 min, washed and replenished with 100 μL/well of alkaline phosphatase-conjugated streptavidin (Jackson ImmunoResearch #016-050-084) at 0.02 μg/mL. Plates were incubated 30 min, washed and replenished with 200 μL/well of 1 mg/mL of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-α, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-Activated THP1 Cell TNF Production Assay

THP1 cells are resuspended in fresh THP1 media (RPMI 1640, 10% heat-inactivated FBS, 1×PGS, 1×NEAA, plus 30 μM βME) at a concentration of 1E6/mL. One hundred microliters of cells per well are plated in a polystyrene 96-well tissue culture. One microgram per mL of bacterial LPS is prepared in THP1 media and is transferred to the wells. Test compounds are dissolved in 100% DMSO and are serially diluted 3 fold in a polypropylene 96-well microtiter plate (drug plate). HI control and LO control wells contain only DMSO. One microliter of test compound from the drug plate followed by 10 μL of LPS are transferred to the cell plate. The treated cells are induced to synthesize and secrete TNF-α at 37° C. for 3 h. Forty microliters of conditioned media are transferred to a 96-well polypropylene plate containing 110 μL of ECL buffer (50 mM Tris-HCl pH 8.0, 100 mM NaCl, 0.05% Tween 20, 0.05% $NaN_3$ and 1%FBS) supplemented with 0.44 nM MAB610 monoclonal Ab (R&D Systems), 0.34 nM ruthenylated AF210NA polyclonal Ab (R&D Systems) and 44 μg/mL sheep anti-mouse M280 Dynabeads (Dynal). After a 2 h incubation at room temperature with shaking, the reaction is read on the ECL M8 Instrument (IGEN Inc.). A low voltage is applied to the ruthenylated TNF-α immune complexes, which in the presence of TPA (the active component in Origlo), results in a cyclical redox reaction generating light at 620 nM. The amount of secreted TNF-α in the presence of compound compared with that in the presence of DMSO vehicle alone (HI control) is calculated using the formula: % control (POC)=(cpd−average LO)/(average HI−average LO)*100. Data (consisting of POC and inhibitor concentration in μM) is fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

The following compounds exhibit activities in the THP1 cell assay (LPS induced TNF release) with $IC_{50}$ values of 20 μM or less:

1-(2-{2-[3-(1-amino-1-methyl-ethyl)-phenyl]-1-methyl-ethylamino}-pyrimidin-4-yl)-8-phenyl-1,2,3,6-tetrahydro-pyrimido[1,2-a]pyrimidin-4-one;

1-(2-{2-[4-(1-amino-ethyl)-phenyl]-ethylamino}-pyrimidin-4-yl)-8-phenyl-1,23,6-tetrahydro-pyrimido[1,2-a]pyrimidin-4-one;

1-(2-{2[4-(1-isopropylamino-ethyl)-phenyl]-ethylamino}-pyrimidin-4-yl)-8-phenyl-1,2,3,6-tetrahydro-pyrimido[1,2-a]pyrimidin-4-one;

1-(2-{2-[4-(2-amino-propyl)-phenyl]-1-methyl -ethylamino}-pyrimidin-4-yl)-8-phenyl-1,2,3,6-tetrahydro-pyrimido[1,2-a]pyrimidin-4-one;

1-(2-phenethylamino-pyrimidin-4-yl)-7-phenyl-2,3-dihydro-1H-imidazo[1,2-a]pyridin-5-one;

1-(2-phenethylamino-pyrimidin-4-yl)-8-phenyl-1,2,3,4-tetrahydro -pyrido[1,2-a]pyrimidin-6-one;

1-(6-phenethylamino-pyrazin-2-yl)-7-phenyl-2,3-dihydro-1H -imidazo[1,2-a]pyridin-5-one;

1-(6-phenethylamino-pyrimidin-4-yl)-8-phenyl-1,2,3,4-tetrahydro -pyrido[1,2-a]pyrimidin-6-one;

1-{2-(S)-[1-(3-bromo-phenyl)-ethylamino]-pyrimidin-4-yl}-8-phenyl-1,2,3,4-tetrahydro-pyrido[1,2-a]pyrimidin-6-one;

1-{2-[(1S)-(4-methoxy-phenyl)-ethylamino]-pyrimidin-4-yl}-8-phenyl-1,2,3,4-tetrahydro-pyrido[1,2-a]pyrimidin-6-one;

1-{2-[2-(2,4-dichloro-phenyl)-ethylamino]-pyrimidin-4-yl}-8-phenyl-1,2,3,4-tetrahydro-pyrido[1,2-a]pyrimidin-6-one;

1-{2-[2-(2,6-dichloro-phenyl)-ethylamino]-pyrimidin-4-yl}-8-phenyl-1,2,3,4-tetrahydro-pyrido[1,2-a]pyrimidin-6-one;

1-{2-[2-(2-chloro-phenyl)-ethylamino]-pyrimidin-4-yl}-8-phenyl-1,2,3,4-tetrahydro-pyrido[1,2-a]pyrimidin-6-one;

1-{2-[2-(3-aminomethyl-phenyl)-1-methyl-ethylamino]-pyrimidin-4-yl}-8-phenyl-1,2,3,4-tetrahydro-pyrido[1,2-a]pyrimidin-6-one;

1-{2-[2-(3-hydroxymethyl-phenyl)-1-methyl-ethylamino]-pyrimidin-4-yl}-8-phenyl-1,2,3,4-tetrahydro-pyrido[1,2-a]pyrimidin-6-one;

1-{2-[2-(3-hydroxymethyl-phenyl)-1-methyl-ethylamino]-pyrimidin-4-yl}-7-phenyl-2,3-dihydro-1H-imidazo[1,2-a]pyridin-5-one;

1-{2-[2-(4-aminomethyl-phenyl)-1-methyl-ethylamino]-pyrimidin-4-yl}-8-phenyl-1,2,3,6-tetrahydro-pyrimido[1,2-a]pyrimidin-4-one;

1-{6-[2-(2-chloro-phenyl)-ethylamino]-pyrimidin-4-yl}-8-phenyl-1,2,3,4-tetrahydro-pyrido[1,2-a]pyrimidin-6-one;

2-(2-fluorophenyl)-9-[2-(1(S)-phenyl-ethylamino)-pyrimidin -4-yl]-6,7,8,9-tetrahydro-pyrimido[1,2-a]pyrimidin-4-one;

2-(2-trifluoromethylphenyl)-9-[2-(1(S)-phenyl-ethylamino) -pyrimidin-4-yl]-6,7,8,9-tetrahydro-pyrimido[1,2-a]pyrimidin-4-one;

2-(3,4-dichlorophenyl)-9-[2-(1(S)-phenyl-ethylamino) -pyrimidin-4-yl]-6,7,8,9-tetrahydro-pyrimido[1,2-a]pyrimidin-4-one;

2-(3,4-dimethyl-phenyl)-9-[2-(1(S)-phenyl-ethylamino) -pyrimidin-4-yl]-6,7,8,9-tetrahydro-pyrimido[1,2-a]pyrimidin-4-one;

2-(3-aminophenyl)-9-[2-(1(S)-phenyl-ethylamino)-pyrimidin -4-yl]-6,7,8,9-tetrahydro-pyrimido[1,2-a]pyrimidin-4-one;

2-(3-dimethylaminephenyl)-9-[2-(1(S)-phenyl-ethylamino) -pyrimidin-4-yl]-6,7,8,9-tetrahydro-pyrimido[1,2-a]pyrimidin-4-one;

2-(3-ethylphenyl)-9-[2-(1(S)-phenyl-ethylamino)-pyrimidin -4-yl]-6,7,8,9-tetrahydro-pyrimido[1,2-a]pyrimidin-4-one;

2-(3-nitrophenyl)-9-[2-(1(S)-phenyl-ethylamino)-pyrimidin -4-yl]-6,7,8,9-tetrahydro-pyrimido[1,2-a]pyrimidin-4-one;

2-(4-fluorophenyl)-9-[2-(1(S)-phenyl-ethylamino)-pyrimidin -4-yl]-6,7,8,9-tetrahydro-pyrimido[1,2-a]pyrimidin-4-one;

2-(4-methoxyphenyl)-9-[2-(1(S)-phenyl-ethylamino)-pyrimidin -4-yl]-6,7,8,9-tetrahydro-pyrimido[1,2-a]pyrimidin-4-one;

2-(4-pyridyl)-9-[2-(1(S)-phenyl-ethylamino)-pyrimidin -4-yl]-6,7,8,9-tetrahydro-pyrimido[1,2-a]pyrimidin-4-one;

2-(phenyl)-9-[2-(1(S)-phenyl-ethylamino)-pyrimidin-4-yl]-6,7,8,9-tetrahydro-pyrimido[1,2-a]pyrimidin-4-one;

2-(tert-butyl)-9-[2-(1(S)-phenyl-ethylamino)-pyrimidin-4-yl]-6,7,8,9-tetrahydro-pyrimido[1,2-a]pyrimidin-4-one;

2-{-[2-(3-aminomethyl-phenyl)-1-methyl-ethylamino]-pyrimidine -4-ylamino}-3-methyl-6-phenyl-3H-pyrimidin-4-one;

3-amino-9-{2-[2-(3-aminomethyl-phenyl)-1-methyl -ethylamino]-pyrimidin-4-yl}-2-phenyl-6,7,8,9-tetrahydro-pyrimido[1,2-a]pyrimidin-4-one;

3-amino-9-{2-[ethyl-2-(2-chlorophenyl)]-pyrimidin-4-yl}-2-phenyl-6,7,8,9-tetrahydro-pyrido[1,2-a]pyrimidin-4-one;

3-amino-9-{2-[ethyl-2-phenyl]-pyrimidin-4-yl}-2-phenyl-6,7,8,9-tetrahydro-pyrimido[1,2-a]pyrimidin-4-one;

3-methyl-9-{2-[1-(S)-phenylethyl]-pyrimidin-4-yl}-2-phenyl-6,7,8,9-tetrahydro-pyrimido[1,2-a]pyrimidin-4-one;

3-nitro-9-{2-[ethyl-2-phenyl]-pyrimidin-4-yl}-2-phenyl-6,7,8,9-tetrahydro-pyrimido[1,2-a]pyrimidin-4-one;

7-(2-Isopropylamino-ethyl)-9-(2-phenethylamino-pyrimidin-4-yl) -2-phenyl-6,7,8,9-tetrahydro-pyrimido[1,2-a]pyrimidin-4-one;

7-(ethyl-2-amino(N-benzyl))-9-(2-phenethylamino-pyrimidin-4-yl) -2-phenyl-6,7,8,9-tetrahydro-pyrimido[1,2-a]pyrimidin-4-one;

7-(ethyl-2-amino)-9-(2-phenethylamino-pyrimidin-4-yl)-2-phenyl-6,7,8,9-tetrahydro-pyrimido[1,2-a]pyrimidin-4-one;

7-(ethyl-2-carbamic acid benzyl ester)-9-(2-phenethylamino-pyrimidin-4-yl)-2-phenyl-6,7,8,9-tetrahydro-pyrimido[1,2-a]pyrimidin-4-one;

7-(propionic acid )-9-(2-phenethylamino-pyrimidin-4-yl)-2-phenyl-6,7,8,9-tetrahydro-pyrimido[1,2-a]pyrimidin-4-one;

7-(propionic acid ethyl ester)-9-(2-phenethylamino-pyrimidin-4-yl) -2-phenyl-6,7,8,9-tetrahydro-pyrimido[1,2-a]pyrimidin-4-one;

7-hydroxy-2-phenyl-9-[2-(1-phenyl-ethylamino)-pyrimidin-4-yl]-6,7,8,9-tetrahydro-pyrimido[1,2-a]pyrimidin-4-one;

8-phenyl-1-[2-(1S)-phenyl-ethylamino)-pyrimidin-4-yl]-1,2,3,4-tetrahydro-pyrido[1,2-a]pyrimidin-6-one;

8-phenyl-1-[2-(2S)-phenyl-propylamino)-pyrimidin-4-yl]-1,2,3,4-tetrahydro-pyrido[1,2-a]pyrimidin-6-one;

8-phenyl-1-{2-(S)-[1-(3-piperazin-1-yl-phenyl) -ethylamino]-pyrimidin-4-yl}-1,2,3,4-tetrahydro-pyrido[1,2-a]pyrimidin-6-one;

9-(2-{2-(2-hydroxyethyl)amino}-pyrimidin-4-yl)-2-phenyl-6,7,8,9-tetrahydro-pyrimido[1,2-a]pyrimidin-4-one;

9-(2-{2-(benzyl)amino}-pyrimidin-4-yl)-2-phenyl -6,7,8,9-tetrahydro-pyrimido[1,2-a]pyrimidin-4-one;

9-(2-{2-(ethyl-1(S)-isopropyl-2-ol)amino}-pyrimidin-4-yl)-2-phenyl-6,7,8,9-tetrahydro-pyrimido[1,2-a]pyrimidin-4-one;

9-(2-{2-(ethyl-1(S)methyl-2-(3-methylaminophenyl))amino}-pyrimidin-4-yl)-2-phenyl-6,7,8,9-tetrahydro-pyrimido[1,2-a]pyrimidin-4-one;

9-(2-{2-(ethyl-1(S)-methyl-2-ol)amino}-pyrimidin-4-yl)-2-phenyl-6,7,8,9-tetrahydro-pyrimido[1,2-a]pyrimidin-4-one;

9-(2-{2-(ethyl-1(S)methyl-2-phenyl)amino}-pyrimidin-4-yl)-2-phenyl-6,7,8,9-tetrahydro-pyrimido[1,2-a]pyrimidin-4-one;

9-(2-{2-(ethyl-1-amido-2-phenyl)amino}-pyrimidin-4-yl)-2-phenyl-6,7,8,9-tetrahydro-pyrimido[1,2-a]pyrimidin-4-one;

9-(2-{2-(ethyl-1-methyl-2-(3-aminophenyl))amino}-pyrimidin-4-yl)-2-phenyl-6,7,8,9-tetrahydro-pyrimido[1,2-a]pyrimidin-4-one;

9-(2-{2-(ethyl-1-methyl-2-(3-cyanophenyl))amino}-pyrimidin-4-yl)-2-phenyl-6,7,8,9-tetrahydro-pyrimido[1,2-a]pyrimidin-4-one;

9-(2-{2-(ethyl-1-methyl-2-(3-methylalcoholphenyl))amino}-pyrimidin-4-yl)-2-phenyl -6,7,8,9-tetrahydro-pyrimido[1,2-a]pyrimidin-4-one;

9-(2-{2-(ethyl-1-methyl-2-(3-methylaminophenyl))amino}-pyrimidin-4-yl)-2phenyl -6,7,8,9-tetrahydro-pyrimido[1,2-a]pyrimidin-4-one;

9-(2-{2-(ethyl-2-(2-chlorophenyl))amino}-pyrimidin-4-yl)-2-phenyl-6,7,8,9-tetrahydro-pyrimido[1,2-a]pyrimidin-4-one;

9-(2-{2-(ethyl-2-(2-methoxyphenyl))amino}-pyrimidin-4-yl)-2-phenyl-6,7,8,9-tetrahydro-pyrimido[1,2-a]pyrimidin-4-one;

9-(2-{2-(ethyl-2-(3,4-dimethylphenyl))amino}-pyrimidin - 4-yl)-2-phenyl-6,7,8,9-tetrahydro-pyrimido[1,2-a]pyrimidin-4-one;

9-(2-{2-(ethyl-2-(4-hydroxyphenyl))amino}-pyrimidin-4-yl)-2-phenyl-6,7,8,9-tetrahydro-pyrimido[1,2-a]pyrimidin-4-one;

9-(2-{2-(ethyl-2-(4-methoxyphenyl))amino}-pyrimidin-4-yl)-2-phenyl-6,7,8,9-tetrahydro-pyrimido[1,2-a]pyrimidin-4-one;

9-(2-{2-(ethyl-2-(4-methylphenyl))amino}-pyrimidin-4-yl)-2-phenyl-6,7,8,9-tetrahydro-pyrimido[1,2-a]pyrimidin-4-one;

9-(2-{2-(ethyl-2-aminophenyl)amino}-pyrimidin-4-yl)-2-phenyl-6,7,8,9-tetrahydro-pyrimido[1,2-a]pyrimidin-4-one;

9-(2-{2-(ethyl-2-keto-2-phenyl)amino}-pyrimidin-4-yl)-2-phenyl-6,7,8,9-tetrahydro-pyrimido[1,2-a]pyrimidin-4-one;

9-(2-{2-(ethyl-2-methoxy)amino}-pyrimidin-4-yl)-2-phenyl-6,7,8,9-tetrahydro-pyrimido[1,2-a]pyrimidin-4-one;

9-(2-{2-(ethyl-2-morpholino)amino}-pyrimidin-4-yl)-2-phenyl-6,7,8,9-tetrahydro-pyrimido[1,2-a]pyrimidin-4-one;

9-(2-{2-(ethyl-2-phenoxy)amino}-pyrimidin-4-yl)-2-phenyl-6,7,8,9-tetrahydro-pyrimido[1,2-a]pyrimidin-4-one;

9-(2-{2-(ethyl-2-phenyl)amino}-pyrimidin-4-yl)-2-phenyl-6,7,8,9-tetrahydro-pyrimido[1,2-a]pyrimidin-4-one;

9-(2-{2-(ethyl-2-phenyl-2-ol)amino}-pyrimidin-4-yl) - 2-phenyl-6,7,8,9-tetrahydro-pyrimido[1,2-a]pyrimidin-4-one;

9-(2-{2-(propyl-1-phenyl)amino}-pyrimidin-4-yl)-2-phenyl-6,7,8,9-tetrahydro-pyrimido[1,2-a]pyrimidin-4-one;

9-(2-{2-(propyl-2(S)-amino-3-phenyl)amino}-pyrimidin-4-yl)-2-phenyl-6,7,8,9-tetrahydro-pyrimido[1,2-a]pyrimidin-4-one;

9-(2-{2-(propyl-2,2-dimethyl-3-dimethylamino)amino}-pyrimidin-4-yl)-2-phenyl-6,7,8,9-tetrahydro-pyrimido[1,2-a]pyrimidin-4-one;

9-(2-{2-(-propyl-2-methyl)amino}-pyrimidin-4-yl)-2-phenyl-6,7,8,9-tetrahydro-pyrimido[1,2-a]pyrimidin-4-one;

9-(2-{2-(propyl-3-phenyl)amino}-pyrimidin-4-yl)-2-phenyl-6,7,8,9-tetrahydro-pyrimido[1,2-a]pyrimidin-4-one;

9-(2-{2-[3-(isopropylamino-methyl)-phenyl]-1-methyl - ethylamino}-pyrimidin-4-yl)-2-phenyl-6,7,8,9-tetrahydro-pyrimido[1,2-a]pyrimidin-4-one;

9-(2-{2amino}-pyrimidin-4-yl)-2-phenyl-6,7,8,9-tetrahydro-pyrimido[1,2-a]pyrimidin-4-one;

9-{2-[2-(3-aminomethyl-phenyl)-1(R)-methyl-ethylamino]-pyrimidin-4-yl}-2-phenyl-6,7,8,9-tetrahydro-pyrimido[1,2-a]pyrimidin-4-one; and 9-{2-[2-(3-aminomethyl-phenyl)-1(S)-methyl-ethylamino]-pyrimidin-4-yl}-2-phenyl-6,7,8,9-tetrahydro-pyrimido[1,2-a]pyrimidin-4-one.

Inhibition of LPS-Induced TNF-α Production in Mice

Male DBA/1LACJ mice are dosed with vehicle or test compounds in a vehicle (the vehicle consisting of 0.5% tragacanth in 0.03 N HCl) 30 minutes prior to lipopolysaccharide (2 mg/Kg, I.V.) injection. Ninety minutes after LPS injection, blood is collected and the serum is analyzed by ELISA for TNF-α levels.

Compounds of the invention may be shown to have anti-inflammatory properties in animal models of inflammation, including carageenan paw edema, collagen induced arthritis and adjuvant arthritis, such as the carageenan paw edema model (C. A. Winter et al Proc. Soc. Exp. Biol. Med. (1962) vol 111, p 544; K. F. Swingle, in R. A. Scherrer and M. W. Whitehouse, Eds., Anti-inflammatory Agents, Chemistry and Phamacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/mL ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per mL DMSO and store aliquots at −20° C.; (d) 250 μM human glucagon (Peninsula): solubilize 0.5 mg vial in 575 μl 0.1N acetic acid (1 μL yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μL 10% BSA (heat-inactivated) and 990 μL Assay Buffer; (g) $^{125}$I-Glucagon (NEN, receptor-grade, 2200 Ci/mmol): dilute to 50,000 cpm/25 μL in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).

2. Add 10 mL Enzyme-free Dissoc. Fluid and hold for about 4 min at 37° C.

3. Gently tap cells free, triturate, take aliquot for counting and centrifuge remainder for 5 min at 1000 rpm.

4. Resuspend pellet in Assay Buffer at 75000 cells per 100 μL.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of I$^{125}$-glucagon binding in the presence of compounds of Formula I. The reagents are combined as follows:

| | Compound/ Vehicle | 250 μM Glucagon | $^{125}$I-Glucagon | CHO/ hGLUR Cells |
|---|---|---|---|---|
| Total Binding + Compound | —/5 μl 5 μl/— | — — | 25 μL 25 μL | 100 μL 100 μL |
| Nonspecific Binding | —/5 μl | 1 μl | 25 μL | 100 μL |

The mixture is incubated for 60 min at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10%FBS); all cell incubations are at 37° C. in a humidified environment containing 5% $CO_2$. COX-1 Assay In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2%FBS) and 1 ng human EL-1b/mL, and the cells incubated for 18-22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1N NaOH and centrifugation to pellet cell debris.

Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

Raf Kinase Assay

In vitro Raf kinase activity is measured by the extent of phosphorylation of the substrate MEK (Map kinase/ERK kinase) by activated Raf kinase, as described in GB 1,238,959 (incorporated herein by reference in its entirety). Phosphorylated MEK is trapped on a filter and incorporation of radiolabeled phosphate is quantified by scintillation counting.

Materials

Activated Raf is produced by triple transfection of Sf9 cells with baculoviruses expressing "Glu-Glu"-epitope tagged Raf,$val^{12}$-H-Ras, and Lck. The "Glu-Glu"-epitope, Glu-Try-Met-Pro-Met-Glu, was fused to the carboxy-terminus of full length c-Raf.

Catalytically inactive MEK (K97A mutation) is produced in Sf9 cells transfected with a baculovirus expressing c-terminus "Glu-Glu" epitope-tagged K97A MEK1.

Anti "Glu-Glu" antibody was purified from cells grown as described in: Grussenmeyer, et al., Proceedings of the National Academy of Science, U.S.A. pp 7952-7954, 1985.

Column buffer: 20 mM Tris pH 8, 100 mM NaCl, 1 mM EDTA, 2.5 mM EGTA, 10 mM $MgCl_2$, 2 mM DTT, 0.4 mM AEBSF, 0.1% n-octylglucopyranoside, 1 nM okadeic acid, and 10 μg/mL each of benzamidine, leupeptin, pepstatin, and aprotinin.

5× Reaction buffer: 125 mM HEPES pH=8, 25 mM $MgCl_2$, 5 mM EDTA, 5 mM $Na_3VO_4$, 100 μg/mL BSA.

Enzyme dilution buffer: 25 mM HEPES pH 8, 1 mM EDTA, 1 mM $Na_3VO_4$, 400 μg/mL BSA.

Stop solution: 100 mM EDTA, 80 mM sodium pyrophosphate.

Filter plates: Milipore multiscreen #SE3MO78E3, Immobilon-P (PVDF).

Methods

Protein purification: Sf9 cells were infected with baculovirus and grown as described in Williams, et al., Proceedings of the National Academy of Science, U.S.A. pp 2922-2926, 1992. All subsequent steps were preformed on ice or at 4° C. Cells were pelleted and lysed by sonication in column buffer. Lysates were spun at 17,000×g for 20 min, followed by 0.22 μm filtration. Epitope tagged proteins were purified by chromatography over GammaBind Plus affinity column to which the "Glu-Glu" antibody was coupled. Proteins were loaded on the column followed by sequential washes with two column volumes of column buffer, and eluted with 50 μg/mL Glu-Tyr-Met-Pro-Met-Glu in column buffer.

Raf kinase assay: Test compounds were evaluated using ten 3-fold serial dilutions starting at 10-100 μM. 10 μL of the test inhibitor or control, dissolved in 10% DMSO, was added to the assay plate followed by the addition of 30 μL of the a mixture containing 10 μL 5× reaction buffer, 1 mM $^{33}P$-γ-ATP (20 μCi/mL), 0.5 μL MEK (2.5 mg/mL), 1 μL 50 mM β-mercaptoethanol. The reaction was started by the addition of 10 μL of enzyme dilution buffer containing 1 mM DTT and an amount of activated Raf that produces linear kinetics over the reaction time course. The reaction was mixed and incubated at room temperature for 90 min and stopped by the addition of 50 μL stop solution. 90 μL aliquots of this stopped solution were transferred onto GFP-30 cellulose microtiter filter plates (Polyfiltronics), the filter plates washed in four well volumes of 5% phosphoric acid, allowed to dry, and then replenished with 25 μL scintillation cocktail. The plates were counted for $^{33}P$ gamma emission using a TopCount Scintillation Reader.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

For the treatment of TNF-α, IL-1β, IL-6, and IL-8 mediated diseases, cancer, and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating a TNF-α, IL-1, IL-6, and IL-8 mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., limments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

What is claimed is:

1. A compound of the formula

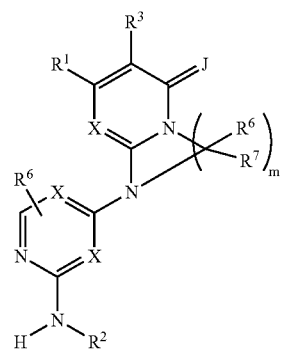

or a pharmaceutically acceptable salt thereof, wherein

J is =O, =S, =CHNO$_2$, =N—CN, =CHSO$_2$R$^b$, =NSO$_2$R$^b$ or =NHR$^b$;

X is, independently at each instance, N or CR$^3$;

R$^1$ is a saturated or unsaturated 5- or 6-membered, ring containing 0, 1, 2 or 3 atoms selected from N, O and S, wherein the ring is substituted by 0, 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C (=O)R$^b$, —S(=O)$_2$N(R$^a$)C(=O)OR$^b$, —S(=O)$_2$N (R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)

C(=NR$^a$)NR$^a$R$^a$, —N(R$^a$)S(=O)$_2$R$^b$, —N(R$^a$)S(=O)$_2$ NR$^a$R$^a$, —NR$^a$C$_{2-6}$ alkylNR$^a$R$^a$ and —NR$^a$C$_{2-6}$alkylOR$^a$;

R$^2$ is C$_{1-8}$alkyl substituted by 0, 1, 2 or 3 substituents selected from C$_{1-2}$haloalkyl, halo, oxo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$ NR$^a$R$^a$, —NR$^a$C$_{2-6}$ alkylNR$^a$R$^a$ and —NR$^a$C$_{2-6}$alkylOR$^a$, and additionally substituted by 0, 1 or 2 substituents selected from R$^g$, —C(=O)R$^g$, —C(=O)OR$^g$, —C(=O)NR$^a$R$^g$, —C(=NR$^a$)NR$^a$R$^g$, —OR$^g$, —OC(=O)R$^g$, —OC(=O)NR$^a$R$^g$, —OC(=O)N(R$^a$)S(=O)$_2$R$^g$, —OC$_{2-6}$alkylNR$^a$R$^g$, —OC$_{2-6}$alkylOR$^g$, —SR$^g$, —S(=O)R$^g$, —S(=O)$_2$R$^g$, —S(=O)$_2$NR$^a$R$^g$, —NR$^a$R$^g$, —N(R$^a$)C(=O)R$^g$, —N(R$^a$)C(=O)OR$^g$, —N(R$^a$)C(=O)NR$^a$R$^g$, —C(=O)R$^e$, —C(=O)OR$^e$, —C(=O)NR$^a$R$^e$, —C(=NR$^a$)NR$^a$R$^e$, —OR$^e$, —OC(=O)R$^e$, —OC(=O)NR$^a$R$^e$, —OC(=O)N(R$^a$)S(=O)$_2$ R$^e$, —OC$_{2-6}$alkyNR$^a$R$^e$, —OC$_{2-6}$alkylOR$^e$, —SR$^e$, —S(=O)R$^e$, —S(=O)$_2$R$^e$, —S(=O)$_2$NR$^a$R$^e$, —NR$^a$R$^e$, —N(R$^a$)C(=O)R$^e$, —N(R$^a$)C(=O)OR$^e$ and —N(R$^a$)C(=O)NR$^a$R$^e$;

R$^3$ is independently at each instance selected from H, R$^e$, C$_{1-4}$haloalkyl, halo, cyano, nitro —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^6$ is independently at each instance H, R$^d$, R$^e$ or R$^g$;
R$^7$ is independently at each instance H, R$^d$, R$^e$ or R$^g$;
m is 2 or 3;
R$^a$ is independently, at each instance, H or R$^b$;
R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, —NH$_2$, —NHC$_{1-4}$alkyl, —N(C$_{1-4}$alkyl)C$_{1-4}$alkyl;
R$^d$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

R$^e$ is independently at each instance C$_{1-6}$alkyl substituted by 0, 1, 2 or 3 substituents independently selected from R$^d$ and additionally substituted by 0 or 1 substituents selected from R$^g$; and R$^g$ is independently at each instance a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo groups and the ring is substituted by 0, 1, or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

2. A compound according to claim 1, wherein R$^1$ is a saturated or unsaturated 5- or 6-membered, ring containing 0, 1, 2 or 3 atoms selected from N, O and S, wherein the ring is substituted by 0, 1, 2 or 3 substituents selected from C$_{1-4}$alkyl, C$_{1-4}$haloalkyl and halo.

3. A compound according to claim 1, wherein R$^1$ is a saturated or unsaturated 5- or 6-membered, ring containing 0, 1, 2 or 3 atoms selected from N, O and S, wherein the ring is substituted by 1, 2 or 3 substituents selected from C$_{1-4}$alkyl, C$_{1-4}$haloalkyl and halo.

4. A compound according to claim 1, wherein R$^1$ is phenyl substituted by 0, 1, 2 or 3 substituents selected from C$_{1-4}$alkyl, C$_{1-4}$haloalkyl and halo.

5. A compound according to claim 1, wherein R$^1$ is thiophenyl, furanyl, pyrrolyl, oxazole or triazole, any of which is substituted by 0, 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$ and —NR$^a$C$_{2-6}$alkylOR$^a$; wherein R$^1$ is not thiazole, imidazole or pyrazole.

6. A compound according to claim 1, wherein R$^1$ is a saturated or unsaturated 6-membered, ring containing 1, 2 or 3 atoms selected from N, O and S, wherein the ring is substituted by 0, 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkylNR$^a$R$^a$ and —NR$^a$C$_{2-6}$alkylOR$^a$.

7. A compound according to claim 1, wherein R$^1$ is an unsaturated 6-membered, ring containing 1, 2 or 3 N atoms, wherein the ring is substituted by 0, 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkylNR$^a$R$^a$ and —NR$^a$C$_{2-6}$alkylOR$^a$.

8. A compound according to claim 1, wherein R$^1$ is phenyl substituted by 0, 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkylNR$^a$R$^a$ and —NR$^a$C$_{2-6}$alkylOR$^a$.

9. A compound according to claim 1, wherein R$^1$ is phenyl substituted by 1, 2 or 3 substituents selected from C$_{1-4}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkylNR$^a$R$^a$ and —NR$^a$C$_{2-6}$alkylOR$^a$.

10. A compound according to claim 1, wherein R$^1$ is phenyl, pyridinyl or pyrimidinyl, all of which are substituted by 0,1 or 2 substituents selected from halo, C$_{1-3}$alkyl and CF$_3$.

11. A compound according to claim 1, wherein R$^1$ is phenyl, pyridinyl or pyrimidinyl.

12. A compound according to claim 1, wherein R$^1$ is pyridinyl substituted by 0, 1, 2 or 3 substituents selected from C$_{1-4}$alkyl, C$_{1-4}$haloalkyl and halo.

13. A compound according to claim 1, wherein R$^1$ is pyrimidinyl substituted by 0, 1, 2 or 3 substituents selected from C$_{1-4}$alkyl, C$_{1-4}$haloalkyl and halo.

14. A compound according to claim 1, wherein R$^1$ is a saturated or unsaturated 5-membered, ring containing 1 or 2 atoms selected from N, O and S, wherein the ring is substituted by 0, 1, 2 or 3 substituents selected from C$_{1-4}$alkyl, C$_{1-4}$haloalkyl and halo.

15. A compound that is selected from:

1-(2-{2-[3-(1-amino-1-methyl-ethyl)-phenyl]-1-methyl-ethylamino}-pyrimidin-4-yl)-8-phenyl-1,2,3,6-tetrahydro-pyrimido[1,2-a]pyrimidin-4-one;

1-(2-{2-[4-(1-amino-ethyl)-phenyl]-ethylamino}-pyrimidin-4-yl)-8-phenyl-1,23,6-tetrahydro-pyrimido[1,2-a]pyrimidin-4-one;

1-(2-{2[4-(1-isopropylamino-ethyl)-phenyl]-ethylamino}-pyrimidin-4-yl)-8-phenyl-1,2,3,6-tetrahydro-pyrimido[1,2-a]pyrimidin-4-one;

1-(2-{2-[4-(2-amino-propyl)-phenyl]-1-methyl -ethylamino}-pyrimidin-4-yl)-8-phenyl-1,2,3,6-tetrahydro-pyrimido[1,2-a]pyrimidin-4-one;

1-(2-phenethylamino-pyrimidin-4-yl)-7-phenyl-2,3-dihydro-1H-imidazo[1,2-a]pyridin-5-one;

1-(2-phenethylamino-pyrimidin-4-yl)-8-phenyl-1,2,3,4-tetrahydro-pyrido[1,2-a]pyrimidin-6-one;

1-(6-phenethylamino-pyrazin-2-yl)-7-phenyl-2,3-dihydro-1H-imidazo[1,2-a]pyridin-5-one;

1-(6-phenethylamino-pyrimidin-4-yl)-8-phenyl-1,2,3,4-tetrahydro-pyrido[1,2-a]pyrimidin-6-one;

1-{2-(S)-[1-(3-bromo-phenyl)-ethylamino]-pyrimidin-4-yl}-8-phenyl-1,2,3,4-tetrahydro-pyrido[1,2-a]pyrimidin-6-one;

1-{2-[(1S)-(4-methoxy-phenyl)-ethylamino]-pyrimidin-4-yl}-8-phenyl-1,2,3,4-tetrahydro-pyrido[1,2-a]pyrimidin-6-one;

1-{2-[2-(2,4-dichloro-phenyl)-ethylamino]-pyrimidin-4-yl}-8-phenyl-1,2,3,4-tetrahydro-pyrido[1,2-a]pyrimidin-6-one;

1-{2-[2-(2,6-dichloro-phenyl)-ethylamino]-pyrimidin-4-yl}-8-phenyl-1,2,3,4-tetrahydro-pyrido[1,2-a]pyrimidin-6-one;

1-{2-[2-(2-chloro-phenyl)-ethylamino]-pyrimidin-4-yl}-8-phenyl-1,2,3,4-tetrahydro-pyrido[1,2-α]pyrimidin-6-one;

1-{2-[2-(3-aminomethyl-phenyl)-1-methyl-ethylamino]-pyrimidin-4-yl}-8-phenyl-1,2,3,4-tetrahydro-pyrido[1,2-α]pyrimidin-6-one;

1-{2-[2-(3-hydroxymethyl-phenyl)-1-methyl-ethylamino]-pyrimidin-4-yl}-8-phenyl-1,2,3,4-tetrahydro-pyrido[1,2-α]pyrimidin-6-one;

1-{2-[2-(3-hydroxymethyl-phenyl)-1-methyl-ethylamino]-pyrimidin-4-yl}-7-phenyl-2,3-dihydro-1H-imidazo[1,2-α]pyridin-5-one;

1-{2-[2-(4-aminomethyl-phenyl)-1-methyl-ethylamino]-pyrimidin-4-yl}-8-phenyl-1,2,3,6-tetrahydro-pyrimido[1,2-a]pyrimidin-4-one;

1-{6-[2-(2-chloro-phenyl)-ethylamino]-pyrimidin-4-yl}-8-phenyl-1,2,3,4-tetrahydro-pyrido[1,2-α]pyrimidin-6-one;

2-(2-fluorophenyl)-9-[2-(1(S)-phenyl-ethylamino)-pyrimidin-4-yl]-6,7,8,9-tetrahydro-pyrimido[1,2-a]pyrimidin-4-one;

2-(2-trifluoromethylphenyl)-9-[2-(1(S)-phenyl-ethylamino)-pyrimidin-4-yl]-6,7,8,9-tetrahydro-pyrimido[1,2-a]pyrimidin-4-one;

2-(3,4-dichlorophenyl)-9-[2-(1(S)-phenyl-ethylamino)-pyrimidin-4-yl]-6,7,8,9-tetrahydro-pyrimido[1,2-a]pyrimidin-4-one;

2-(3,4-dimethyl-phenyl)-9-[2-(1(S)-phenyl-ethylamino)-pyrimidin-4-yl]-6,7,8,9-tetrahydro-pyrimido[1,2-a]pyrimidin-4-one;

2-(3-aminophenyl)-9-[2-(1(S)-phenyl-ethylamino)-pyrimidin-4-yl]-6,7,8,9-tetrahydro-pyrimido[1,2-a]pyrimidin-4-one;

2-(3-dimethylaminephenyl)-9-[2-(1(S)-phenyl-ethylamino)-pyrimidin-4-yl]-6,7,8,9-tetrahydro-pyrimido[1,2-a]pyrimidin-4-one;

2-(3-ethylphenyl)-9-[2-(1(S)-phenyl-ethylamino)-pyrimidin-4-yl]-6,7,8,9-tetrahydro-pyrimido[1,2-a]pyrimidin-4-one;

2-(3-nitrophenyl)-9-[2-(1(S)-phenyl-ethylamino)-pyrimidin-4-yl]-6,7,8,9-tetrahydro-pyrimido[1,2-a]pyrimidin-4-one;

2-(4-fluorophenyl)-9-[2-(1(S)-phenyl-ethylamino)-pyrimidin-4-yl]-6,7,8,9-tetrahydro-pyrimido[1,2-a]pyrimidin-4-one;

2-(4-methoxyphenyl)-9-[2-(1(S)-phenyl-ethylamino)-pyrimidin-4-yl]-6,7,8,9-tetrahydro-pyrimido[1,2-a]pyrimidin-4-one;

2-(4-pyridyl)-9-[2-(1(S)-phenyl-ethylamino)-pyrimidin-4-yl]-6,7,8,9-tetrahydro-pyrimido[1,2-a]pyrimidin-4-one;

2-(phenyl)-9-[2-(1(S)-phenyl-ethylamino)-pyrimidin-4-yl]-6,7,8,9-tetrahydro-pyrimido[1,2-a]pyrimidin-4-one;
2-(tert-butyl)-9-[2-(1(S)-phenyl-ethylamino)-pyrimidin-4-yl]-6,7,8,9-tetrahydro-pyrimido[1,2-a]pyrimidin-4-one;
2-{-[2-(3-aminomethyl-phenyl)-1-methyl-ethylamino]-pyrimidine-4-ylamino}-3-methyl-6-phenyl-3H-pyrimidin-4-one;
3-amino-9-{2-[2-(3-aminomethyl-phenyl)-1-methyl-ethylamino]-pyrimidin-4-yl}-2-phenyl-6,7,8,9-tetrahydro-pyrimido[1,2-a]pyrimidin-4-one;
3-amino-9-{2-[ethyl-2-(2-chlorophenyl)]-pyrimidin-4-yl}-2-phenyl-6,7,8,9-tetrahydro-pyrido[1,2-a]pyrimidin-4-one;
3-amino-9-{2-[ethyl-2-phenyl]-pyrimidin-4-yl}-2-phenyl-6,7,8,9-tetrahydro-pyrimido[1,2-a]pyrimidin-4-one;
3-methyl-9-{2-[1-(S)-phenylethyl]-pyrimidin-4-yl}-2-phenyl-6,7,8,9-tetrahydro-pyrimido[1,2-a]pyrimidin-4-one;
3-nitro-9-{2-[ethyl-2-phenyl]-pyrimidin-4-yl}-2-phenyl-6,7,8,9-tetrahydro-pyrimido[1,2-a]pyrimidin-4-one;
7-(2-Isopropylamino-ethyl)-9-(2-phenethylamino-pyrimidin-4-yl) -2-phenyl-6,7,8,9-tetrahydro-pyrimido[1,2-a]pyrimidin-4-one;
7-(ethyl-2-amino(N-benzyl))-9-(2-phenethylamino-pyrimidin-4-yl)-2-phenyl-6,7,8,9-tetrahydro-pyrimido[1,2-a]pyrimidin-4-one;
7-(ethyl-2-amino)-9-(2-phenethylamino-pyrimidin-4-yl)-2-phenyl-6,7,8,9-tetrahydro-pyrimido[1,2-a]pyrimidin-4-one;
7-(ethyl-2-carbamic acid benzyl ester)-9-(2-phenethylamino-pyrimidin -4-yl)-2-phenyl-6,7,8,9-tetrahydro-pyrimido[1,2-a]pyrimidin-4-one;
7-(propionic acid )-9-(2-phenethylamino-pyrimidin-4-yl)-2-phenyl-6,7,8,9-tetrahydro-pyrimido[1,2-a]pyrimidin-4-one;
7-(propionic acid ethyl ester)-9-(2-phenethylamino-pyrimidin-4-yl) -2-phenyl-6,7,8,9-tetrahydro-pyrimido[1,2-a]pyrimidin-4-one;
7-hydroxy-2-phenyl-9-[2-(1-phenyl-ethylamino)-pyrimidin -4-yl]-6,7,8,9-tetrahydro-pyrimido[1,2-a]pyrimidin-4-one;
8-phenyl-1-[2-(1S)-phenyl-ethylamino)-pyrimidin-4-yl]-1,2,3,4-tetrahydro-pyrido[1,2-a]pyrimidin-6-one;
8-phenyl-1-[2-(2S)-phenyl-propylamino)-pyrimidin-4-yl]-1,2,3,4-tetrahydro-pyrido[1,2-a]pyrimidin-6-one;
8-phenyl-1-{2-(S)-[1-(3-piperazin-1-yl -phenyl) -ethylamino]-pyrimidin-4-yl}-1,2,3,4-tetrahydro-pyrido[1,2-a]pyrimidin-6-one;
9-(2-{2-(2-hydroxyethyl)amino}-pyrimidin-4-yl) -2-phenyl-6,7,8,9-tetrahydro-pyrimido[1,2-a]pyrimidin-4-one;
9-{2-{2-(benzyl)amino}-pyrimidin-4-yl)-2-phenyl -6,7,8,9-tetrahydro-pyrimido[1,2-a]pyrimidin-4-one;
9-(2-{2-(ethyl-1(S)-isopropyl-2-ol)amino}-pyrimidin -4-yl)-2-phenyl-6,7,8,9-tetrahydro-pyrimido[1,2-a]pyrimidin-4-one;
9-(2-{2-(ethyl-1(S)methyl-2-(3-methylaminophenyl)) amino}-pyrimidin-4-yl)-2-phenyl-6,7,8,9-tetrahydro-pyrimido[1,2-a]pyrimidin-4-one;
9-(2-{2-(ethyl-1(S)-methyl-2-ol)amino}-pyrimidin-4-yl)-2-phenyl-6,7,8,9-tetrahydro-pyrimido[1,2-a]pyrimidin-4-one;
9-(2-{2-(ethyl-1(S)methyl-2-phenyl)amino}-pyrimidin -4-yl)-2-phenyl-6,7,8,9-tetrahydro-pyrimido[1,2-a]pyrimidin-4-one;
9-(2-{2-(ethyl-1-amido-2-phenyl)amino}-pyrimidin-4-yl)-2-phenyl-6,7,8,9-tetrahydro-pyrimido[1,2-a]pyrimidin-4-one;
9-(2-{2-(ethyl-1-methyl-2-(3-aminophenyl))amino}-pyrimidin-4-yl)-2-phenyl-6,7,8,9-tetrahydro-pyrimido[1,2-a]pyrimidin-4-one;
9-(2-{2-(ethyl-1-methyl-2-(3-cyanophenyl))amino}-pyrimidin-4-yl)-2-phenyl-6,7,8,9-tetrahydro-pyrimido[1,2-a]pyrimidin-4-one;
9-(2-{2-(ethyl-1-methyl-2-(3-methylalcoholphenyl)) amino}-pyrimidin-4-yl)-2-phenyl -6,7,8,9-tetrahydro-pyrimido[1,2-a]pyrimidin-4-one;
9-(2-{2-(ethyl-1-methyl-2-(3-methylaminophenyl)) amino}-pyrimidin-4-yl)-2-phenyl -6,7,8,9-tetrahydro-pyrimido[1,2-a]pyrimidin-4-one;
9-(2-{2-(ethyl-2-(2-chlorophenyl))amino}-pyrimidin-4-yl)-2-phenyl-6,7,8,9-tetrahydro-pyrimido[1,2-a]pyrimidin-4-one;
9-(2-{2-(ethyl-2-(2-methoxyphenyl))amino}-pyrimidin-4-yl)-2-phenyl-6,7,8,9-tetrahydro-pyrimido[1,2-a]pyrimidin-4-one;
9-(2-{2-(ethyl-2-(3,4-dimethylphenyl))amino}-pyrimidin-4-yl)-2-phenyl-6,7,8,9-tetrahydro-pyrimido[1,2-a]pyrimidin-4-one;
9-(2-{2-(ethyl-2-(4-hydroxyphenyl))amino}-pyrimidin -4-yl)-2-phenyl-6,7,8,9-tetrahydro-pyrimido[1,2-a]pyrimidin-4-one;
9-(2-{2-(ethyl-2-(4-methoxyphenyl))amino}-pyrimidin -4-yl)-2-phenyl-6,7,8,9-tetrahydro-pyrimido[1,2-a]pyrimidin-4-one;
9-(2-{2-(ethyl-2-(4-methylphenyl))amino}-pyrimidin-4-yl)-2-phenyl-6,7,8,9-tetrahydro-pyrimido[1,2-a]pyrimidin-4-one;
9-(2-{2-(ethyl-2-aminophenyl)amino}-pyrimidin-4-yl) -2-phenyl-6,7,8,9-tetrahydro-pyrimido[1,2-a]pyrimidin-4-one;
9-(2-{2-(ethyl-2-keto-2-phenyl)amino}-pyrimidin-4-yl)-2-phenyl-6,7,8,9-tetrahydro-pyrimido[1,2-a]pyrimidin-4-one;
9-(2-{2-(ethyl-2-methoxy)amino}-pyrimidin-4-yl)-2-phenyl-6,7,8,9-tetrahydro-pyrimido[1,2-a]pyrimidin-4-one;
9-(2-{2-(ethyl-2-morpholino)amino}-pyrimidin-4-yl)-2-phenyl-6,7,8,9-tetrahydro-pyrimido[1,2-a]pyrimidin-4-one;
9-(2-{2-(ethyl-2-phenoxy)amino}-pyrimidin-4-yl)-2-phenyl-6,7,8,9-tetrahydro-pyrimido[1,2-a]pyrimidin-4-one;
9-(2-{2-(ethyl-2-phenyl)amino}-pyrimidin-4-yl)-2-phenyl-6,7,8,9-tetrahydro-pyrimido[1,2-a]pyrimidin-4-one;
9-(2-{2-(ethyl-2-phenyl-2-ol)amino}-pyrimidin -4-yl)-2-phenyl-6,7,8,9-tetrahydro-pyrimido[1,2-a]pyrimidin-4-one;
9-(2-{2-(propyl-1-phenyl)amino}-pyrimidin-4-yl) -2-phenyl-6,7,8,9-tetrahydro-pyrimido[1,2-a]pyrimidin-4-one;
9-(2-{2-(propyl-2(S)-amino-3-phenyl)amino}-pyrimidin -4-yl)-2-phenyl-6,7,8,9-tetrahydro-pyrimido[1,2-a]pyrimidin-4-one;

9-(2-{2-(propyl-2,2-dimethyl-3-dimethylamino)amino}-pyrimidin-4-yl)-2-phenyl-6,7,8,9-tetrahydro-pyrimido[1,2-a]pyrimidin-4-one;

9-(2-{2-(-propyl-2-methyl)amino}-pyrimidin-4-yl)-2-phenyl-6,7,8,9-tetrahydro-pyrimido[1,2-a]pyrimidin-4-one;

9-(2-{2-(propyl-3-phenyl)amino}-pyrimidin-4-yl)-2-phenyl-6,7,8,9-tetrahydro-pyrimido[1,2-a]pyrimidin-4-one;

9-(2-{2-[3-(isopropylamino-methyl)-phenyl]-1-methyl-ethylamino}-pyrimidin-4-yl)-2-phenyl-6,7,8,9-tetrahydro-pyrimido[1,2-a]pyrimidin-4-one;

9-(2-{2-amino}-pyrimidin-4-yl)-2-phenyl-6,7,8,9-tetrahydro-pyrimido[1,2-a]pyrimidin-4-one;

9-{2-[2-(3-aminomethyl-phenyl)-1(R)-methyl-ethylamino]-pyrimidin-4-yl}-2-phenyl-6,7,8,9-tetrahydro-pyrimido[1,2-a]pyrimidin-4-one; and 9-{2-[2-(3-aminomethyl-phenyl)-1(S)-methyl-ethylamino]-pyrimidin-4-yl}-2-phenyl-6,7,8,9-tetrahydro-pyrimido[1,2-a]pyrimidin-4-one.

16. A pharmaceutical composition comprising a compound according to claim 1 and a pharmaceutically acceptable carrier.

17. A method of treatment of rheumatoid arthritis, osteoarthritis, inflammatory bowel disease, psoriasis, Crohn's disease in a mammal comprising administering an effective amount of a compound according to claim 1.

* * * * *